(12) United States Patent
Toida et al.

(10) Patent No.: US 11,137,686 B2
(45) Date of Patent: *Oct. 5, 2021

(54) MATERIAL FOR FORMING UNDERLAYER FILM FOR LITHOGRAPHY, COMPOSITION FOR FORMING UNDERLAYER FILM FOR LITHOGRAPHY, UNDERLAYER FILM FOR LITHOGRAPHY AND PRODUCTION METHOD THEREOF, AND RESIST PATTERN FORMING METHOD

(71) Applicant: Mitsubishi Gas Chemical Company, Inc., Tokyo (JP)

(72) Inventors: Takumi Toida, Hiratsuka (JP); Takashi Makinoshima, Hiratsuka (JP); Takashi Sato, Hiratsuka (JP); Masatoshi Echigo, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/756,463

(22) PCT Filed: Aug. 25, 2016

(86) PCT No.: PCT/JP2016/074865
§ 371 (c)(1),
(2) Date: Feb. 28, 2018

(87) PCT Pub. No.: WO2017/038643
PCT Pub. Date: Mar. 9, 2017

(65) Prior Publication Data
US 2018/0246409 A1 Aug. 30, 2018

(30) Foreign Application Priority Data

Aug. 31, 2015 (JP) .............................. JP2015-170190

(51) Int. Cl.
G03F 7/16 (2006.01)
G03F 7/11 (2006.01)
(Continued)

(52) U.S. Cl.
CPC ................ *G03F 7/30* (2013.01); *C07C 39/12* (2013.01); *C07C 39/14* (2013.01); *C07D 405/04* (2013.01);
(Continued)

(58) Field of Classification Search
CPC . G03F 7/11; G03F 7/0392; G03F 7/30; G03F 7/16; G03F 7/168; C07C 39/12; C07C 39/14
(Continued)

(56) References Cited

U.S. PATENT DOCUMENTS 2,100,798 A   11/1937 Dilthey
2,546,872 A   3/1951 Schmid
(Continued)

FOREIGN PATENT DOCUMENTS

CN   1414031   4/2003
CN   1853141   10/2006
(Continued)

OTHER PUBLICATIONS

International Search Report for PCT/JP2014/051775, dated Feb. 25, 2014, and English translation (4 pages).
(Continued)

*Primary Examiner* — John S Chu
(74) *Attorney, Agent, or Firm* — Fitch, Even, Tabin & Flannery LLP

(57) ABSTRACT

The present invention provides a material for forming an underlayer film for lithography, containing at least any of a compound represented by following formula (1) or a resin including a structural unit derived from a compound represented by the following formula (1),

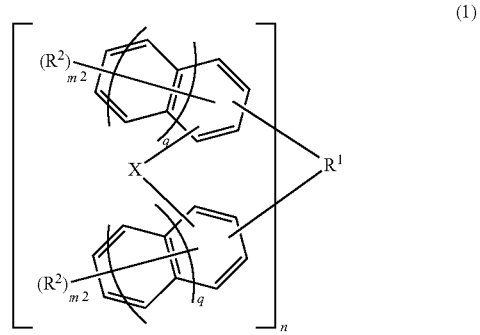

(1)

wherein $R^1$ represents a 2n-valent group having a 1 to 60 carbon atoms, or a single bond, each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, or a hydroxyl group, and may be the same or different in the same naphthalene ring or benzene ring, n is an integer of 1 to 4, structural formulae of n's structural units in square brackets [ ] may be the same or different when n is an integer of 2 or more, X represents an oxygen atom, a sulfur atom, or a non-bridging group, each m2 is independently an integer of 0 to 7, in which at least one $m^2$ is an integer of 1 to 7, and each q is independently 0 or 1, provided that at least one selected from the group consisting of $R^1$ and $R^2$ is a group having an iodine atom.

10 Claims, No Drawings

(51) Int. Cl.

| | | |
|---|---|---|
| G03F 7/004 | (2006.01) | |
| G03F 7/30 | (2006.01) | |
| C07D 405/04 | (2006.01) | |
| G03F 7/09 | (2006.01) | |
| C07C 39/14 | (2006.01) | |
| C07C 39/12 | (2006.01) | |
| C08G 61/12 | (2006.01) | |
| C09D 165/00 | (2006.01) | |
| G03F 7/20 | (2006.01) | |
| G03F 7/32 | (2006.01) | |
| G03F 7/38 | (2006.01) | |
| H01L 21/027 | (2006.01) | |

(52) U.S. Cl.
 CPC ......... *C08G 61/122* (2013.01); *C09D 165/00* (2013.01); *G03F 7/091* (2013.01); *G03F 7/094* (2013.01); *G03F 7/11* (2013.01); *G03F 7/16* (2013.01); *G03F 7/162* (2013.01); *G03F 7/168* (2013.01); *G03F 7/2037* (2013.01); *G03F 7/322* (2013.01); *G03F 7/38* (2013.01); *H01L 21/0274* (2013.01); *C08G 2261/11* (2013.01); *C08G 2261/146* (2013.01); *C08G 2261/148* (2013.01); *C08G 2261/149* (2013.01); *C08G 2261/1424* (2013.01); *C08G 2261/3242* (2013.01); *C08G 2261/59* (2013.01); *C08G 2261/76* (2013.01); *C08G 2261/90* (2013.01)

(58) Field of Classification Search
 USPC ............ 430/270.1, 271.1, 326; 560/61, 100; 568/719
 See application file for complete search history.

(56) References Cited

U.S. PATENT DOCUMENTS

| | | | |
|---|---|---|---|
| 2,587,437 A | 2/1952 | Bralley | |
| 3,947,468 A | 3/1976 | Hall | |
| 4,252,884 A | 2/1981 | Bennett | |
| 4,289,839 A | 9/1981 | Dipippo | |
| 4,482,489 A | 11/1984 | Dipippo | |
| 4,579,758 A | 4/1986 | Dorsch | |
| 5,332,648 A | 7/1994 | Kihara | |
| 5,986,094 A | 11/1999 | Ghoshal | |
| 6,784,228 B2 * | 8/2004 | Ogura | C07D 311/78 523/466 |
| 6,794,408 B2 | 9/2004 | Eder | |
| 7,871,751 B2 | 1/2011 | Echigo | |
| 9,136,121 B2 | 9/2015 | Hatakeyama | |
| 9,274,426 B2 | 3/2016 | Rahman | |
| 9,316,913 B2 | 4/2016 | Echigo | |
| 9,540,339 B2 | 1/2017 | Echigo | |
| 9,908,831 B2 | 3/2018 | Echigo | |
| 10,303,055 B2 | 5/2019 | Sato | |
| 10,377,734 B2 | 8/2019 | Echigo | |
| 2002/0106909 A1 | 8/2002 | Kato | |
| 2003/0092852 A1 | 5/2003 | Ogura | |
| 2004/0197709 A1 | 10/2004 | Arase | |
| 2005/0074695 A1 | 4/2005 | Nakamura | |
| 2005/0255712 A1 | 11/2005 | Kato et al. | |
| 2007/0059632 A1 | 3/2007 | Oguro et al. | |
| 2007/0172759 A1 | 7/2007 | Ogihara | |
| 2007/0232839 A1 | 10/2007 | Yoshitomo | |
| 2007/0275325 A1 | 11/2007 | Hatakeyama | |
| 2008/0113294 A1 | 5/2008 | Echigo | |
| 2008/0138744 A1 | 6/2008 | Hatanaka | |
| 2008/0153031 A1 * | 6/2008 | Echigo | G03F 7/0382 430/281.1 |
| 2009/0171061 A1 | 7/2009 | Haruaki | |
| 2009/0246684 A1 | 10/2009 | Kim | |
| 2009/0261300 A1 | 10/2009 | Watanabe | |
| 2010/0047709 A1 | 2/2010 | Echigo | |
| 2010/0099044 A1 | 4/2010 | Hatakeyama | |
| 2010/0104977 A1 | 4/2010 | Hatakeyama | |
| 2010/0136477 A1 | 6/2010 | Ng | |
| 2010/0190107 A1 | 7/2010 | Shibata | |
| 2010/0207516 A1 | 8/2010 | Moriwaki | |
| 2010/0227859 A1 | 9/2010 | Li | |
| 2010/0285407 A1 | 11/2010 | Ogihara | |
| 2010/0316950 A1 | 12/2010 | Oguro et al. | |
| 2011/0177459 A1 | 7/2011 | Ogihara | |
| 2011/0230058 A1 | 9/2011 | Sakamoto et al. | |
| 2011/0274713 A1 | 11/2011 | Burn | |
| 2011/0311920 A1 | 12/2011 | Kinsho | |
| 2012/0064725 A1 | 3/2012 | Kinsho | |
| 2012/0171611 A1 | 7/2012 | Ideno et al. | |
| 2012/0184103 A1 | 7/2012 | Ogihara | |
| 2012/0220112 A1 | 8/2012 | Hatakeyama | |
| 2012/0228584 A1 | 9/2012 | Wigglesworth | |
| 2013/0004896 A1 | 1/2013 | Echigo et al. | |
| 2013/0056653 A1 | 3/2013 | Hatakeyama | |
| 2013/0084705 A1 | 4/2013 | Nakafuji et al. | |
| 2013/0087529 A1 | 4/2013 | Hatakeyama | |
| 2013/0150627 A1 | 6/2013 | Okada | |
| 2014/0186776 A1 | 7/2014 | Uchiyama | |
| 2014/0248556 A1 | 9/2014 | Kato | |
| 2014/0248561 A1 * | 9/2014 | Echigo | C07D 311/96 430/281.1 |
| 2014/0308615 A1 | 10/2014 | Echigo et al. | |
| 2014/0319097 A1 | 10/2014 | Kim | |
| 2014/0363768 A1 | 12/2014 | Kinsho et al. | |
| 2014/0363955 A1 | 12/2014 | Hatakeyama | |
| 2014/0363957 A1 | 12/2014 | Hatakeyama | |
| 2014/0363958 A1 | 12/2014 | Hatakeyama | |
| 2015/0030980 A1 | 1/2015 | Echigo | |
| 2015/0037735 A1 | 2/2015 | Yang | |
| 2015/0090691 A1 | 4/2015 | Echigo et al. | |
| 2015/0309403 A1 | 10/2015 | Rahman | |
| 2015/0368224 A1 | 12/2015 | Echigo | |
| 2015/0376157 A1 * | 12/2015 | Echigo | C07C 69/734 430/270.1 |
| 2015/0376158 A1 | 12/2015 | Echigo | |
| 2015/0376202 A1 | 12/2015 | Echigo | |
| 2016/0130243 A1 | 5/2016 | Satou | |
| 2016/0145231 A1 | 5/2016 | Echigo | |
| 2017/0183279 A1 | 6/2017 | Echigo | |
| 2017/0349564 A1 * | 12/2017 | Toida | C07D 311/78 |
| 2018/0074402 A1 * | 3/2018 | Toida | C07D 311/92 |
| 2018/0074406 A1 | 3/2018 | Toida | |
| 2018/0208703 A1 | 7/2018 | Okada et al. | |

FOREIGN PATENT DOCUMENTS

| | | |
|---|---|---|
| CN | 101889247 | 11/2010 |
| CN | 102070595 | 5/2011 |
| CN | 103304385 A | 9/2013 |
| CN | 103733136 | 4/2014 |
| CN | 103804196 A | 5/2014 |
| CN | 104557552 A | 4/2015 |
| EP | 1275673 | 1/2003 |
| EP | 1300403 | 4/2003 |
| EP | 1666970 | 6/2006 |
| EP | 2743249 | 6/2014 |
| EP | 2743769 A1 | 6/2014 |
| EP | 2743770 A1 | 6/2014 |
| EP | 3279190 A1 | 2/2018 |
| JP | S48049508 A | 7/1973 |
| JP | 62094841 A | 5/1987 |
| JP | S62191850 A | 8/1987 |
| JP | H01283280 | 11/1989 |
| JP | H04217675 | 8/1992 |
| JP | H05-19463 A | 1/1993 |
| JP | H05034913 A | 2/1993 |
| JP | H05134415 A | 5/1993 |
| JP | H05163290 A | 6/1993 |
| JP | 05216235 A | 8/1993 |
| JP | H06049402 A | 2/1994 |
| JP | H06242607 A | 9/1994 |
| JP | H07215833 | 8/1995 |
| JP | H1025220 | 1/1998 |
| JP | H10045764 A | 2/1998 |

(56) References Cited

FOREIGN PATENT DOCUMENTS

| | | |
|---|---|---|
| JP | H11072925 | 3/1999 |
| JP | 2001042525 | 2/2001 |
| JP | 2002214769 | 7/2002 |
| JP | 2002-334869 A | 11/2002 |
| JP | 2002334896 | 11/2002 |
| JP | 2002341542 | 11/2002 |
| JP | 2003201333 | 7/2003 |
| JP | 2004-177668 A | 6/2004 |
| JP | 2004-271838 A | 9/2004 |
| JP | 2005-250434 A | 9/2005 |
| JP | 2005266741 A | 9/2005 |
| JP | 2005326838 A | 11/2005 |
| JP | 2005326868 A | 11/2005 |
| JP | 2005346024 A | 12/2005 |
| JP | 2006036648 | 2/2006 |
| JP | 2006098869 | 4/2006 |
| JP | 2006113136 | 4/2006 |
| JP | 2006160663 | 6/2006 |
| JP | 2006213634 | 8/2006 |
| JP | 2006259482 A | 9/2006 |
| JP | 2007019294 | 1/2007 |
| JP | 2007199653 | 8/2007 |
| JP | 2007-226170 A | 9/2007 |
| JP | 2007-226204 A | 9/2007 |
| JP | 2007262398 | 10/2007 |
| JP | 2007326847 | 12/2007 |
| JP | 2008065081 | 3/2008 |
| JP | 2008145539 A | 6/2008 |
| JP | 2008201954 A | 9/2008 |
| JP | 2008239868 | 10/2008 |
| JP | 2009073738 A | 4/2009 |
| JP | 2009098155 A | 5/2009 |
| JP | 2009108313 | 5/2009 |
| JP | 2009155256 | 7/2009 |
| JP | 2009173623 A | 8/2009 |
| JP | 2009300978 | 12/2009 |
| JP | 2010160189 | 7/2010 |
| JP | 2010170013 | 8/2010 |
| JP | 2010219295 | 9/2010 |
| JP | 2010235643 | 10/2010 |
| JP | 2011068624 | 4/2011 |
| JP | 2011105887 | 6/2011 |
| JP | 2011150023 | 8/2011 |
| JP | 20121687 | 1/2012 |
| JP | 2012-077295 A | 4/2012 |
| JP | 2012068652 | 4/2012 |
| JP | 2012083731 A | 4/2012 |
| JP | 2012145897 | 8/2012 |
| JP | 2013064978 A | 4/2013 |
| JP | 2013-083939 A | 5/2013 |
| JP | 2013083833 A | 5/2013 |
| JP | 2013087173 A | 5/2013 |
| JP | 2013137524 A | 7/2013 |
| JP | 2013253161 A | 12/2013 |
| JP | 2014196288 A | 10/2014 |
| JP | 2014205746 | 10/2014 |
| JP | 2015018220 | 1/2015 |
| JP | 2015018221 | 1/2015 |
| JP | 2015018223 | 1/2015 |
| JP | 2015087115 A | 5/2015 |
| JP | 2015514691 A | 5/2015 |
| JP | 2015-127821 A | 7/2015 |
| KR | 1020100095563 | 8/2010 |
| WO | 9736960 | 10/1997 |
| WO | 0214434 | 2/2002 |
| WO | 03017002 | 2/2003 |
| WO | 2004/066377 A1 | 8/2004 |
| WO | 2005/029189 A1 | 3/2005 |
| WO | 2005111724 | 11/2005 |
| WO | 2006/068267 A1 | 6/2006 |
| WO | 2007097457 | 8/2007 |
| WO | 2008053974 A1 | 5/2008 |
| WO | 2008137816 A2 | 11/2008 |
| WO | 2009/072465 A1 | 6/2009 |
| WO | 2009119201 A1 | 10/2009 |
| WO | 2009145224 | 12/2009 |
| WO | 2011/034062 A1 | 3/2011 |
| WO | 2012165507 A1 | 12/2012 |
| WO | 2013/010102 A2 | 1/2013 |
| WO | 2013/024777 A1 | 2/2013 |
| WO | 2013/024778 A1 | 2/2013 |
| WO | 2013/024779 A1 | 2/2013 |
| WO | 2013066067 | 5/2013 |
| WO | 2013184755 | 12/2013 |
| WO | 2014050690 | 4/2014 |
| WO | 2014/123032 A1 | 8/2014 |
| WO | 2014199660 | 12/2014 |

OTHER PUBLICATIONS

International Search Report for PCT/JP2015/084907, dated Feb. 9, 2016, and English translation (7 pages).
International Search Report for PCT/JP2014/052524, dated Mar. 25, 2014, and English Translation (8 pages).
International Search Report for PCT/JP2014/052530, dated May 13, 2014, and English Translation (8 pages).
International Search Report for PCT/JP2012/070304, dated Oct. 23, 2012, and English translation (9 pages).
International Search Report for PCT/JP2012/070305, dated Sep. 11, 2012, and English Translation (5 pages).
International Search Report for PCT/JP2016/056332, dated May 31, 2016, and English translation (11 pages).
International Search Report for PCT/JP2016/056333, dated May 24, 2016, and English translation (7 pages).
Written Opinion of the International Searching Authority for PCT/JP2012/070304, dated Oct. 23, 2012, and English translation (12 pages).
Luo, Junfei et al., "Salicylic acids as readily available starting materials for the synthesis of meta-substituted biaryls," ChemComm, 2015, vol. 51, pp. 3127-3130.
U.S. Appl. No. 15/539,560, entitled "Compound, Resin, Material for Forming Underlayer Film for Lithography, Underlayer Film for Lithography, Pattern Forming Method, and Purification Method," filed Jun. 23, 2017, which entered the U.S. national phase from International Application No. PCT/JP2015/084907, filed on Dec. 14, 2015, which published as US 2017/0349564 A1 on Dec. 7, 2017.
U.S. Appl. No. 15/560,059, Entitled "Compound, Resist Composition, and Method for Forming Resist Pattern Using It," filed Sep. 20, 2017, which entered the U.S. national phase from International Application No. PCT/JP2016/056332, filed on Mar. 2, 2016, which published as US 2018/0074406 A1 on Mar. 15, 2018.
U.S. Appl. No. 15/560,458, entitled "Resist Composition, Method for Forming Resist Pattern, and Polyphenol Compound Used Therein," filed Sep. 21, 2017, which entered the U.S. national phase from International Application No. PCT/JP2016/056333, filed on Mar. 2, 2016, which published as US 2018/0074402 A1 on Mar. 15, 2018.
U.S. Appl. No. 15/755,972, entitled "Material for Forming Underlayer Film for Lithography, Composition for Forming Underlayer Film for Lithography, Underlayer Film for Lithography and Production Method Thereof, Pattern Forming Method, Resin, and Purification Method," filed Feb. 27, 2018, which entered the U.S. national phase from International Application No. PCT/JP2016/074867, filed on Aug. 25, 2016, which published as US 2019/0041750 A1 on Feb. 7, 2019.
U.S. Appl. No. 15/759,076, entitled "Compound, Resin, Resist Composition or Radiation-Sensitive Composition, Resist Pattern Formation Method, Method for Producing Amorphous Film, Underlayer Film Forming Material For Lithography, Composition For Underlayer Film Formation For Lithography, Method For Forming Circuit Pattern, and Purification Method," filed Mar. 9, 2018, which entered the U.S. national phase from International Application No. PCT/JP2016/076392, filed on Sep. 8, 2016, which published as US 2019/0056657 A1 on Feb. 21, 2019.
Ahmed Munir et al., The Direct Bradsher Reaction. Part I. Synthesis of Thiophen Analogues of Linear Polycyclic Hydrocarbons, Journal of the Chemical Society, Perkin Transactions 1,1973, pp. 1099-1103.

(56) References Cited

OTHER PUBLICATIONS

Areephong, Jetsuda, et al., "A concise synthesis of functionalized 7-oxa-[5]-helicenes," Tetrahedron Letters, 2004, vol. 45, pp. 3067-3070.
Bentley, K. W., and Robinson, R., "A Synthesis of alpha-Anhydrotrimethylbrazilone," Tetrahedron Letters, 1959, vol. 1, Issue 2, pp. 11-14.
Brecher, Jonathan, Graphical Representation Standards for Chemical Structure Diagrams, Pure Appl. Chem., 2008, pp. 277-410, vol. 80, No. 2, Cambridge, Massachusetts.
Burnett, James C., et al. "Novel small molecule inhibitors of botulinum neurotoxin A metalloprotease activity," Biochemical and Biophysical Research Communications, vol. 310, No. 1, Oct. 2003, pp. 84-93.
Cameron, Donald W., et al., "Synthesis of a natural polychloro dinaphthofuran quinone," Tetrahedron Letters, 1980, vol. 21(14), pp. 1385-1386.
Chatterjea, J.N., "Experiments on the Syntheses of Furano Compounds. Part XII. Further Transformations of isoCoumaranone," Journal of the Indian Chemical Society, 1957, vol. 34, Issue 4, pp. 299-305.
Clowes, G. A., et al., "Studies of the Scholl reaction: Oxidative Dehydrogenation involving 1-Ethoxynaphthylenen and Related Compounds," J Chem. Soc (C) 2519-2526 (1968).
Dann, von Otto, and Hofmann, Hans, Synthese von ()-Brasilin, Justus Liebigs Annalen der Chemie, 1963, vol. 667, Issue 1, pp. 116-125.
English Translation of JP H01-283280 A, Nov. 14, 1989.
European Journal of Medicinal Chemistry, published bi-monthly, Ejmcs, 13(4): 381-385 (1978).
Ghodratbeigi Mohsen et al., "Design, modeling and synthesis of molecular tweezers with self-assembly Properties," Journal of Molecular Structure, 2011, vol. 990, No. 1, pp. 140-151.
Hagihara K. et al., "The effect of Ti-addition on plastic deformation and fracture behavior of directionally solidified NIiAl/Cr(Mo) eutetic alloys," Intermetallics, 2006, vol. 14, No. 10, pp. 1326-1331.
Hannuksela, Miska M. et al., "Hook for scalable extensions: video parameter set," Joint Collaborative Team on Video Coding (JCT-VC) of ITU-T SG 16 WP 3 and ISO/IEC JTC 1/SC 29/WG 11, May 2012, pp. 1-6.
Jha Amitabh and Beal Jennifer, "Convenient synthesis of 12H-benzo[a]xanthenes from 2-tetralone," Tetrahedron Letters, 2004, vol. 45, No. 49, pp. 8999-9001.
Journal of the Chemical Society, p. 5336-5341 (Nov. 1963).
Machine English Translation of JP 2008-239868 A, Oct. 9, 2008.
Massif, Cedrik, et al. "New insights into the water-solubilisation of fluorophores by post-synthetic 'click' and Sonogashira reactions," Organic & Biomolecular Chemistry, vol. 10, No. 22, Apr. 2012, pp. 4430-4336.
Nakayama, Tomonari, Nomura, Masayoshi, Haga, Kohji, and Ueda, Mitsuru, A New Three-Component Photoresist Based on Calix[4]resorcinarene Derivative, a Cross-Linker, and a Photo-acid Generator, The Chemical Society of Japan, Bulletin of the Chemical Society of Japan, 1998, vol. 71, No. 12, pp. 2979-2984.
Nature, 161:930-931 (1948).
Nishiyama Tomihiro et al., Antioxidant activities of fused heterocyclic compounds, xanthene-2,7-diols with BHT or Catechol skeleton, Polymer Degradation and Stability, 1998, vol. 62, No. 3, pp. 529-534.
Ohishi Takeshi. Tetrahedron Letters 42 (2001) 2493-2496.
Osman A-M, Reactions Between Chloro-p-benzoquinones and Beta-Naphtol, Journal of Organic Chemistry, 1957, vol. 22, pp. 342-344.
Percec, Virgil, et al., Synthesis of Aromatic Polyethers by Scholl Reaction. I. Poly(1,1'-Dinaphthyl Ether Phenyl Sulfone)s and Poly(1,1'-Dinaphthyl Ether Phenyl Ketone)s, Journal of Polymer Science: Part A: Polymer Chemistry, 1988, vol. 26, pp. 783-805.
Percec, Virgil, et al., "Synthesis of Aromatic Polyethers by Scholl Reaction. VI. Aromatic Polyethers by Cation-Radical Polymerization of 4,4'-, 3,3'-, and 2-2'-Bis(1-naphthoxy)biphenyls and of 1,3-Bis(1-naphthoxy)benzene," Macromolecules, 1992, vol. 25(1), pp. 64-74.
Protiva, Miroslav et al., Potential metabolites of tricyclic neuroleptics: 2,8-dihydroxy and 3,8-dihydroxy derivatives of 10-(4-methylpiperazino)-10,11-dihydrodibenzo[b,fJthiepin, Part CXXXIII in the series Neurotropic and Psychotropic Agents, Collection of Czechoslovak Chemical Communications, 1979, vol. 44, No. 10, pp. 2987-2996.
Protiva, Miroslav, et al., "Potential metabolites or tricyclic neuroleptics 3,7-dimethoxy and 7,8-dimethoxy derivatives of 10-{4-methylpiperazino )-10,11-dihydrodibenzo[b,f]thiepin", Collection of Czechoslovak Chemical Communications, 1981, vol. 46, pp. 1808-1817.
Shinji Okazaki et al., "New Trends of Photoresists", CMC Publishing Co., Ltd., Sep. 2009, p. 211-259.
Singh Ritesh and Panda Gautam, "Scandium triflate-catalyzed one-pot domino approach towards general and efficient syntheses of unsymmetrical 9-substituted xanthene derivatives," Organic & Biomolecular Chemistry, 2010, vol. 8, No. 5, pp. 1097-1105.
Sirkecioglu Okan et al., A Novel Synthesis of 14-(Hydroxymethylalkyl) Derivatives of Dibenzoxanthenes and 3,3-Dimethyl-4-(2-hydroxy-1-naphthyl)benzo[fJchroman, Journal of Heterocyclic Chemistry, Mar. 1, 1998, vol. 35, No. 2, pp. 457-460.
Sirringhaus Henning et al., Dibenzothienobisbenzothiophene—a novel fused-ring oligomer with high field-effect mobility, Journal of Materials Chemistry, 1999, vol. 9, pp. 2095-2101.
Skandinavisches Archiv fuer Physiologie, 43: 215-243 (1923).
Tian-jun Liu, Ke-shen Zhang, Yong-jun Chen, Dong Wang and Chao-jun Li, "Chiral Conjugated Oligomer Based on 1, 1'-Binol With 3, 3 ' -Acetylene-Phenylene-Acetylene Spacer", Chinese Journal of Polymer Science, Mar. 8, 2001, vol. 19, No. 5, p. 521-526.
U.S. Appl. No. 17/020,532, entitled "Compound, Resin, Resist Composition or Radiation-Sensitive Composition, Resist Pattern Formation Method, Method for Producing Amorphous Film, Underlayer Film Forming Material for Lithography, Composition for Underlayer Film Formation for Lithography, Method for Forming Circuit Pattern, and Purification Method," filed on Sep. 14, 2020, which is a division for U.S. Appl. No.15/759,076, filed Mar. 9, 2018, which entered the U.S. national phase from International Application No. PCT/JP2016/076392, filed on Sep. 8, 2016 Pursuant to 37 § 1.97(h).

* cited by examiner

MATERIAL FOR FORMING UNDERLAYER FILM FOR LITHOGRAPHY, COMPOSITION FOR FORMING UNDERLAYER FILM FOR LITHOGRAPHY, UNDERLAYER FILM FOR LITHOGRAPHY AND PRODUCTION METHOD THEREOF, AND RESIST PATTERN FORMING METHOD

CROSS-REFERENCE TO RELATED APPLICATIONS

This application is a U.S. national phase application filed under 35 U.S.C. § 371 of International Application PCT/JP2016/074865, filed on Aug. 25, 2016, designating the United States, which claims priority from Japanese Application Number 2015-170190, filed Aug. 31, 2015.

FIELD OF THE INVENTION

The present invention relates to a material for forming an underlayer film for lithography, a composition for forming an underlayer film for lithography, an underlayer film for lithography and a production method thereof, and a resist pattern forming method.

BACKGROUND OF THE INVENTION

Semiconductor devices are manufactured through microfabrication by lithography using a photoresist material, but are required to be made finer by a pattern rule in accordance with the increase in integration degree and the increase in speed of LSI in recent years. In lithography using exposure to light, which is currently used as a general-purpose technique, the resolution is now approaching the intrinsic limitation associated with the wavelength of the light source.

A light source for lithography, for use in forming a resist pattern, has a shorter wavelength from a KrF excimer laser (248 nm) to an ArF excimer laser (193 nm). However, as the resist pattern is made finer and finer, there arise a problem of resolution and a problem of collapse of the resist pattern after development, and therefore there is demanded for making a resist film thinner. Meanwhile, if the resist film is merely made thinner, it is difficult to achieve the resist pattern having a film thickness sufficient for processing a substrate. Accordingly, there is increasingly required a process in which not only the resist pattern but also a resist underlayer film is prepared between a resist and a semiconductor substrate to be processed and the resist underlayer film is allowed to have a function as a mask at the time of processing the substrate.

Currently, as the resist underlayer film for such a process, various ones are known. For example, as one for realizing a resist underlayer film for lithography, having a selection ratio of dry etching rate close to the resist, unlike a conventional resist underlayer film having a high etching rate, there has been proposed a material for forming an underlayer film for multilayer resist process, containing a resin component having at least a substituent which releases a terminal group to form a sulfonic acid residue when a predetermined energy is applied, and a solvent (see, for example, Patent Literature 1). In addition, as one for realizing a resist underlayer film for lithography, having a smaller selection ratio of dry etching rate than the resist, there has been proposed a resist underlayer film material including a polymer having a specified repeating unit (see, for example, Patent Literature 2). Furthermore, as one for realizing a resist underlayer film for lithography, having a smaller selection ratio of dry etching rate than the semiconductor substrate, there has been proposed a resist underlayer film material including a polymer formed by co-polymerizing a repeating unit of acenaphthylene, and a substituted or non-substituted repeating unit having a hydroxy group (see, for example, Patent Literature 3).

On the other hand, as a material for allowing such a resist underlayer film to have a high etching resistance, an amorphous carbon underlayer film is well known, which is formed by CVD using methane gas, ethane gas, acetylene gas, or the like as a raw material. However, there is demanded, in terms of process, a resist underlayer film material that can form a resist underlayer film in a wet process such as a spin coating method or screen printing.

In addition, as a material that is excellent in optical characteristics and etching resistance and that is capable of being dissolved in a solvent and being applied to a wet process, there has been proposed a composition for forming an underlayer film for lithography, which contains a naphthalene formaldehyde polymer including a specified constituent unit, and an organic solvent (see, for example, Patent Literatures 4 and 5).

Meanwhile, with respect to a forming method of an intermediate layer for use in forming a resist underlayer film in a three-layer process, for example, known are a forming method of a silicon nitride film (see, for example, Patent Literature 6), and a CVD forming method of a silicon nitride film (see, for example, Patent Literature 7). In addition, as an intermediate layer material for a three-layer process, known is a material containing a silsesquioxane-based silicon compound (see, for example, Patent Literatures 8 and 9).

CITATION LIST

Patent Literature

Patent Literature 1: Japanese Patent Laid-Open No. 2004-177668
Patent Literature 2: Japanese Patent Laid-Open No. 2004-271838
Patent Literature 3: Japanese Patent Laid-Open No. 2005-250434
Patent Literature 4: International Publication No. WO 2009/072465
Patent Literature 5: International Publication No. WO 2011/034062
Patent Literature 6: Japanese Patent Laid-Open No. 2002-334869
Patent Literature 7: International Publication No. WO 2004/066377
Patent Literature 8: Japanese Patent Laid-Open No. 2007-226170
Patent Literature 9: Japanese Patent Laid-Open No. 2007-226204

SUMMARY OF INVENTION

As described above, many materials for forming an underlayer film for lithography have been conventionally proposed, but there are no ones that not only have such a high solvent solubility as to be able to be applied to a wet process such as a spin coating method or screen printing, but also simultaneously satisfy heat resistance and etching resistance at a high level, and thus a new material is required to be developed.

The present invention has been then made in view of the above prior art problem, and an object thereof is to provide a material for forming an underlayer film for lithography, which can be applied to a wet process and which is useful for forming a photoresist underlayer film excellent in heat resistance and etching resistance.

The present inventors have intensively studied to solve the above prior art problem, and as a result, have found that a photoresist underlayer film excellent in heat resistance and etching resistance is obtained by using a material for forming an underlayer film, containing a compound or a resin having a specified structure, thereby leading to the completion of the present invention. That is, the present invention is as follows.

[1]

A material for forming an underlayer film for lithography, comprising at least any of a compound represented by following formula (1) or a resin comprising a structural unit derived from a compound represented by the following formula (1),

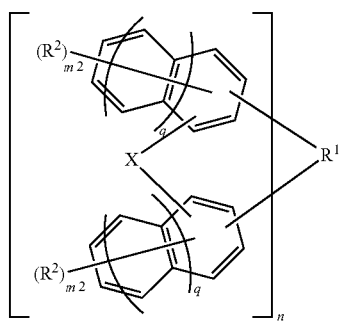

wherein $R^1$ represents a 2n-valent group having a 1 to 60 carbon atoms, or a single bond, each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, or a hydroxyl group, and may be the same or different in the same naphthalene ring or benzene ring, n is an integer of 1 to 4, structural formulae of n's structural units in square brackets [ ] may be the same or different when n is an integer of 2 or more, X represents an oxygen atom, a sulfur atom, or a non-bridging group, each $m^2$ is independently an integer of 0 to 7, in which at least one $m^2$ is an integer of 1 to 7, and each q is independently 0 or 1, provided that at least one selected from the group consisting of $R^1$ and $R^2$ is a group having an iodine atom.

[2]

The material for forming the underlayer film for lithography according to [1], wherein the compound represented by the formula (1) is a compound represented by following formula (1-1),

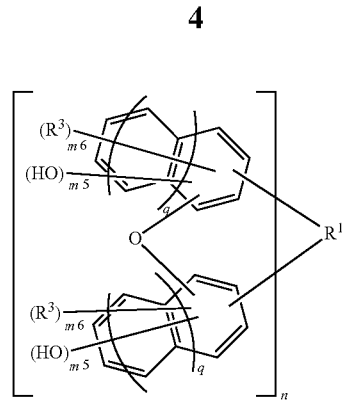

wherein $R^1$, n and q are the same as defined above, each $R^3$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, or a thiol group, and may be the same or different in the same naphthalene ring or benzene ring, each $m^5$ is independently an integer of 1 to 6, each $m^6$ is independently an integer of 0 to 5, and $m^5+m^6$ is an integer of 1 to 6, provided that at least one selected from the group consisting of $R^1$ and $R^3$ is a group having an iodine atom.

[3]

The material for forming the underlayer film for lithography according to [2], wherein the compound represented by the formula (1-1) is a compound represented by following formula (1-2),

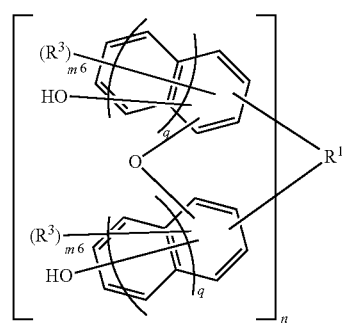

wherein $R^1$, $R^3$, m, n and q are the same as defined above, and at least one selected from the group consisting of $R^1$ and $R^3$ is a group having an iodine atom.

[4]

The material for forming the underlayer film for lithography according to [3], wherein the compound represented by formula (1-2) is a compound represented by following formula (1-3),

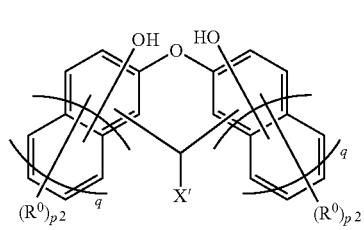

wherein q is the same as defined above, X' represents a hydrogen atom, a halogen atom, or a monovalent group having 1 to 59 carbon atoms, each $R^0$ independently represents an alkyl group having 1 to 4 carbon atoms, or a halogen atom, and may be the same or different in the same naphthalene ring or benzene ring, and each $p^2$ is independently an integer of 0 to 5, provided that at least one selected from the group consisting of X' and $R^0$ is a group having an iodine atom.

[5]

The material for forming the underlayer film for lithography according to [4], wherein the compound represented by the formula (1-3) is a compound represented by following formula (1-4),

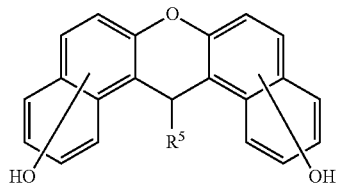

(1-4)

wherein $R^5$ represents an iodine atom, or a monovalent group selected from a straight, branched or cyclic alkyl group having an iodine atom and having 1 to 10 carbon atoms, an aryl group having an iodine atom and having 6 to 10 carbon atoms, a heterocyclic group having an iodine atom and having 6 to 10 carbon atoms, an alkenyl group including an iodine atom and having 2 to 10 carbon atoms, and an alkoxy group having an iodine atom and having 1 to 30 carbon atoms.

[6]

The material for forming the underlayer film for lithography according to [5], wherein the compound represented by the formula (1-4) is a compound represented by following formula (1-5) or following formula (1-6),

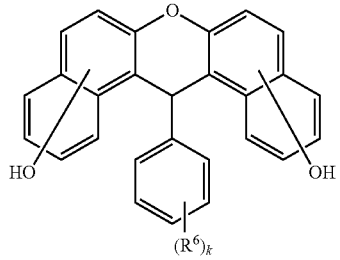

(1-5)

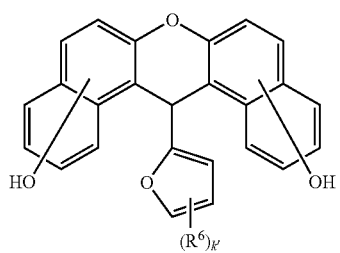

(1-6)

wherein $R^6$ represents at least one selected from the group consisting of a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group and a hydroxy group; and k is an integer of 1 to 5 and k' is an integer of 1 to 3, provided that at least one $R^6$ represents a monovalent group having an iodine atom.

[7]

The material for forming the underlayer film for lithography according to [6], wherein the compound represented by the formula (1-5) or the formula (1-6) is at least one selected from the group consisting of following compounds.

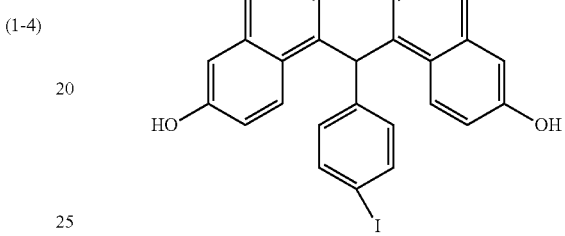

(A-2)

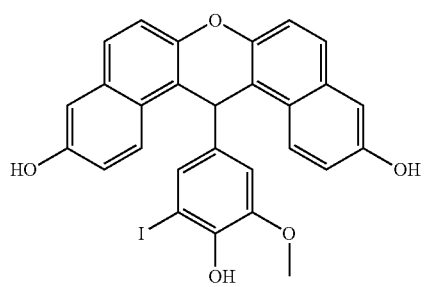

(A-3)

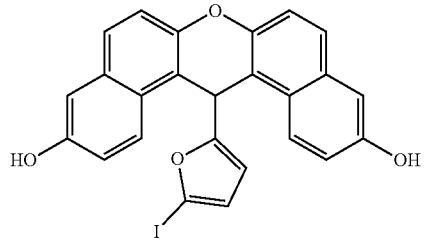

(A-4)

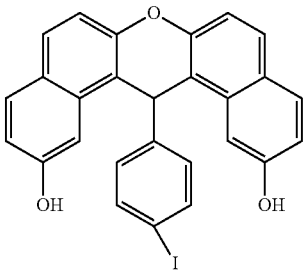

(B-2)

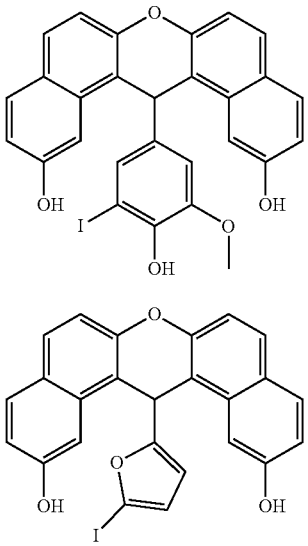

(B-3)

(B-4)

[8]
A composition for forming an underlayer film for lithography, comprising the material for forming the underlayer film for lithography according to any of [1] to [7], and a solvent.

[9]
The composition for forming the underlayer film for lithography according to [8], further comprising an acid generator.

[10]
The composition for forming the underlayer film for lithography according to [8] or [9], further comprising a crosslinking agent.

[11]
An underlayer film for lithography, formed from the composition for forming the underlayer film for lithography according to any of [8] to [10].

[12]
A method for producing an underlayer film for lithography, comprising a step of forming an underlayer film on a substrate by using the composition for forming the underlayer film for lithography according to any of [8] to [10].

[13]
A resist pattern forming method comprising:
a step of forming an underlayer film on a substrate by using the composition for forming the underlayer film according to any of [8] to [10];
a step of forming at least one photoresist layer on the underlayer film; and
a step of irradiating a predetermined region of the photoresist layer with radiation, and developing it.

The material for forming an underlayer film for lithography of the present invention can be applied to a wet process and enables a photoresist underlayer film excellent in heat resistance and etching resistance to be formed.

DESCRIPTION OF EMBODIMENTS

Hereinafter, an embodiment (hereinafter, referred to as "the present embodiment") of the present invention will be described. It is to be noted that the following present embodiments are illustrative for describing the present invention, and the present invention is not limited only to such embodiments.

[Material for Forming Underlayer Film for Lithography]

A material for forming an underlayer film for lithography of the present embodiment contains at least any of a compound represented by the following formula (1) or a resin including a structural unit derived from a compound represented by the following formula (1).

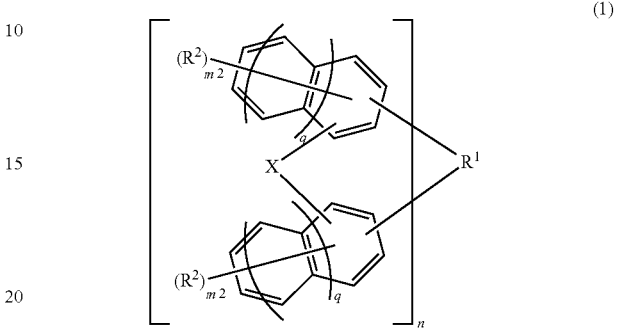

(1)

(in formula (1), $R^1$ represents a 2n-valent group having a 1 to 60 carbon atoms, or a single bond, each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, or a hydroxyl group, and may be the same or different in the same naphthalene ring or benzene ring, n is an integer of 1 to 4, structural formulae of n's structural units in square brackets [ ] may be the same or different when n is an integer of 2 or more, X represents an oxygen atom, a sulfur atom, or a non-bridging group, each $m^2$ is independently an integer of 0 to 7, in which at least one $m^2$ is an integer of 1 to 7, and each q is independently 0 or 1, provided that at least one selected from the group consisting of $R^1$ and $R^2$ is a group having an iodine atom.)

In the formula (1), X represents an oxygen atom, a sulfur atom, or a non-bridging group. Respective aromatic rings are bonded at any position via X.

$R^1$ represents a 2n-valent group having a 1 to 60 carbon atoms, or a single bond, and respective aromatic rings are bonded at any position via $R^1$. The 2n-valent group means, for example, an alkylene group having 1 to 60 carbon atoms when n=1, an alkanetetrayl group having 1 to 60 carbon atoms when n=2, an alkanehexayl group having 2 to 60 carbon atoms when n=3, and an alkaneoctayl group having 3 to 60 carbon atoms when n=4. In addition, the 2n-valent group is not particularly limited, and examples thereof include those having a straight hydrocarbon group, a branched hydrocarbon group or an alicyclic hydrocarbon group. Herein, the alicyclic hydrocarbon group also includes a bridged alicyclic hydrocarbon group.

The 2n-valent group may also have a double bond, a hetero atom, or an aromatic group having 6 to 30 carbon atoms. Furthermore, the aromatic group may also have a cyano group, a nitro group, a heterocyclic group, a halogen atom, a straight hydrocarbon group having 1 to 20 carbon atoms, a branched hydrocarbon group having 3 to 20 carbon atoms, a cyclic hydrocarbon group having 3 to 20 carbon atoms, an aryl group having 6 to 20 carbon atoms, an alkenyl group having 2 to 10 carbon atoms, an alkoxy group having 1 to 30 carbon atoms, a thiol group, or a hydroxyl group.

Each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, or a hydroxyl group, and may be the same or different in the same naphthalene ring or benzene ring.

n is an integer of 1 to 4, and structural formulae of n's structural units in square brackets [ ] may be the same or different when n is an integer of 2 or more. Each $m^2$ is independently an integer of 0 to 7, provided that at least one $m^2$ is an integer of 1 to 7. Each q is independently 0 or 1.

In addition, in the formula (1), at least one selected from the group consisting of $R^1$ and $R^2$ is a group having an iodine atom. Herein, the phrase "at least one selected from the group consisting of $R^1$ and $R^2$" means "at least one group selected from the group consisting of $R^1$ and $R^2$", and does not means "at least one kind of a group selected from the group consisting of $R^1$ and $R^2$".

The group having an iodine atom, with respect to $R^1$, is not particularly limited, and examples thereof include a straight hydrocarbon group having 1 to 60 carbon atoms substituted with an iodine atom, a branched hydrocarbon group having 3 to 60 carbon atoms substituted with an iodine atom, an alicyclic hydrocarbon group having 3 to 60 carbon atoms substituted with an iodine atom, an aromatic group having 6 to 60 carbon atoms substituted with an iodine atom, or a group having an aromatic group having 6 to 60 carbon atoms substituted with an iodine atom. A branched hydrocarbon group having 3 to 60 carbon atoms substituted with an iodine atom, an alicyclic hydrocarbon group having 3 to 60 carbon atoms substituted with an iodine atom, an aromatic group having 6 to 60 carbon atoms substituted with an iodine atom, or a group having an aromatic group having 6 to 60 carbon atoms substituted with an iodine atom, is preferable, an alicyclic hydrocarbon group having 3 to 60 carbon atoms substituted with an iodine atom, an aromatic group having 6 to 60 carbon atoms substituted with an iodine atom, or a group having an aromatic group having 6 to 60 carbon atoms substituted with an iodine atom, is more preferable, and a group having an aromatic group having 6 to 60 carbon atoms substituted with an iodine atom, is further preferable, in terms of heat resistance.

The group having an iodine atom, with respect to $R^2$, is not particularly limited, and examples thereof include an iodine atom, a straight hydrocarbon group having 1 to 6 carbon atoms substituted with an iodine atom, a branched hydrocarbon group having 3 to 6 carbon atoms substituted with an iodine atom, a cyclic hydrocarbon group having 3 to 6 carbon atoms substituted with an iodine atom, or an aryl group having 6 carbon atoms substituted with an iodine atom. The group having an iodine atom is preferably an iodine atom, a straight hydrocarbon group having 1 to 6 carbon atoms substituted with an iodine atom, or a branched hydrocarbon group having 3 to 6 carbon atoms substituted with an iodine atom, more preferably an iodine atom, or a straight hydrocarbon group having 1 to 6 carbon atoms substituted with an iodine atom, further preferably an iodine atom, in terms of solubility in a safe solvent, and the like.

The compound represented by the formula (1) has a high heat resistance due to rigidity of its structure while having a relatively low molecular weight, and therefore it can be used even under a high-temperature baking condition. In addition, the compound has a relatively low molecular weight and a low viscosity, and therefore, even when being applied to a substrate having a step (in particular, fine space, hole pattern and the like), it can be easily filled uniformly in every part of the step. As a result, a material for forming an underlayer film for lithography using such a compound can be improved in terms of embedding properties in a relatively advantageous manner. In addition, the compound has a relatively high carbon concentration to thereby impart also a high etching resistance.

The compound represented by the formula (1) is preferably a compound where X represents an oxygen atom in terms of feeding property of raw materials, more preferably a compound represented by the following formula (1-1) in terms of solubility in an organic solvent.

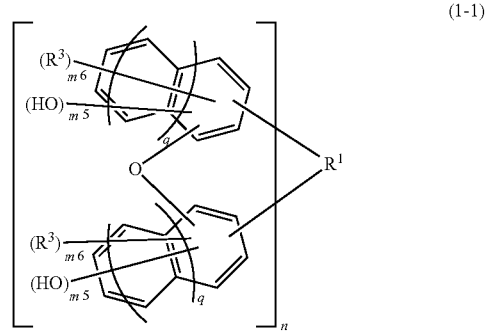

(1-1)

In the formula (1-1), $R^1$, n and q are the same as defined in the formula (1). Each $R^3$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, or a thiol group, and may be the same or different in the same naphthalene ring or benzene ring. Each $m^5$ is independently an integer of 1 to 6, each $m^6$ is independently an integer of 0 to 5, and $m^5+m^6$ is an integer of 1 to 6, provided that at least one selected from the group consisting of $R^1$ and $R^3$ is a group having an iodine atom.

In addition, the compound represented by the formula (1-1) is further preferably a compound represented by the following formula (1-2) in terms of solubility.

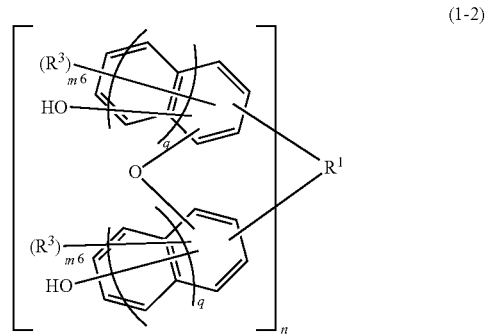

(1-2)

In the formula (1-2), $R^1$, $R^3$, $m^6$, n and q are the same as defined in the formula (1-1), provided that at least one selected from the group consisting of $R^1$ and $R^3$ is a group having an iodine atom.

In addition, the compound represented by formula (1-2) is preferably a compound where n=1, specifically, for example, preferably a compound represented by the following formula (1-3) because such compounds have a low molecular weight.

(1-3)

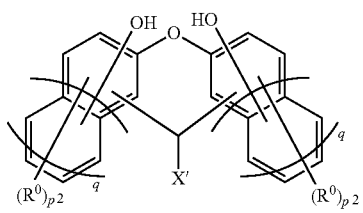

In the formula (1-3), q is the same as defined above. X' represents a hydrogen atom, a halogen atom, or a monovalent group having 1 to 59 carbon atoms. Each R0 independently represents an alkyl group having 1 to 4 carbon atoms, or a halogen atom, and may be the same or different in the same naphthalene ring or benzene ring. Each $p^2$ is independently an integer of 0 to 5, provided that at least one selected from the group consisting of X' and $R^0$ is a group having an iodine atom.

In addition, the compound represented by the formula (1-3) is further more preferably a compound represented by the following formula (1-4) in terms of heat resistance.

(1-4)

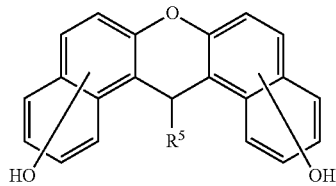

In the formula (1-4), $R^5$ represents an iodine atom, or a monovalent group selected from a straight, branched or cyclic alkyl group having an iodine atom and having 1 to 10 carbon atoms, an aryl group having an iodine atom and having 6 to 10 carbon atoms, a heterocyclic group having an iodine atom and having 6 to 10 carbon atoms, an alkenyl group having an iodine atom and having 2 to 10 carbon atoms, and an alkoxy group having an iodine atom and having 1 to 30 carbon atoms.

Furthermore, the compound represented by the formula (1-4) is further more preferably a compound represented by the following formula (1-5) or the following formula (1-6). Such a xanthene compound can provide a material for forming an underlayer film for lithography, which is higher in the solubility in a high safe solvent and better in preservation stability and thin film formation, and which can impart a good pattern shape.

(1-5)

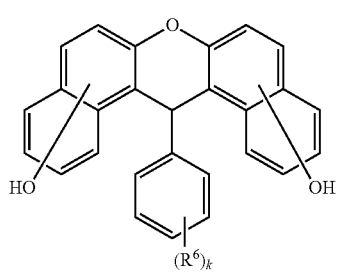

(1-6)

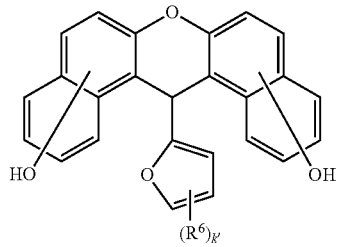

In the formula (1-5) and the formula (1-6), $R^6$ represents at least one selected from the group consisting of a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group and a hydroxy group. k is an integer of 1 to 5 and k' is an integer of 1 to 3, provided that at least one $R^6$ represents a monovalent group having an iodine atom.

Hereinafter, specific examples of the compound represented by the formula (1) are recited, but the compound represented by the formula (1) is not limited to such specific examples recited herein.

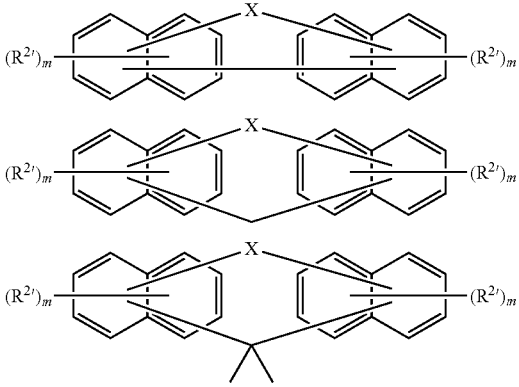

In the above formulae, X is the same as defined in the formula (1), $R^{2'}$ is the same as $R^2$ defined in the formula (1), and each m is independently an integer of 1 to 6, provided that at least one $R^{2'}$ represents a monovalent group having an iodine atom.

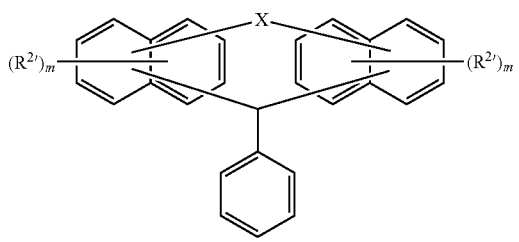

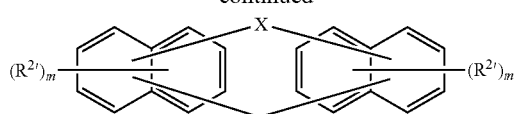
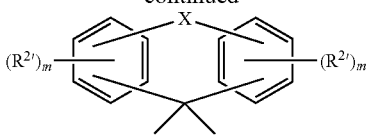
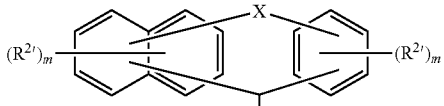
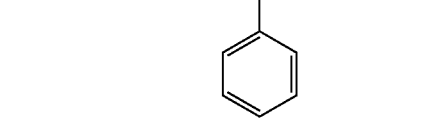
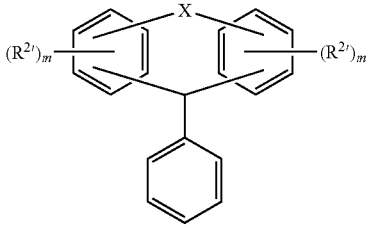
In the above formulae, X is the same as defined in the formula (1), R$^{2'}$ is the same as R$^2$ defined in the formula (1), and each m is independently an integer of 1 to 6, provided that at least one R$^{2'}$ represents a monovalent group having an iodine atom.
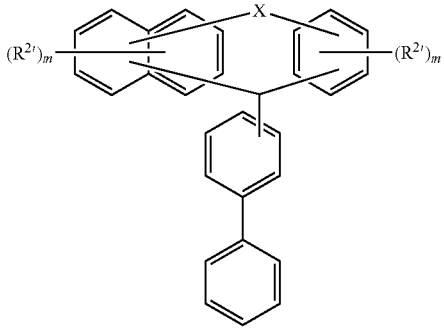
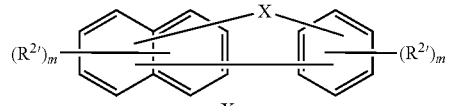
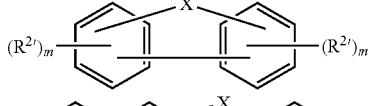
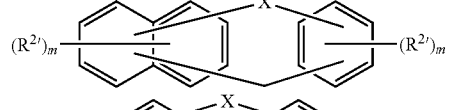
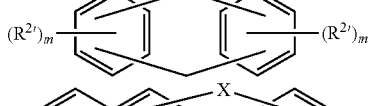
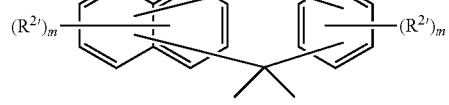
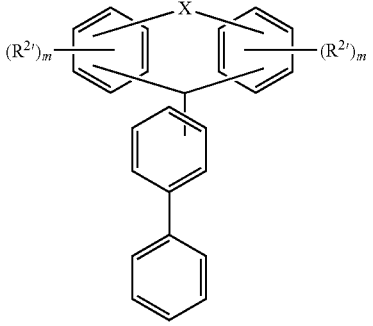
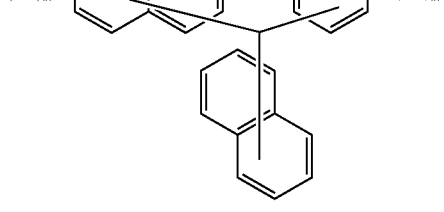

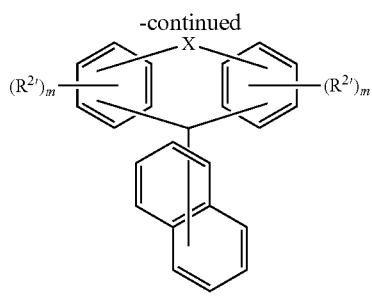
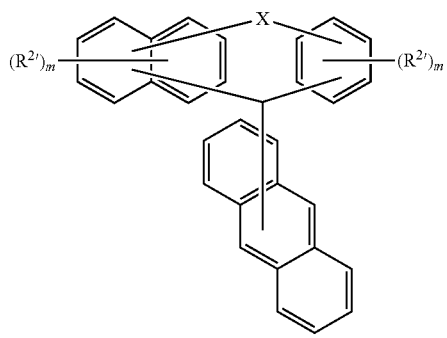
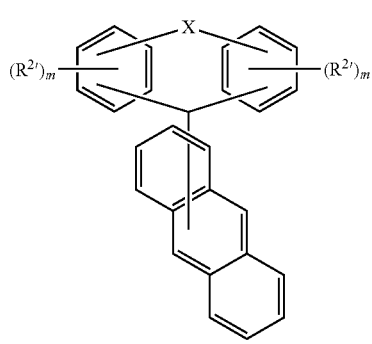
In the above formulae, X is the same as defined in the formula (1), $R^{2'}$ is the same as $R^2$ defined in the formula (1), and each m is independently an integer of 1 to 4.
Provided that at least one $R^{2'}$ represents a monovalent group having an iodine atom.
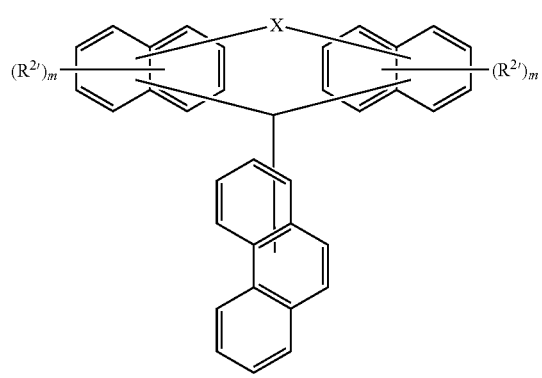
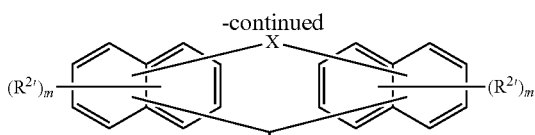
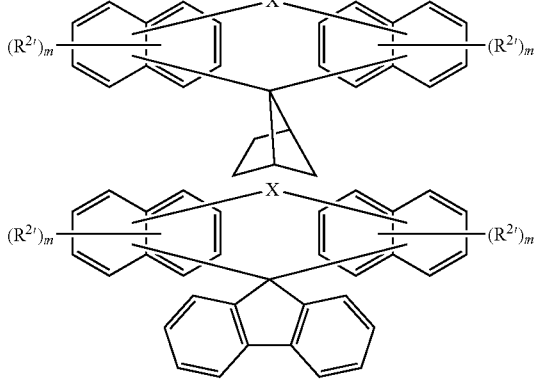

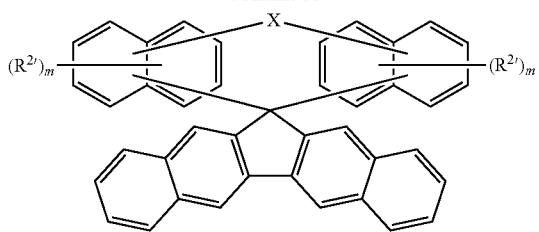
In the above formulae, X is the same as defined in the formula (1), $R^{2'}$ is the same as $R^2$ defined in the formula (1), and each m is independently an integer of 1 to 6.
Provided that at least one $R^{2'}$ represents a monovalent group having an iodine atom.
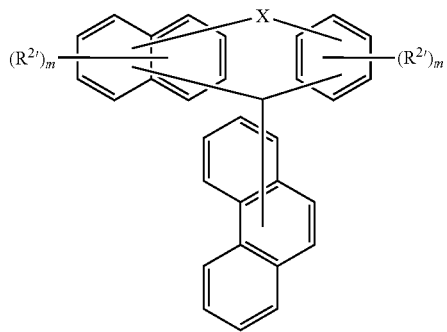
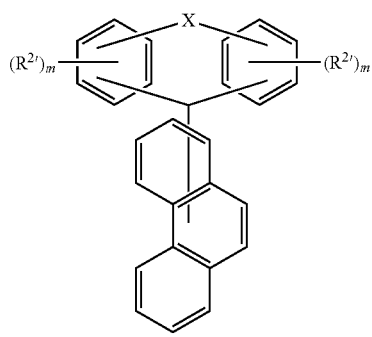
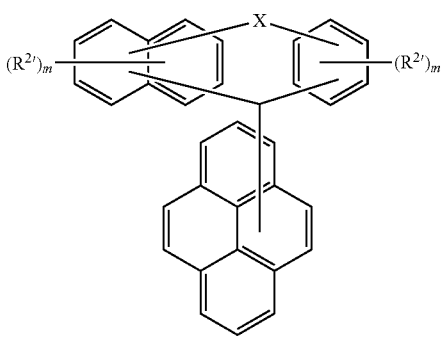
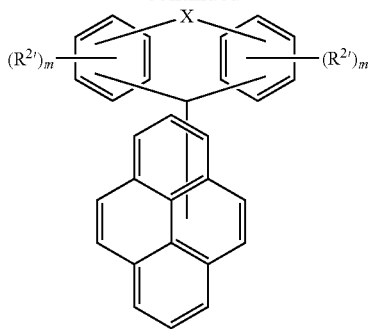
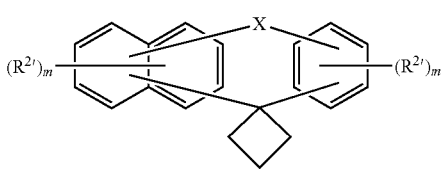
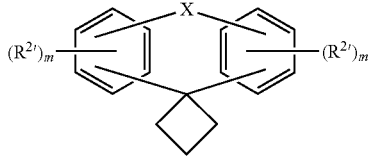
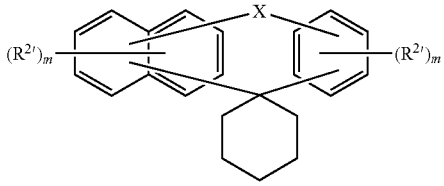
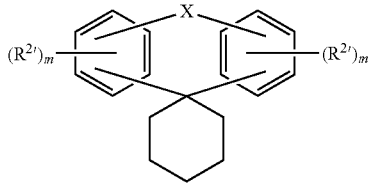
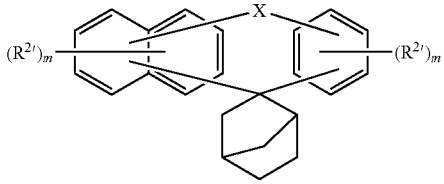
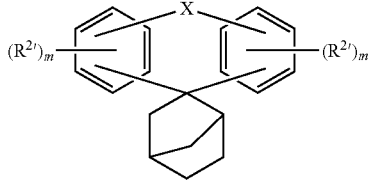
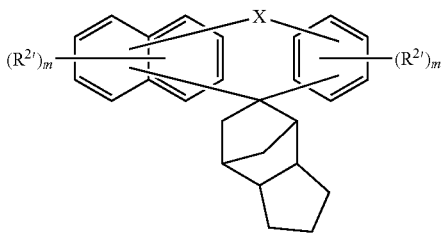
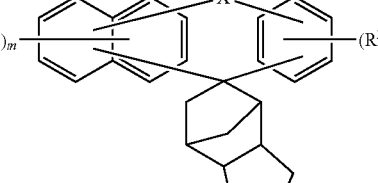

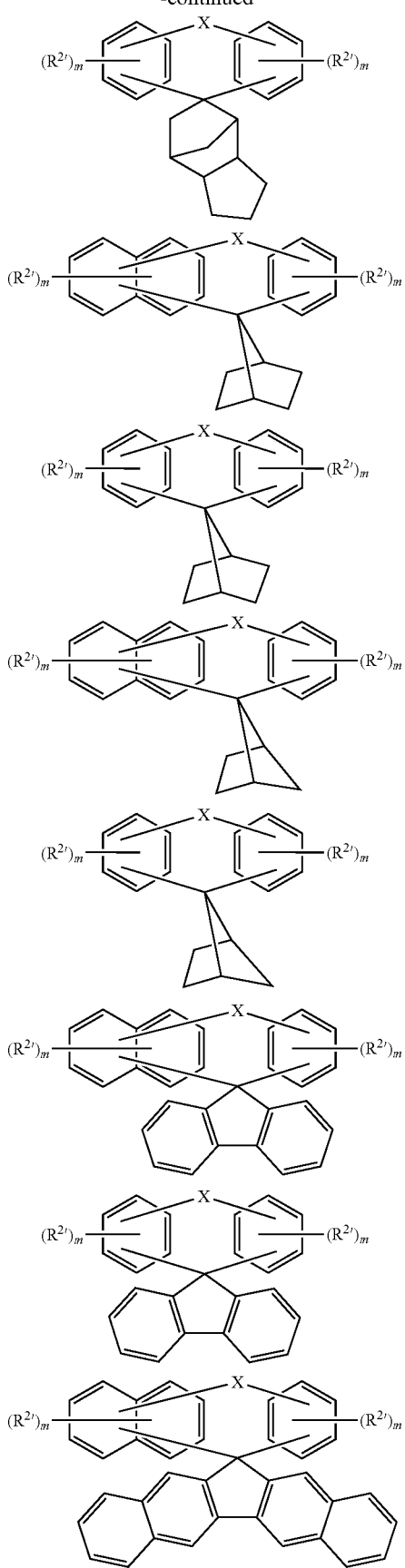
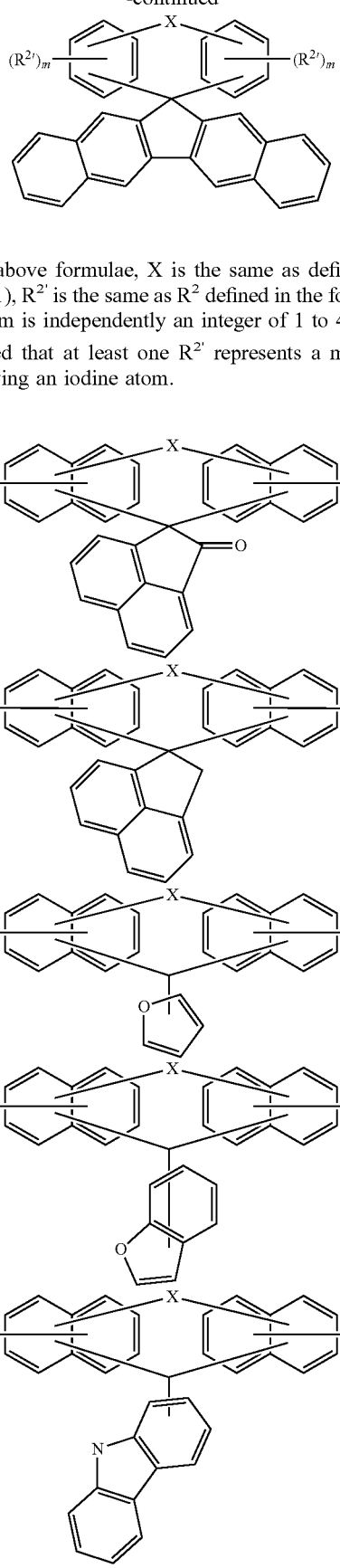
In the above formulae, X is the same as defined in the formula (1), $R^{2'}$ is the same as $R^2$ defined in the formula (1), and each m is independently an integer of 1 to 4.
Provided that at least one $R^{2'}$ represents a monovalent group having an iodine atom.

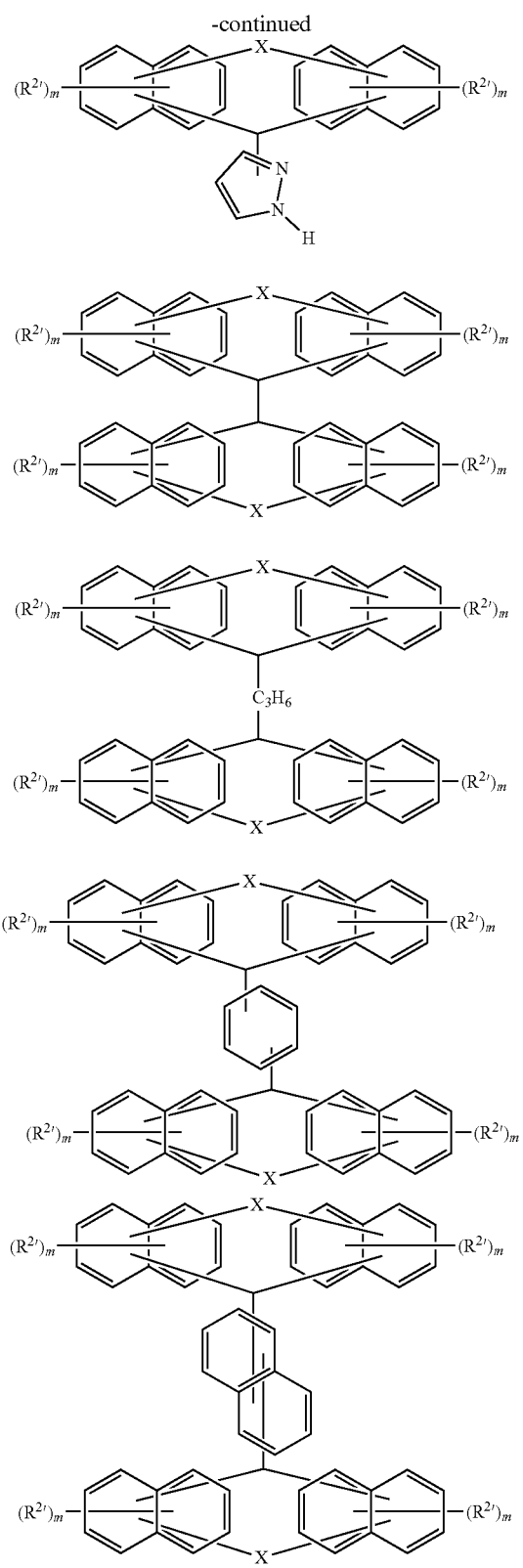
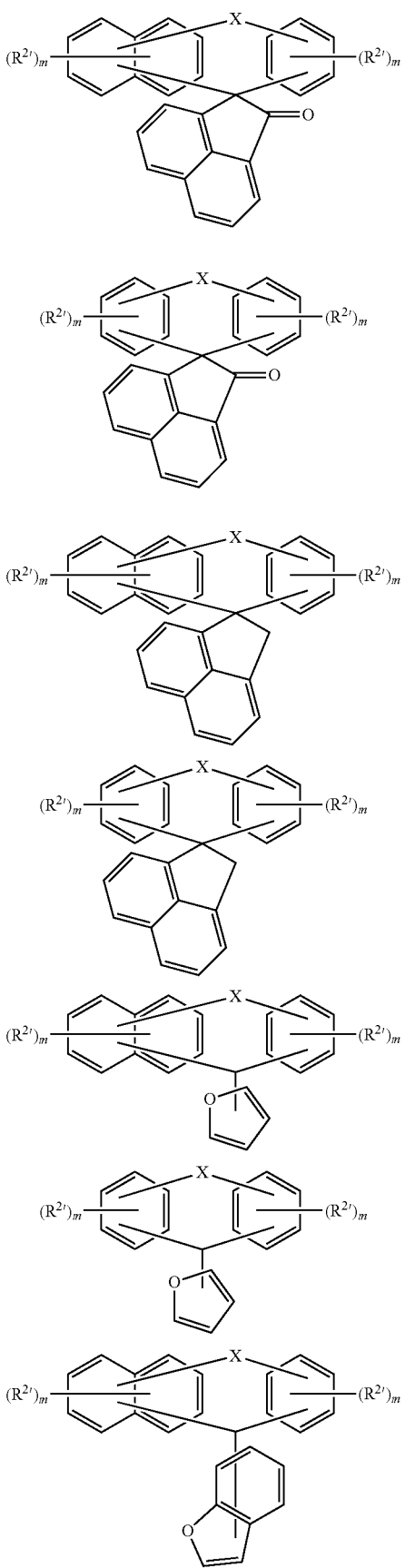
In the above formulae, X is the same as defined in the formula (1), $R^{2'}$ is the same as $R^2$ defined in the formula (1), and each m is independently an integer of 1 to 6, provided that at least one $R^{2'}$ represents a monovalent group having an iodine atom.

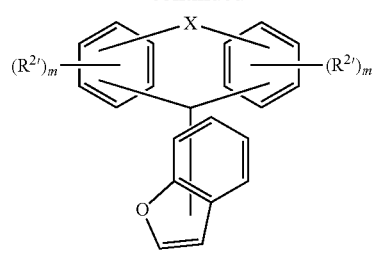
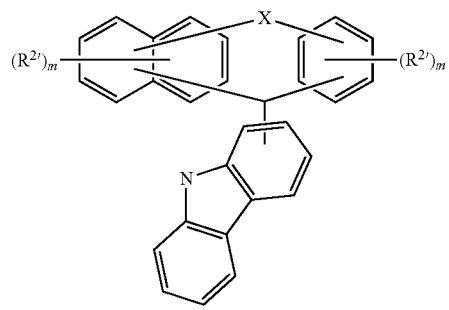
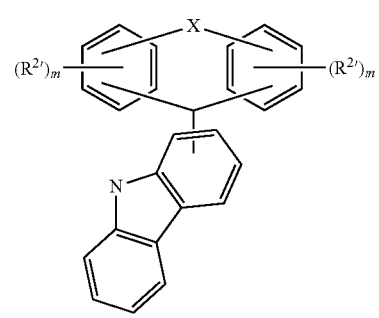
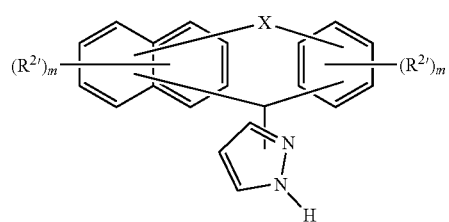
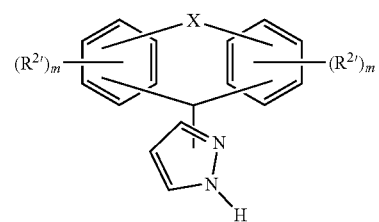
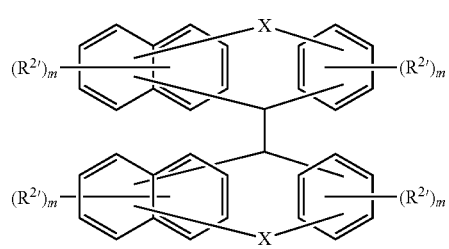
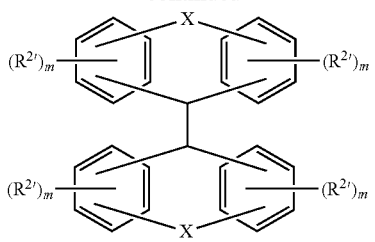
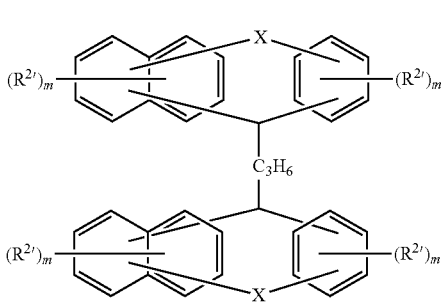
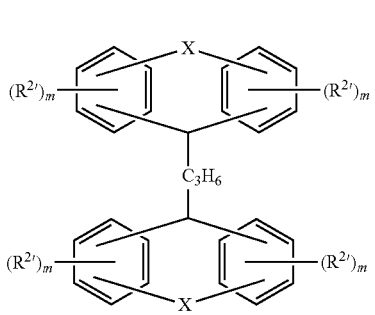
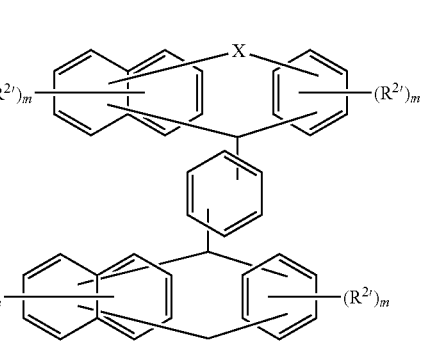
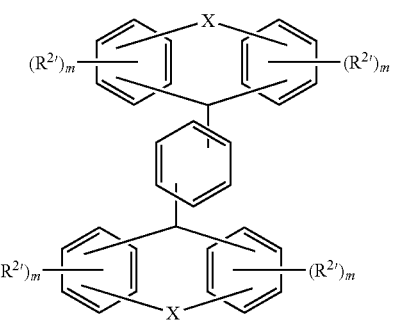

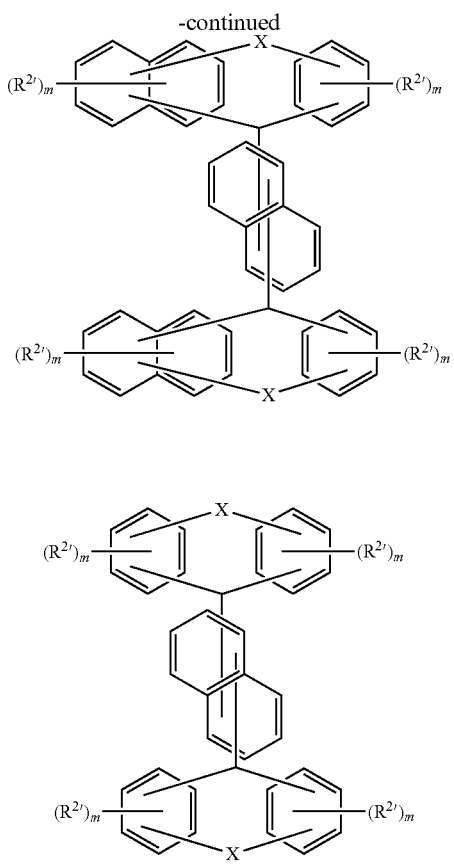

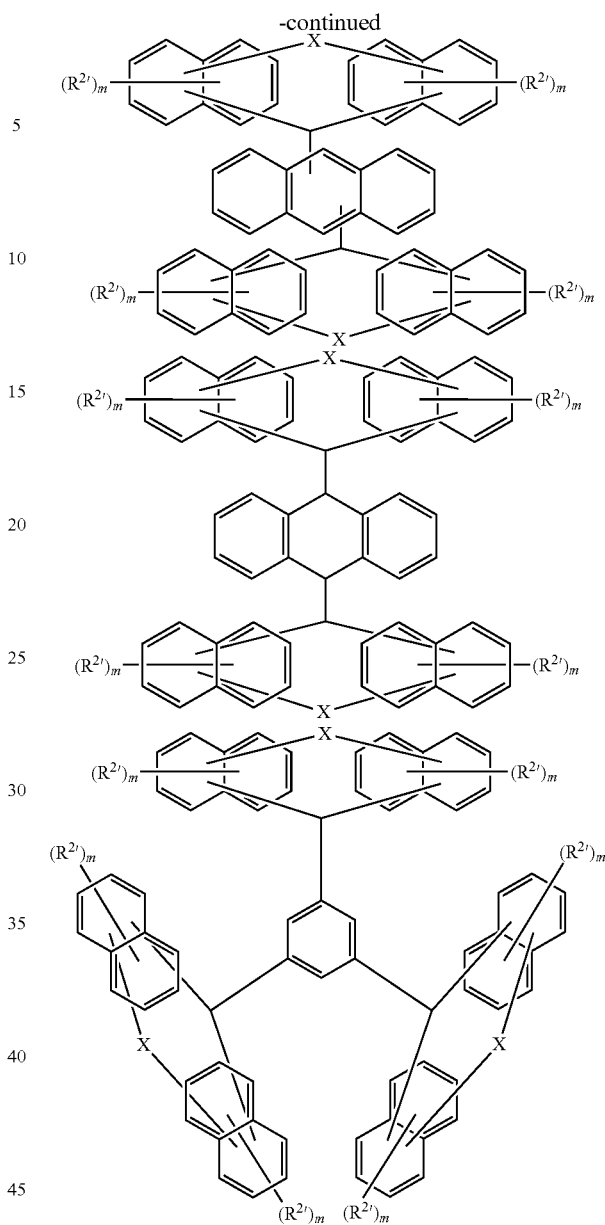

In the above formulae, X is the same as defined in the formula (1), R$^{2'}$ is the same as R$^2$ defined in the formula (1), and m is independently an integer of 1 to 4.

Provided that at least one R$^{2'}$ represents a monovalent group having an iodine atom.

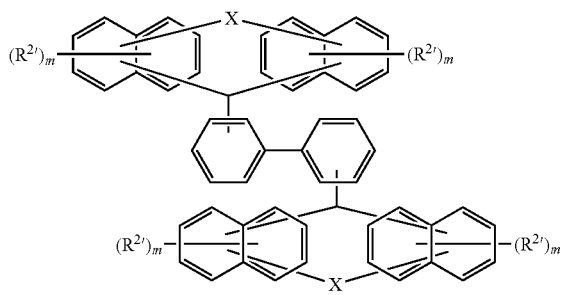

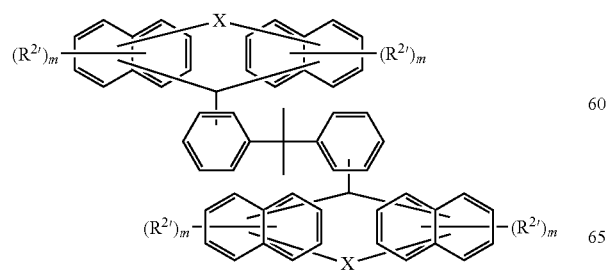

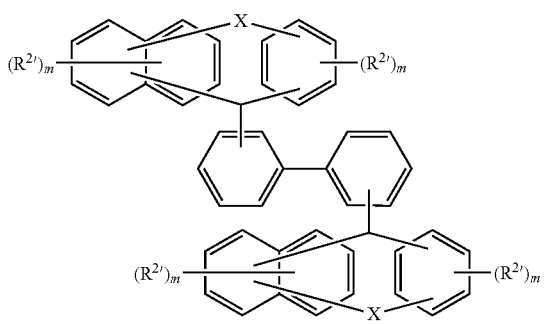

In the above formulae, X is the same as defined in the formula (1), R$^{2'}$ is the same as R$^2$ defined in the formula (1), and each m is independently an integer of 1 to 6, provided that at least one R$^{2'}$ represents a monovalent group having an iodine atom.

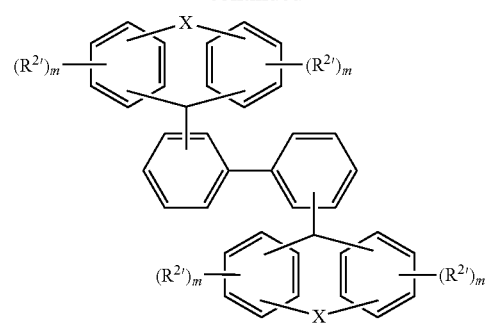
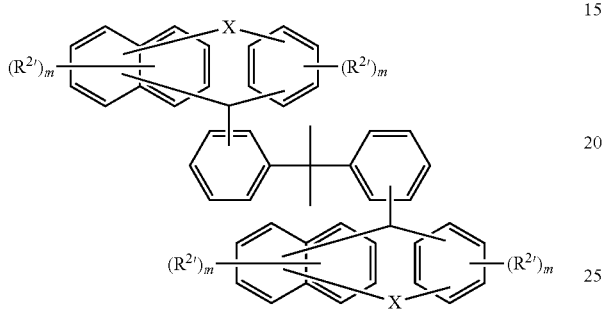
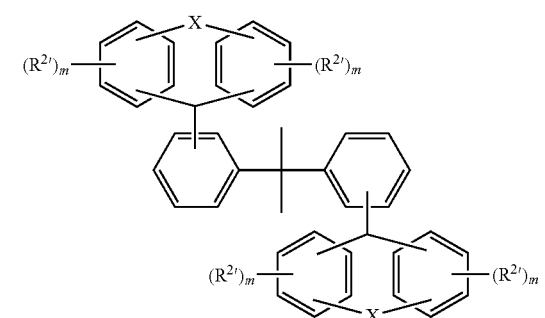
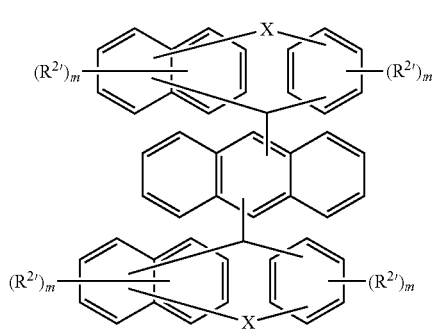
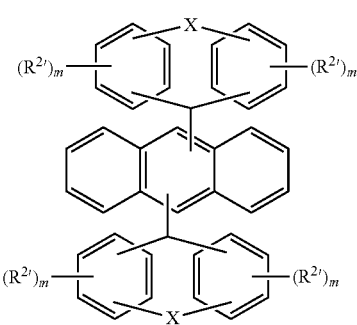

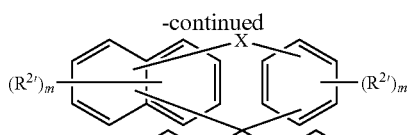
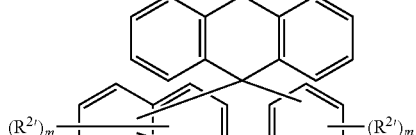
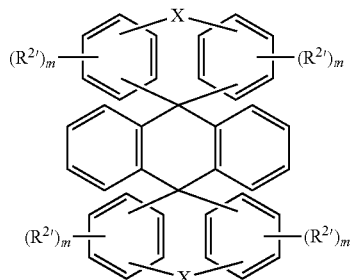
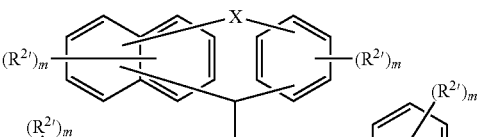
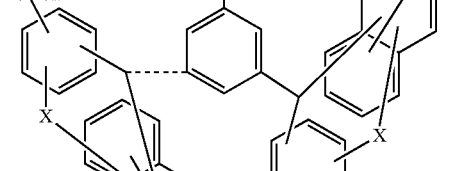
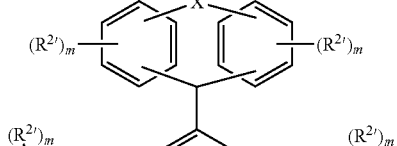
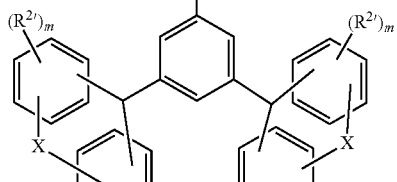
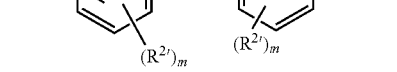
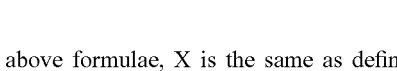
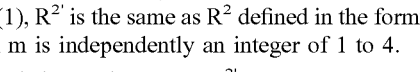

In the above formulae, X is the same as defined in the formula (1), $R^{2'}$ is the same as $R^2$ defined in the formula (1), and each m is independently an integer of 1 to 4.

Provided that at least one $R^{2'}$ represents a monovalent group having an iodine atom.

Hereinafter, specific examples of the compound represented by the formula (1) are further recited, but are not limited to those recited herein.

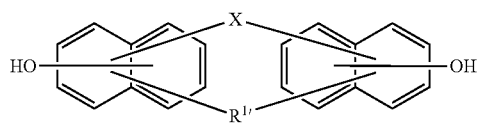
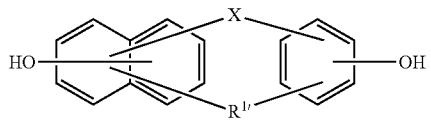
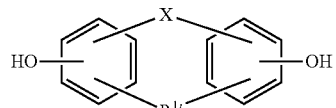
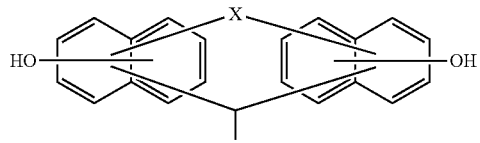
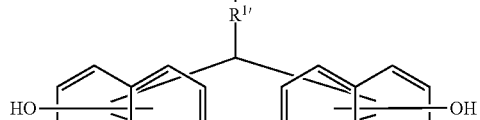
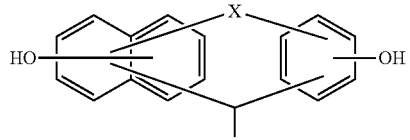
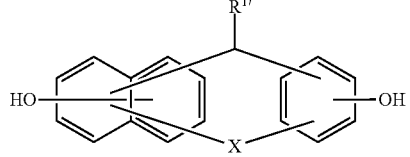
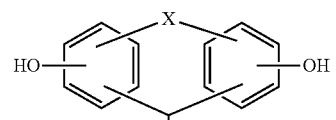
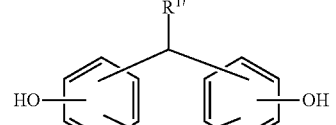

In the above formulae, X is the same as defined in the formula (1), and $R^{1'}$ is the same as $R^1$ defined in the formula (1), provided that $R^{1'}$ represents a divalent group having an iodine atom.

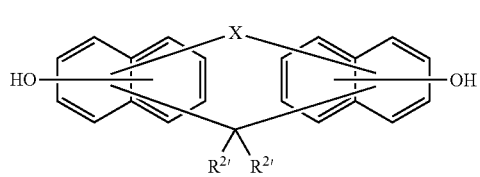

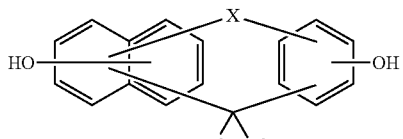

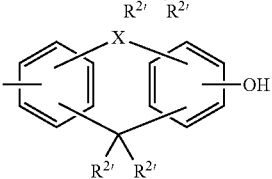

In the above formulae, X is the same as defined in the formula (1), and $R^{2'}$ is the same as $R^2$ defined in the formula (1), provided that at least one $R^{2'}$ represents a monovalent group having an iodine atom.

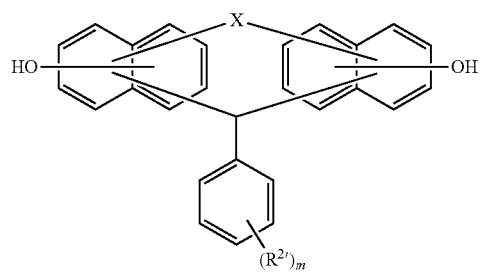

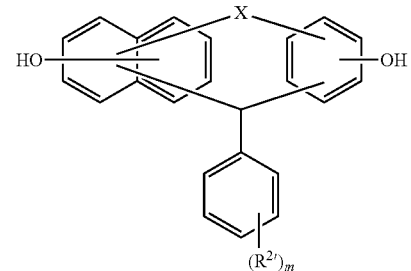

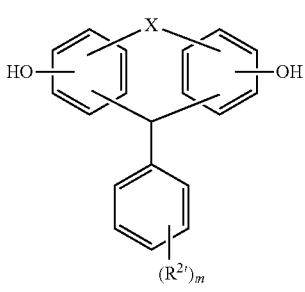

In the above formulae, X is the same as defined in the formula (1), $R^{2'}$ is the same as $R^2$ defined in the formula (1), and m is an integer of 1 to 5, provided that at least one $R^{2'}$ represents a monovalent group having an iodine atom.

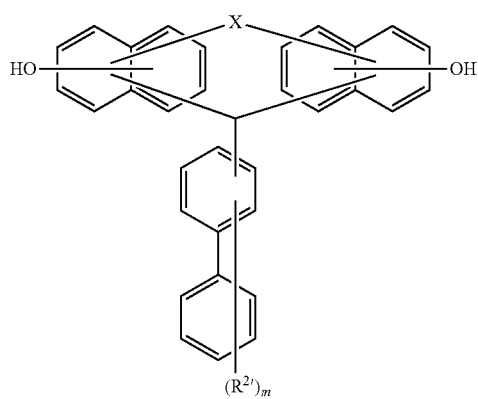

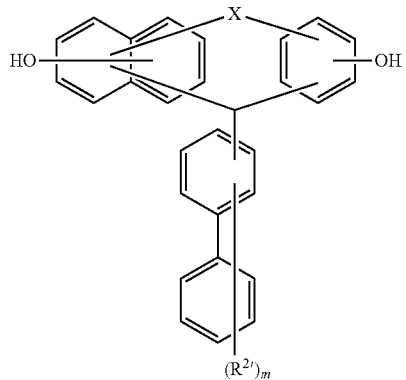

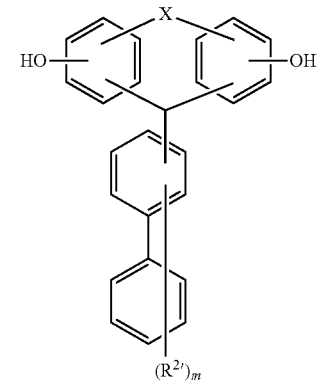

In the above formulae, X is the same as defined in the formula (1), $R^{2'}$ is the same as $R^2$ defined in the formula (1), and m is an integer of 1 to 9, provided that at least one $R^{2'}$ represents a monovalent group having an iodine atom.

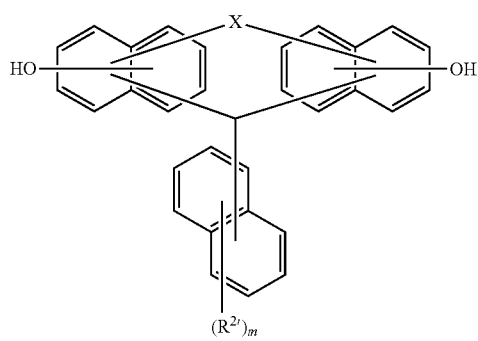

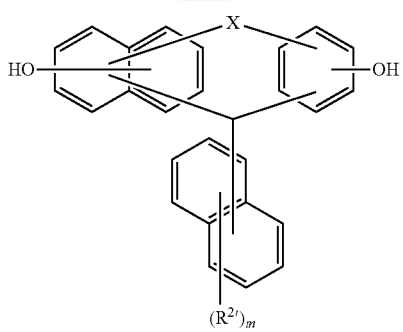

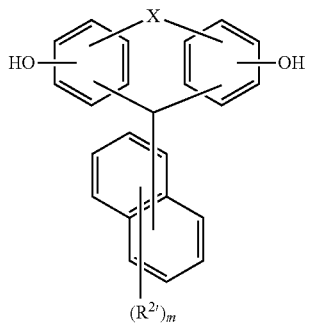

In the above formulae, X is the same as defined in the formula (1), $R^{2'}$ is the same as $R^2$ defined in the formula (1), and m is an integer of 1 to 7, provided that at least one $R^{2'}$ represents a monovalent group having an iodine atom.

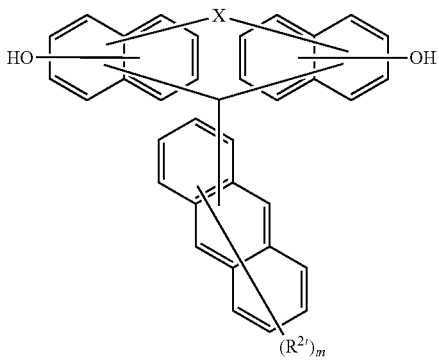

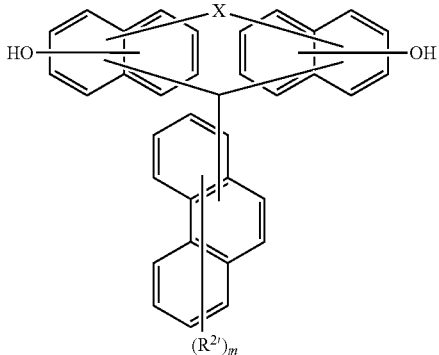

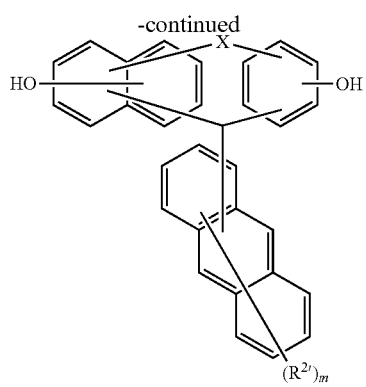

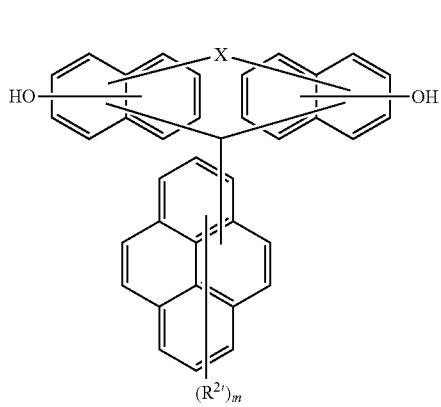

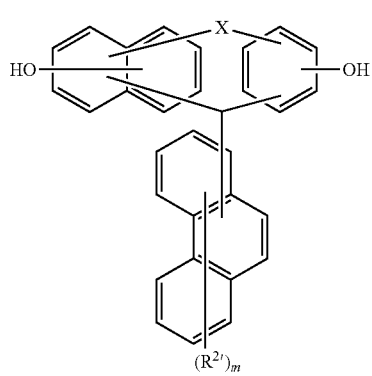

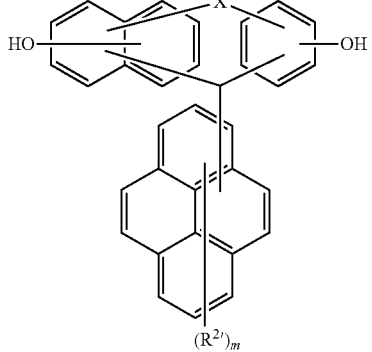

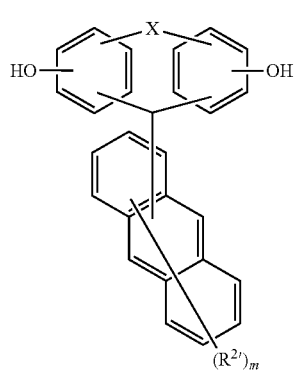

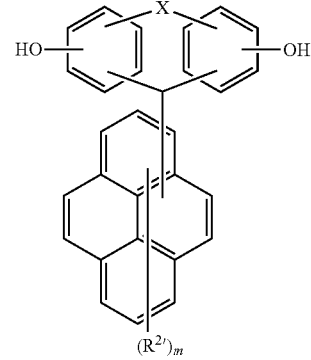

In the above formulae, X is the same as defined in the formula (1), R$^{2'}$ is the same as R$^2$ defined in the formula (1), and m is an integer of 1 to 9, provided that at least one R$^{2'}$ represents a monovalent group having an iodine atom.

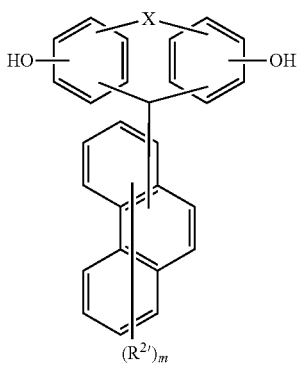

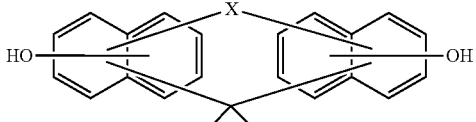

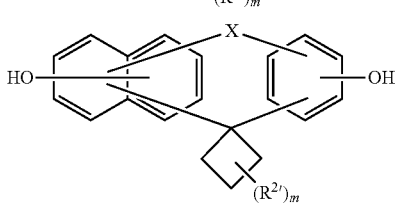

In the above formulae, X is the same as defined in the formula (1), R$^{2'}$ is the same as R$^2$ defined in the formula (1), and m is an integer of 1 to 9, provided that at least one R$^{2'}$ represents a monovalent group having an iodine atom.

-continued

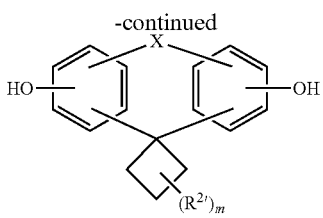

In the above formulae, X is the same as defined in the formula (1), R²' is the same as R² defined in the formula (1), and m is an integer of 1 to 6, provided that at least one R²' represents a monovalent group having an iodine atom.

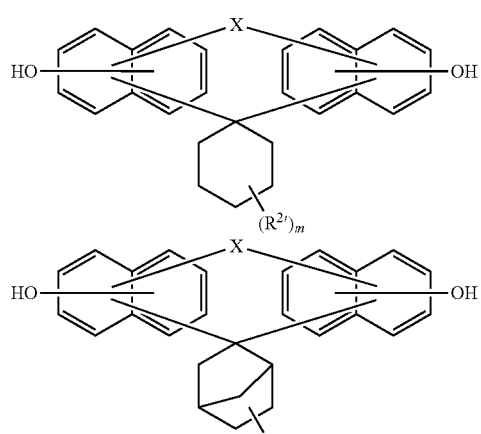

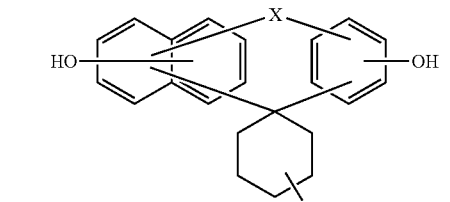

-continued

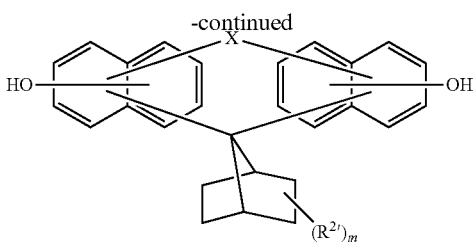

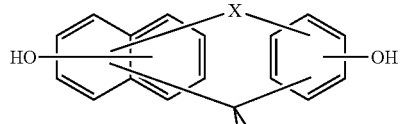

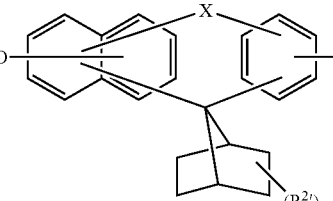

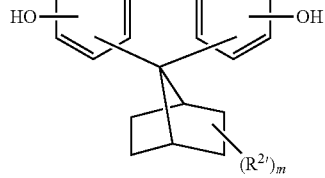

In the above formulae, X is the same as defined in the formula (1), R²' is the same as R² defined in the formula (1), and m is an integer of 1 to 10, provided that at least one R²' represents a monovalent group having an iodine atom.

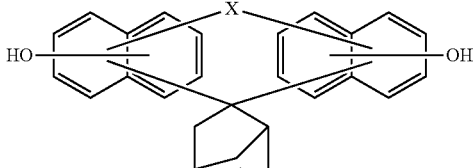

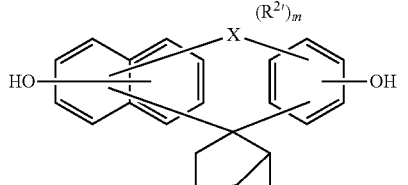
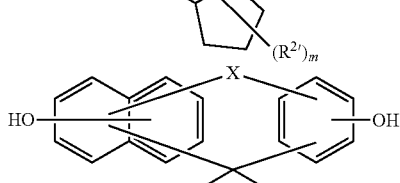

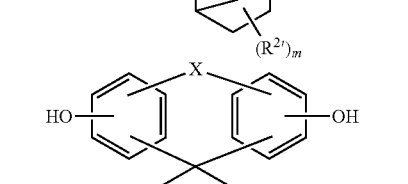
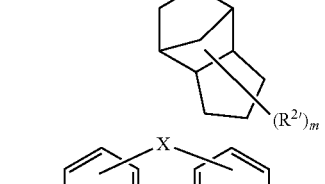

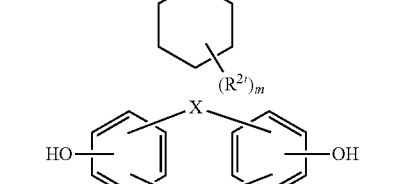

In the above formulae, X is the same as defined in the formula (1), R²' is the same as R² defined in the formula (1), and m is an integer of 1 to 14, provided that at least one R²' represents a monovalent group having an iodine atom.

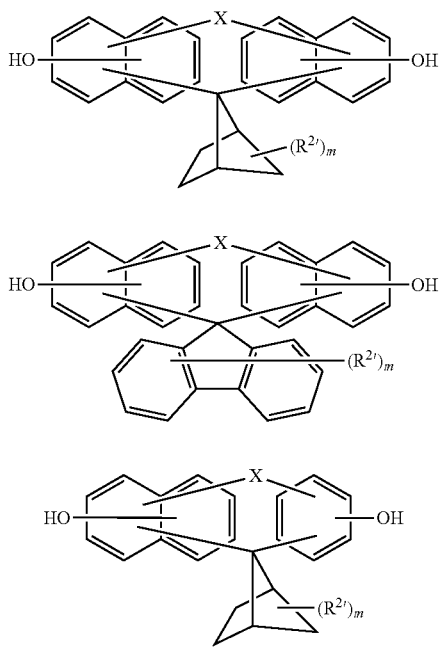

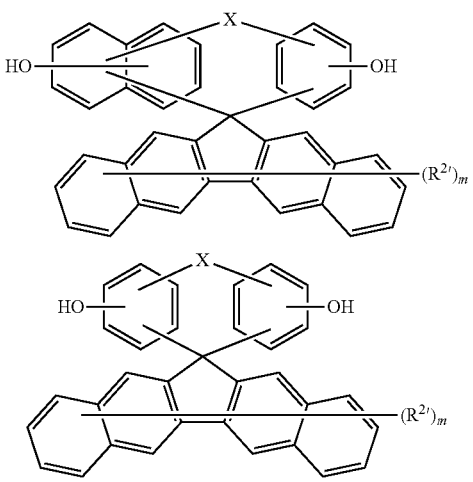

In the above formulae, X is the same as defined in the formula (1), R$^{2'}$ is the same as R$^2$ defined in the formula (1), and m is an integer of 1 to 12, provided that at least one R$^{2'}$ represents a monovalent group having an iodine atom.

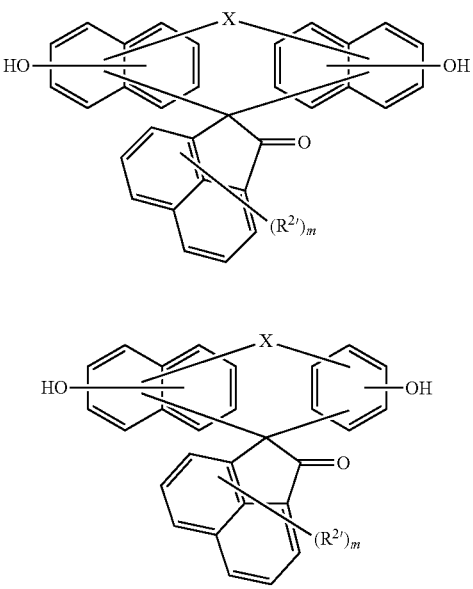

In the above formulae, X is the same as defined in the formula (1), R$^{2'}$ is the same as R$^2$ defined in the formula (1), and m is an integer of 1 to 8, provided that at least one R$^{2'}$ represents a monovalent group having an iodine atom.

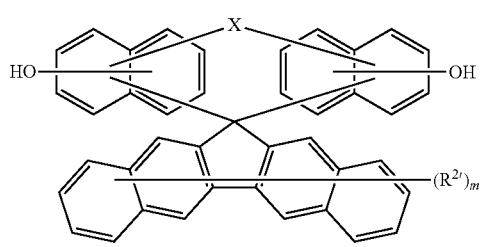

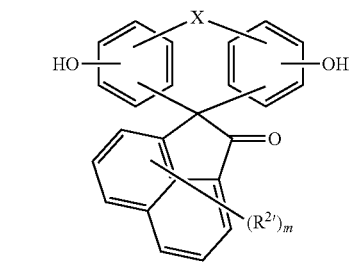

In the above formulae, X is the same as defined in the formula (1), R$^{2'}$ is the same as R$^2$ defined in the formula (1), and m is an integer of 1 to 6, provided that at least one R$^{2'}$ represents a monovalent group having an iodine atom.

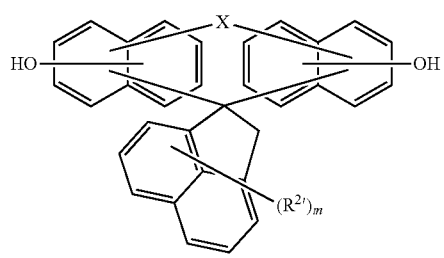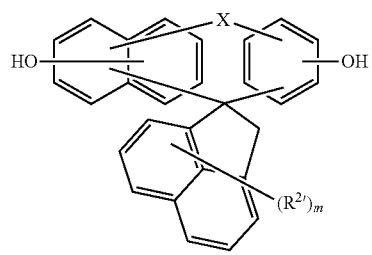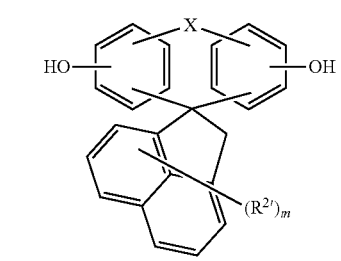
In the above formulae, X is the same as defined in the formula (1), $R^{2'}$ is the same as $R^2$ defined in the formula (1), and m is an integer of 1 to 8, provided that at least one $R^{2'}$ represents a monovalent group having an iodine atom.
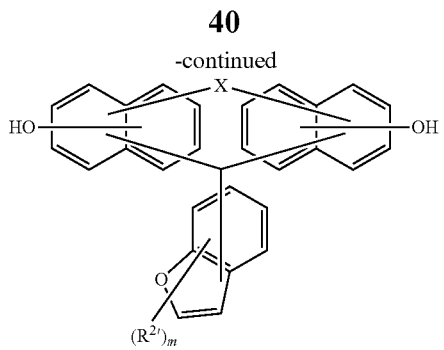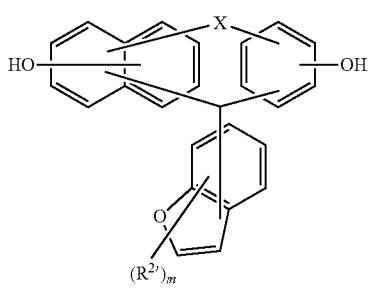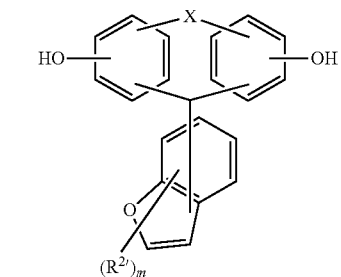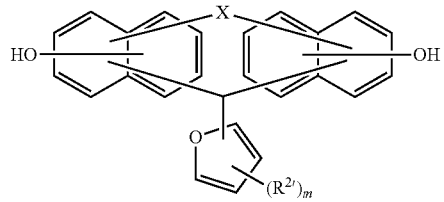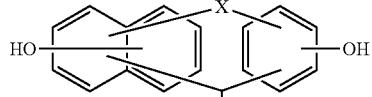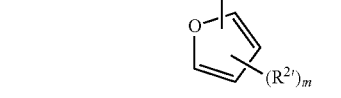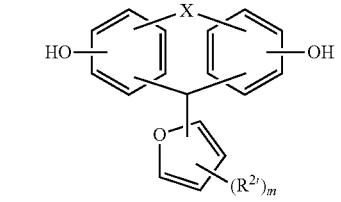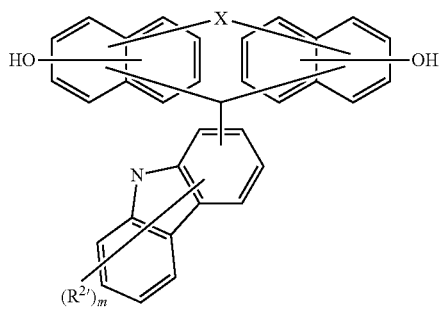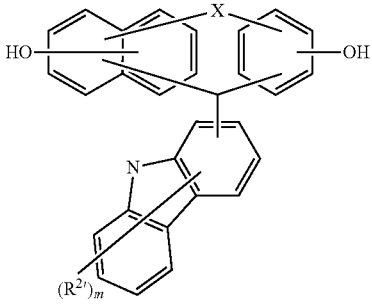

-continued

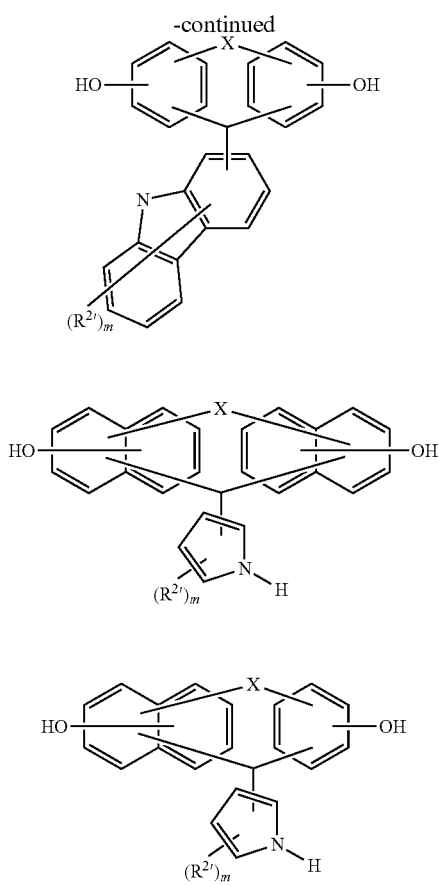

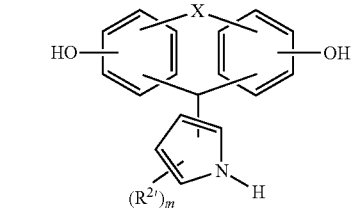

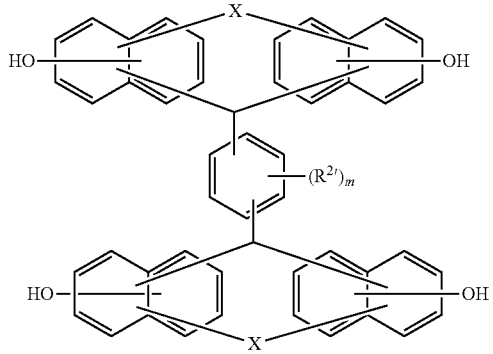

In the above formulae, X is the same as defined in the formula (1), $R^{2'}$ is the same as $R^2$ defined in the formula (1), and m is an integer of 1 to 4, provided that at least one $R^{2'}$ represents a monovalent group having an iodine atom.

-continued

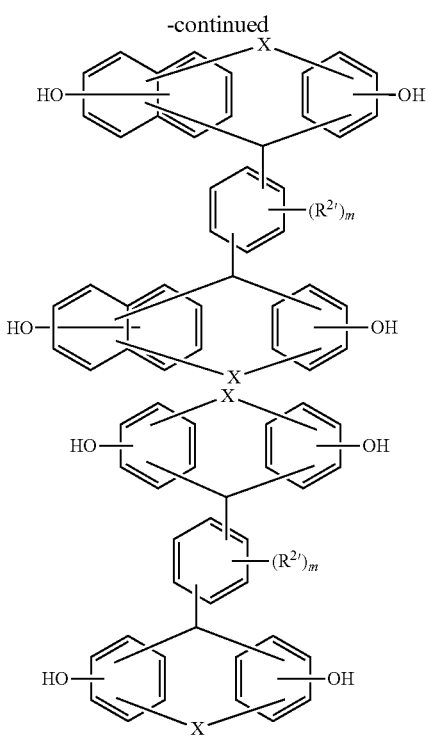

In the above formulae, X is the same as defined in the formula (1), $R^{2'}$ is the same as $R^2$ defined in the formula (1), and m is an integer of 1 to 4, provided that at least one $R^{2'}$ represents a monovalent group having an iodine atom.

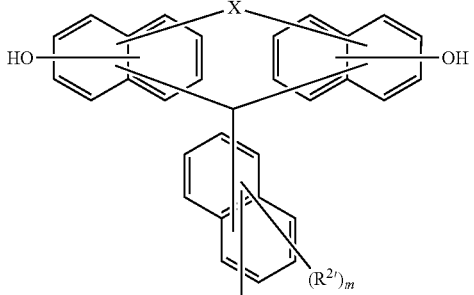

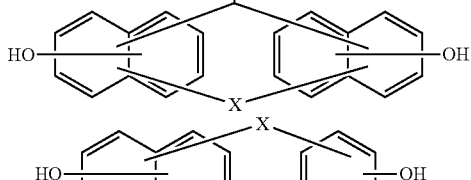

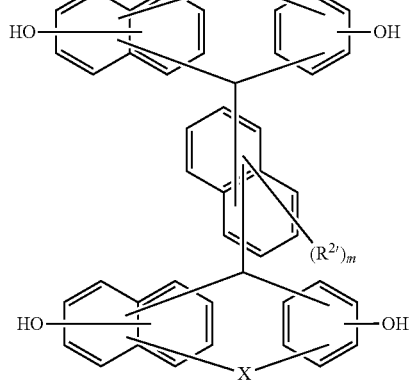

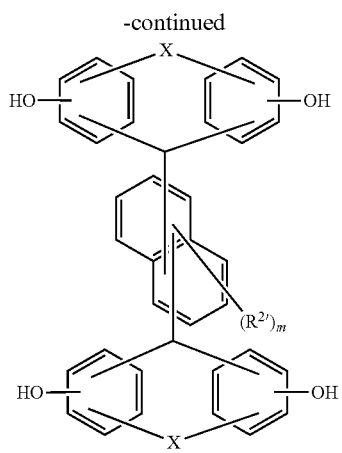
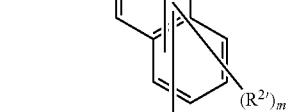
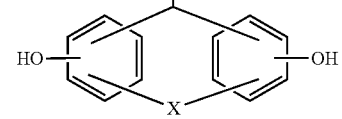
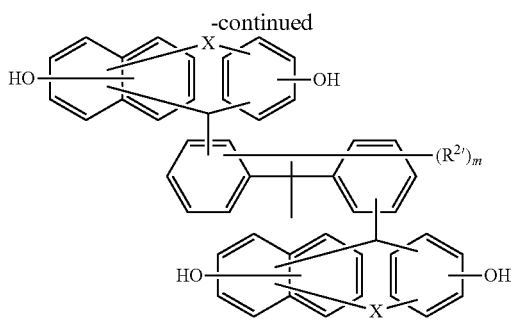
In the above formulae, X is the same as defined in the formula (1), R$^{2'}$ is the same as R$^2$ defined in the formula (1), and m is an integer of 1 to 6, provided that at least one R$^{2'}$ represents a monovalent group having an iodine atom.
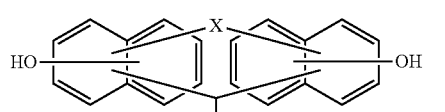
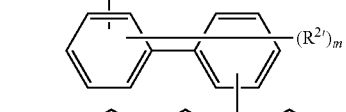
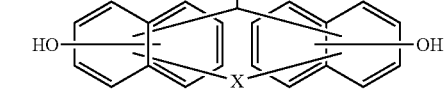
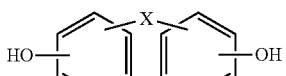
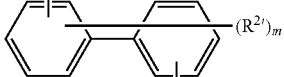
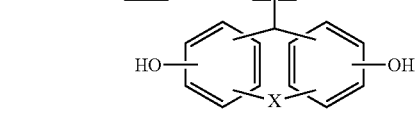
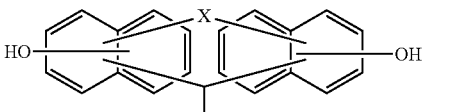
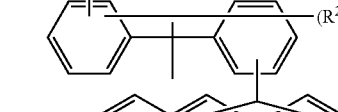
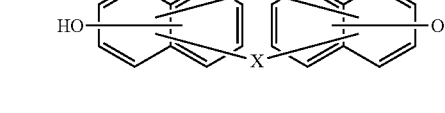
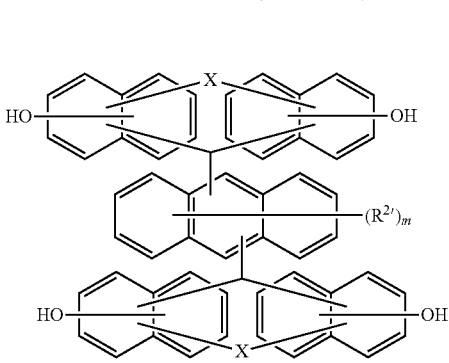
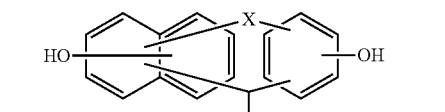
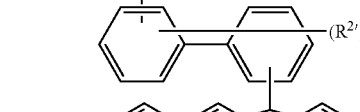
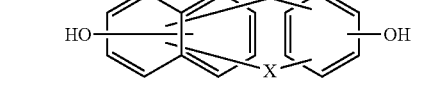
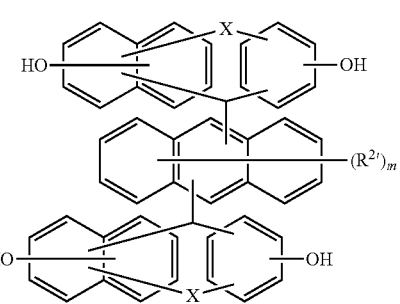

-continued

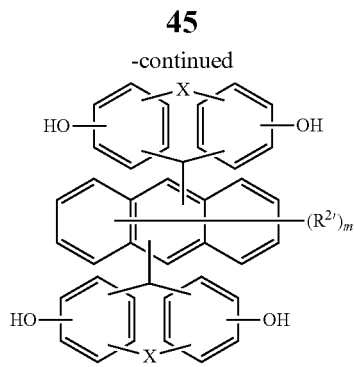

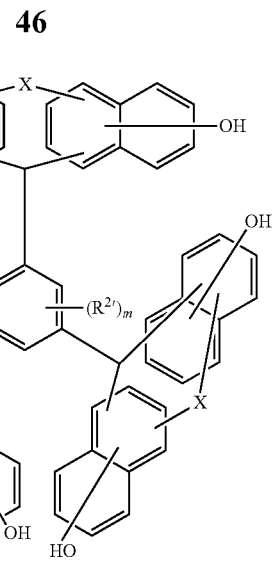

In the above formulae, X is the same as defined in the formula (1), $R^{2'}$ is the same as $R^2$ defined in the formula (1), and m is an integer of 1 to 8, provided that at least one $R^{2'}$ represents a monovalent group having an iodine atom.

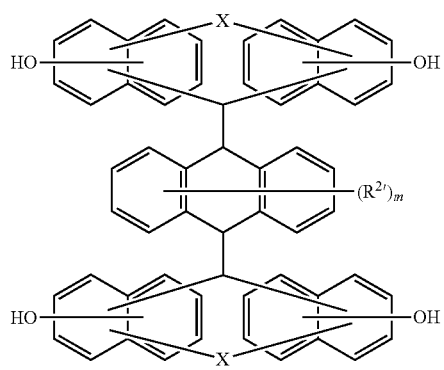

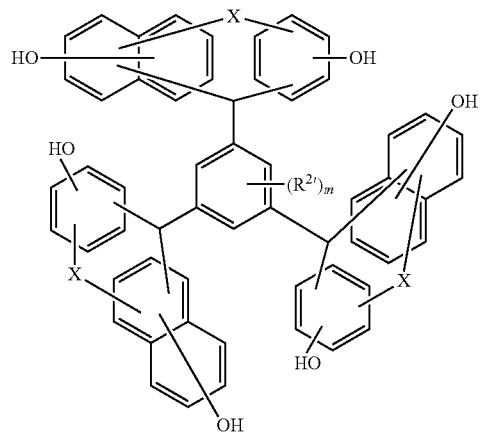

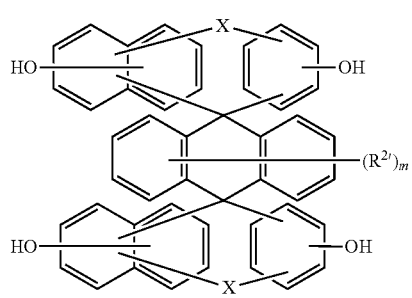

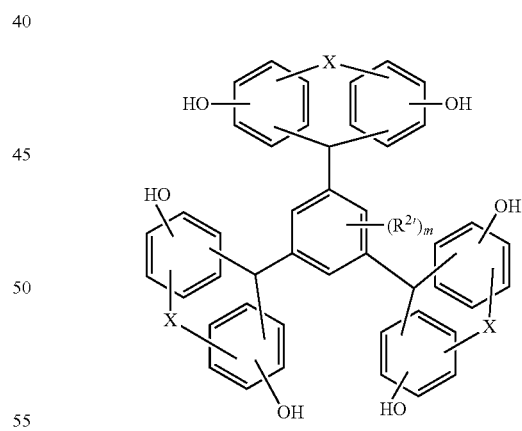

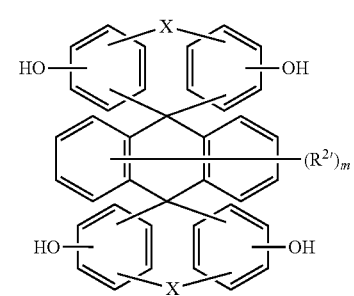

In the above formulae, X is the same as defined in the formula (1), $R^{2'}$ is the same as $R^2$ defined in the formula (1), and m is an integer of 1 to 10, provided that at least one $R^{2'}$ represents a monovalent group having an iodine atom.

In the above formulae, X is the same as defined in the formula (1), $R^{2'}$ is the same as $R^2$ defined in the formula (1), and m is an integer of 1 to 3, provided that at least one $R^{2'}$ represents a monovalent group having an iodine atom.

The compound represented by the formula (1-5) or the formula (1-6) is, in particular, extremely preferably at least one selected from the group consisting of the following compounds from the viewpoint that the effects of the present invention are more certainly exerted.

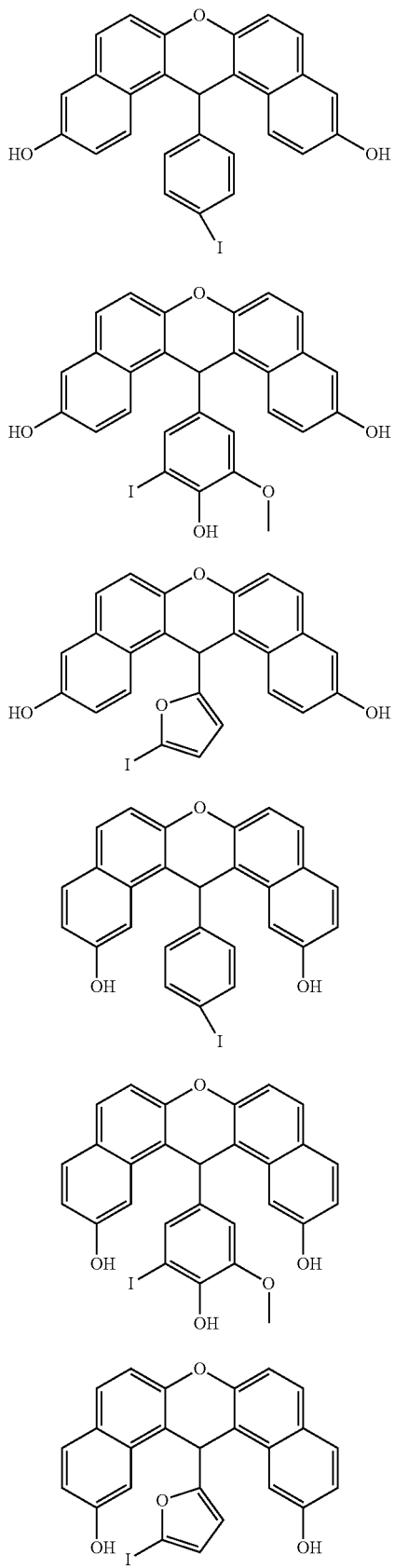

[Resin]

The resin for use in the present embodiment is a resin obtained with the compound represented by the formula (1) as a monomer, and includes a structural unit derived from the compound represented by the formula (1). The resin of the present embodiment is obtained by, for example, reacting the compound represented by the formula (1) with a compound having crosslinking reactivity.

The compound having crosslinking reactivity is not particularly limited as long as it can provide an oligomer or a polymer of the compound represented by the formula (1), and known one can be used therefor. Specific examples thereof include aldehyde, ketone, carboxylic acid, carboxylic halide, a halogen-containing compound, an amino compound, an imino compound, isocyanate, and an unsaturated hydrocarbon group-containing compound, but are not limited thereto.

The material for forming an underlayer film for lithography of the present embodiment contains at least one substance selected from the group consisting of the compound represented by the formula (1) and the resin including the structural unit derived from the compound. In the present embodiment, the content of the substance in the material for forming an underlayer film for lithography is preferably 1 to 100% by mass, more preferably 10 to 100% by mass, further preferably 50 to 100% by mass, further more preferably 100% by mass in terms of coatability and quality stability.

The material for forming an underlayer film for lithography of the present embodiment can be applied to a wet process, and is excellent in heat resistance and etching resistance. Furthermore, since the material for forming an underlayer film for lithography of the present embodiment is formed using the substance, the material can be used to form an underlayer film whose degradation is suppressed at high-temperature baking and which is also excellent in etching resistance to oxygen plasma etching or the like. Furthermore, the material for forming an underlayer film for lithography of the present embodiment is also excellent in adhesiveness with a resist layer, and therefore can form an excellent resist pattern. Herein, the material for forming an underlayer film for lithography of the present embodiment may also include an already known material for forming an underlayer film for lithography as long as the effect of the present embodiment is not impaired.

[Composition for Forming Underlayer Film for Lithography]

A composition for forming an underlayer film for lithography of the present embodiment contains the material for forming an underlayer film for lithography, and a solvent.

[Solvent]

A known solvent can be appropriately used as the solvent for use in the present embodiment as long as it dissolves at least the compound represented by the formula (1) and/or the resin including the compound as a constituent component.

Specific examples of the solvent include ketone-based solvents such as acetone, methyl ethyl ketone, methyl isobutyl ketone and cyclohexanone; cellosolve-based solvents such as propylene glycol monomethyl ether and propylene glycol monomethyl ether acetate; ester-based solvents such as ethyl lactate, methyl acetate, ethyl acetate, butyl acetate, isoamyl acetate, methyl methoxypropionate and methyl hydroxyisobutyrate; alcohol-based solvents such as methanol, ethanol, isopropanol and 1-ethoxy-2-propanol; and aromatic hydrocarbons such as toluene, xylene and anisole, but are not particularly limited thereto. These organic solvents can be used singly or in combinations of two or more thereof.

Among the solvents, preferable are cyclohexanone, propylene glycol monomethyl ether, propylene glycol monomethyl ether acetate, ethyl lactate, methyl hydroxyisobutyrate, and anisole, in terms of safety.

The content of the solvent is not particularly limited, but it is preferably 100 to 10000 parts by mass, more preferably 200 to 5000 parts by mass, further preferably 200 to 1000 parts by mass based on 100 parts by mass of the material for forming an underlayer film, in terms of solubility and film formation.

[Crosslinking Agent]

The composition for forming an underlayer film for lithography of the present embodiment may further contain, if necessary, a crosslinking agent from the viewpoint of suppression of intermixing, and the like. Specific examples of the crosslinking agent usable in the present embodiment include a melamine compound, a guanamine compound, a glycoluril compound, a urea compound, an epoxy compound, a thioepoxy compound, an isocyanate compound, an azide compound, and a compound including a double bond such as an alkenyl ether group, these compounds being substituted with at least one group selected from a methylol group, an alkoxymethyl group and an acyloxymethyl group, as a substituent (crosslinkable group), but are not particularly limited thereto. Herein, these crosslinking agents can be used singly or in combinations of two or more thereof. Such a crosslinking agent can also be used as an additive. Herein, the crosslinkable group may also be introduced as a pendant group into a polymer side chain of the compound represented by the formula (1) and/or the resin obtained with the compound as a monomer. A compound including a hydroxy group can also be used as the crosslinking agent.

Specific examples of the melamine compound include hexamethylolmelamine, hexamethoxymethylmelamine, a compound in which 1 to 6 methylol groups in hexamethylolmelamine are methoxymethylated, or mixtures thereof, and hexamethoxyethylmelamine, hexaacyloxymethylmelamine, a compound in which 1 to 6 methylol groups in hexamethylolmelamine are acyloxymethylated, or mixtures thereof. Specific examples of the epoxy compound include tris(2,3-epoxypropyl)isocyanurate, trimethylolmethane triglycidyl ether, trimethylolpropane triglycidyl ether, and triethylolethane triglycidyl ether.

Specific examples of the guanamine compound include tetramethylolguanamine, tetramethoxymethylguanamine, a compound in which 1 to 4 methylol groups in tetramethylolguanamine are methoxymethylated, or mixtures thereof, and tetramethoxyethylguanamine, tetraacyloxyguanamine, a compound in which 1 to 4 methylol groups in tetramethylolguanamine are acyloxymethylated, or mixtures thereof. Specific examples of the glycoluril compound include tetramethylolglycoluril, tetramethoxyglycoluril, tetramethoxymethylglycoluril, a compound in which 1 to 4 methylol groups in tetramethylolglycoluril are methoxymethylated, or mixtures thereof, and a compound in which 1 to 4 methylol groups in tetramethylolglycoluril are acyloxymethylated, or mixtures thereof. Specific examples of the urea compound include tetramethylolurea, tetramethoxymethylurea, a compound in which 1 to 4 methylol groups in tetramethylolurea are methoxymethylated, or mixtures thereof, and tetramethoxyethylurea.

Specific examples of the compound including an alkenyl ether group include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, and sorbitol pentavinyl ether.

In the material for forming an underlayer film for lithography of the present embodiment, the content of the crosslinking agent is not particularly limited, but the content is preferably 5 to 50 parts by mass, more preferably 10 to 40 parts by mass based on 100 parts by mass of the material for forming an underlayer film. The content is set within the above preferable range to result in tendencies to suppress the occurrence of the mixing phenomenon with the resist layer, and to result in tendencies to enhance an antireflective effect and improve film formability after crosslinking.

[Acid Generator]

The composition for forming an underlayer film for lithography of the present embodiment may further contain, if necessary, an acid generator from the viewpoint of further promoting a crosslinking reaction by heat, and the like. As the acid generator, one for generating an acid by pyrolysis and one for generating an acid by light irradiation are known, and any of them can be used.

The acid generator includes, for example:
1) an onium salt of the following general formula (P1a-1), (P1a-2), (P1a-3) or (P1b),
2) a diazomethane derivative of the following general formula (P2),
3) a glyoxime derivative of the following general formula (P3),
4) a bissulfone derivative of the following general formula (P4),
5) a sulfonic acid ester of an N-hydroxyimide compound of the following general formula (P5),
6) a β-ketosulfonic acid derivative,
7) a disulfone derivative,
8) a nitrobenzylsulfonate derivative, and
9) a sulfonic acid ester derivative, but is not particularly limited thereto. Herein, these acid generators can be used alone, or two or more thereof can be used in combination.

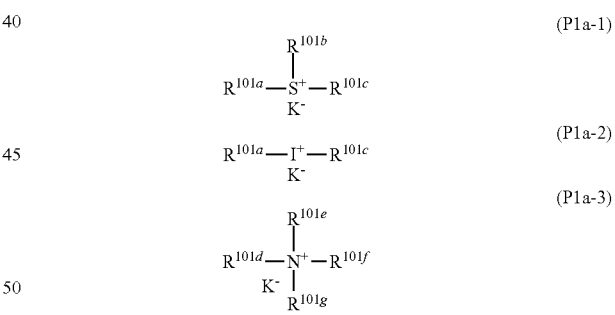

In the above formulae, each of $R^{101a}$, $R^{101b}$ and $R^{101c}$ independently represents a straight, branched or cyclic alkyl group, alkenyl group, oxoalkyl group or oxoalkenyl group having 1 to 12 carbon atoms; an aryl group having 6 to 20 carbon atoms; or an aralkyl group or aryloxoalkyl group having 7 to 12 carbon atoms, and a part or all of hydrogen atoms of these groups may be substituted with an alkoxy group or the like. In addition, $R^{101b}$ and $R^{101c}$ may form a ring, and if forming a ring, each of $R^{101b}$ and $R^{101c}$ independently represents an alkylene group having 1 to 6 carbon atoms. $K^-$ represents a non-nucleophilic counter ion. $R^{101d}$, $R^{101e}$, $R^{101f}$ and $R^{101g}$ are represented by each independently adding a hydrogen atom to $R^{101a}$, $R^{101b}$ and $R^{101c}$. $R^{101d}$ and $R^{101e}$, and $R^{101d}$, $R^{101e}$ and $R^{101f}$ may form a ring, and if forming a ring, $R^{101d}$ and $R^{101e}$, and $R^{101d}$, $R^{101e}$ and $R^{101f}$ represent an alkylene group having 3 to 10 carbon atoms, or a heteroaromatic ring having therein the nitrogen atom(s) in the formula.

$R^{101a}$, $R^{101b}$, $R^{101c}$, $R^{101d}$, $R^{101e}$, $R^{101f}$ and $R^{101g}$ described above may be the same or different from one another. Specifically, examples of the alkyl group include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methyl cyclohexyl group, a cyclohexylmethyl group, a norbornyl group, and an adamantyl group. Examples of the alkenyl group include, but are not limited to the following, a vinyl group, an allyl group, a propenyl group, a butenyl group, a hexenyl group, and a cyclohexenyl group. Examples of the oxoalkyl group can include, but are not limited to the following, a 2-oxocyclopentyl group, a 2-oxocyclohexyl group, a 2-oxopropyl group, a 2-cyclopentyl-2-oxoethyl group, a 2-cyclohexyl-2-oxoethyl group, and a 2-(4-methylcyclohexyl)-2-oxoethyl group. Examples of the oxoalkenyl group include, but are not limited to the following, a 2-oxo-4-cyclohexenyl group and a 2-oxo-4-propenyl group. Examples of the aryl group include, but are not limited to the following, a phenyl group, a naphthyl group, alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group; alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group; alkylnaphthyl groups such as a methylnaphthyl group and an ethylnaphthyl group; alkoxynaphthyl groups such as a methoxynaphthyl group and an ethoxynaphthyl group; dialkylnaphthyl groups such as a dimethylnaphthyl group and a diethylnaphthyl group; and dialkoxynaphthyl groups such as a dimethoxynaphthyl group and a diethoxynaphthyl group. Examples of the aralkyl group include, but are not limited to the following, a benzyl group, a phenylethyl group, and a phenethyl group. Examples of the aryloxoalkyl group include, but are not limited to the following, 2-aryl-2-oxoethyl groups such as a 2-phenyl-2-oxoethyl group, a 2-(1-naphthyl)-2-oxoethyl group, and a 2-(2-naphthyl)-2-oxoethyl group. Examples of the non-nucleophilic counter ion, $K^-$, include, but are not limited to the following, halide ions such as a chloride ion and a bromide ion; fluoroalkyl sulfonates such as triflate, 1,1,1-trifluoroethane sulfonate, and nonafluorobutane sulfonate; aryl sulfonates such as tosylate, benzene sulfonate, 4-fluorobenzene sulfonate, and 1,2,3,4,5-pentafluorobenzene sulfonate; and alkyl sulfonates such as mesylate and butane sulfonate.

In the case where $R^{101d}$, $R^{101e}$, $R^{101f}$ and $R^{101g}$ are each a heteroaromatic ring having the nitrogen atom(s) in the formula, examples of the heteroaromatic ring include imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline and 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivative, and uridine derivatives.

The onium salts of the formula (P1a-1) and the formula (P1a-2) have functions as a photo acid generator and a thermal acid generator. The onium salt of the formula (P1a-3) has a function as a thermal acid generator.

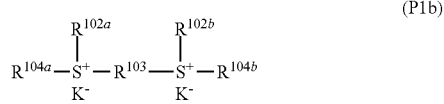

(P1b)

In the formula (P1b), each of $R^{102a}$ and $R^{102b}$ independently represents a straight, branched or cyclic alkyl group having 1 to 8 carbon atoms. $R^{103}$ represents a straight, branched or cyclic alkylene group having 1 to 10 carbon atoms. Each of $R^{104a}$ and $R^{104b}$ independently represents a 2-oxoalkyl group having 3 to 7 carbon atoms. $K^-$ represents a non-nucleophilic counter ion.

Specific examples of $R^{102a}$ and $R^{102b}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methyl cyclohexyl group, and a cyclohexylmethyl group. Specific examples of $R^{103}$ include, but are not limited to the following, a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexanedimethylene group. Specific examples of $R^{104a}$ and $R^{104b}$ include, but are not limited to the following, a 2-oxopropyl group, a 2-oxocyclopentyl group, a 2-oxocyclohexyl group, and a 2-oxocycloheptyl group. $K^-$ includes the same as those described in the formula (P1a-1), (P1a-2) and (P1a-3).

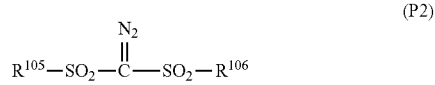

(P2)

In the formula (P2), each of $R^{105}$ and $R^{106}$ independently represents a straight, branched or cyclic alkyl group or halogenated alkyl group having 1 to 12 carbon atoms, an aryl group or halogenated aryl group having 6 to 20 carbon atoms, or an aralkyl group having 7 to 12 carbon atoms.

Examples of the alkyl group in each of $R^{105}$ and $R^{106}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an adamantyl group. Examples of the halogenated alkyl group include, but are not limited to the following, a trifluoromethyl group, a 1,1,1-trifluoroethyl group, a 1,1,1-trichloroethyl group, and a nonafluorobutyl group. Examples of the aryl group include, but are not limited to the following, alkoxyphenyl groups such as a phenyl group, a p-methoxyphenyl group, a m-methoxyphenyl group, an o-methoxyphenyl group, an ethoxyphenyl group, a p-tert-butoxyphenyl group, and a m-tert-butoxyphenyl group; and alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group. Examples of the halogenated aryl group include, but are not limited to the following, a fluorophenyl group, a chlorophenyl group, and a 1,2,3,4,5-pentafluorophenyl group. Examples of the aralkyl group include, but are not limited to the following, a benzyl group and a phenethyl group.

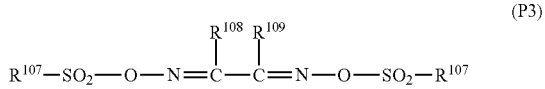
(P3)

In the formula (P3), each of $R^{107}$, $R^{108}$ and $R^{109}$ independently represents a straight, branched or cyclic alkyl group or halogenated alkyl group having 1 to 12 carbon atoms; an aryl group or halogenated aryl group having 6 to 20 carbon atoms; or an aralkyl group having 7 to 12 carbon atoms. $R^{108}$ and $R^{109}$ may be bonded with each other to form a cyclic structure, and if forming a cyclic structure, each of $R^{108}$ and $R^{109}$ represents a straight or branched alkylene group having 1 to 6 carbon atoms.

The alkyl group, halogenated alkyl group, aryl group, halogenated aryl group, and aralkyl group in each of $R^{107}$, $R^{108}$ and $R^{109}$ include the same as those described in $R^{105}$ and $R^{106}$. Herein, examples of the alkylene group in each of $R^{108}$ and $R^{109}$ include, but are not limited to the following, a methylene group, an ethylene group, a propylene group, a butylene group, and a hexylene group.

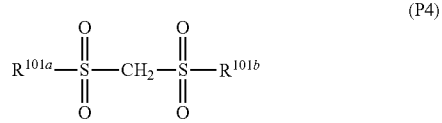
(P4)

In the formula (P4), $R^{101a}$ and $R^{101b}$ are the same as $R^{107}$ in the formula (P3).

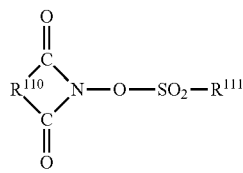
(P5)

In the formula (P5), $R^{110}$ represents an arylene group having 6 to 10 carbon atoms, an alkylene group having 1 to 6 carbon atoms, or an alkenylene group having 2 to 6 carbon atoms, and a part or all of hydrogen atoms of these groups may be further substituted with a straight or branched alkyl group or alkoxy group having 1 to 4 carbon atoms, a nitro group, an acetyl group, or a phenyl group. $R^{111}$ represents a straight, branched or substituted alkyl group, alkenyl group or alkoxyalkyl group having 1 to 8 carbon atoms, a phenyl group, or a naphthyl group, and a part or all of hydrogen atoms of these groups may be further substituted with an alkyl group or alkoxy group having 1 to 4 carbon atoms; a phenyl group that may be substituted with an alkyl group or alkoxy group having 1 to 4 carbon atoms, a nitro group, or an acetyl group; a heteroaromatic group having 3 to 5 carbon atoms; or a chlorine atom or a fluorine atom.

Herein, examples of the arylene group in $R^{110}$ include, but are not limited to the following, a 1,2-phenylene group and a 1,8-naphthylene group. Examples of the alkylene group include, but are not limited to the following, a methylene group, an ethylene group, a trimethylene group, a tetramethylene group, a phenylethylene group, and a norbornane-2,3-diyl group. Examples of the alkenylene group include, but are not limited to the following, a 1,2-vinylene group, a 1-phenyl-1,2-vinylene group, and a 5-norbornene-2,3-diyl group. The alkyl group in $R^{111}$ includes the same as those in $R^{101a}$ to $R^{101c}$. Examples of the alkenyl group include, but are not limited to the following, a vinyl group, a 1-propenyl group, an allyl group, a 1-butenyl group, a 3-butenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, and a 7-octenyl group. Examples of the alkoxyalkyl group include, but are not limited to the following, a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, and a methoxyheptyl group.

Herein, Examples of the alkyl group having 1 to 4 carbon atoms, which may be further substituted, include, but are not limited to the following, a methyl group, an ethyl group, a propyl group, an isopropyl group, a n-butyl group, a an isobutyl group, and a tert-butyl group. Examples of the alkoxy group having 1 to 4 carbon atoms include, but are not limited to the following, a methoxy group, an ethoxy group, a propoxy group, an isopropoxy group, a n-butoxy group, an isobutoxy group, and tert-butoxy group. Examples of the phenyl group that may be substituted with an alkyl group or alkoxy group having 1 to 4 carbon atoms, a nitro group, or an acetyl group include, but are not limited to the following, a phenyl group, a tolyl group, a p-tert-butoxyphenyl group, a p-acetylphenyl group, and a p-nitrophenyl group. Examples of the heteroaromatic group having 3 to 5 carbon atoms include, but are not limited to the following, a pyridyl group and a furyl group.

Specific examples of the acid generator include, but are not limited to the following, onium salts such as tetramethylammonium trifluoromethanesulfonate, tetramethylammonium nonafluorobutanesulfonate, triethylammonium nonafluorobutanesulfonate, pyridinium nonafluorobutanesulfonate, triethylammonium camphorsulfonate, pyridinium camphorsulfonate, tetra n-butylammonium nonafluorobutanesulfonate, tetraphenylammonium nonafluorobutanesulfonate, tetramethylammonium p-toluenesulfonate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylene bis[methyl(2-oxocyclopentyl)sulfonium trifluoromethanesulfonate], and 1,2'-naphthylcarbonylmethyltetrahydrothiophenium triflate; diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane; glyoxime derivatives such as bis-(p-toluenesulfonyl)-α-dimethylglyoxime, bis-(p-toluesulfonyl)-α-diphenylglyoxime, bis-(p-toluenesulfonyl)-α-dicyclohexylglyoxime, bis-(p-toluenesulfonyl)-2,3-pentanedioneglyoxime, bis-(p-toluenesulfonyl)-2-methyl-3,4-pentanedioneglyoxime, bis-(n-butanesulfonyl)-α-dimethylglyoxime, bis-(n-butanesulfonyl)-α-diphenylglyoxime, bis-(n-butanesulfonyl)-α-dicyclohexylglyoxime, bis-(n-butanesulfonyl)-2,3-pentanedioneglyoxime, bis-(n-butanesulfonyl)-2-methyl-3,4-pentanedioneglyoxime, bis-(methanesulfonyl)-α-dimethylglyoxime, bis-(trifluoromethanesulfonyl)-α-dimethylglyoxime, bis-(1,1,1-trifluoroethanesulfonyl)-α-dimethylglyoxime, bis-(tert-butanesulfonyl)-α-dimethylglyoxime, bis-(perfluorooctanesulfonyl)-α-dimethylglyoxime, bis-(cyclohexanesulfonyl)-α-dimethylglyoxime, bis-(benzenesulfonyl)-α-dimethylglyoxime, bis-(p-fluorobenzenesulfonyl)-α-dimethylglyoxime, bis-(p-tert-butylbenzenesulfonyl)-α-dimethylglyoxime, bis-(xylenesulfonyl)-α-dimethylglyoxime, and bis-(camphorsulfonyl)-α-dimethylglyoxime; bissulfone derivatives, such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane; β-ketosulfone derivatives such as 2-cyclohexylcarbonyl-2-(p-toluenesulfonyl)propane and 2-isopropylcarbonyl-2-(p-toluenesulfonyl)propane; disulfone derivatives such as a diphenyldisulfone derivative and a dicyclohexyldisulfone derivative, nitrobenzylsulfonate derivatives such as 2,6-dinitrobenzyl p-toluenesulfonate and 2,4-dinitrobenzyl p-toluenesulfonate; sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid ester derivatives of a N-hydroxyimide compound, such as N-hydroxysuccinimide methanesulfonic acid ester, N-hydroxysuccinimide trifluoromethanesulfonic acid ester, N-hydroxysuccinimide ethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide 1-octanesulfonic acid ester, N-hydroxysuccinimide p-toluenesulfonic acid ester, N-hydroxysuccinimide p-methoxybenzenesulfonic acid ester, N-hydroxysuccinimide 2-chloroethanesulfonic acid ester, N-hydroxysuccinimide benzenesulfonic acid ester, N-hydroxysuccinimide-2,4,6-trimethylbenzenesulfonic acid ester, N-hydroxysuccinimide 1-naphthalenesulfonic acid ester, N-hydroxysuccinimide 2-naphthalenesulfonic acid ester, N-hydroxy-2-phenylsuccinimide methanesulfonic acid ester, N-hydroxymaleimide methanesulfonic acid ester, N-hydroxymaleimide ethanesulfonic acid ester, N-hydroxy-2-phenylmaleimide methanesulfonic acid ester, N-hydroxyglutarimide methanesulfonic acid ester, N-hydroxyglutarimide benzenesulfonic acid ester, N-hydroxyphthalimide methanesulfonic acid ester, N-hydroxyphthalimide benzenesulfonic acid ester, N-hydroxyphthalimide trifluoromethanesulfonic acid ester, N-hydroxyphthalimide p-toluenesulfonic acid ester, N-hydroxynaphthalimide methanesulfonic acid ester, N-hydroxynaphthalimide benzenesulfonic acid ester, N-hydroxy-5-norbornene-2,3-dicarboxyimide methanesulfonic acid ester, N-hydroxy-5-norbornene-2,3-dicarboxyimide trifluoromethanesulfonic acid ester, and N-hydroxy-5-norbornene-2,3-dicarboxyimide p-toluenesulfonic acid ester.

Among the above, onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-(p-toluenesulfonyl)-α-dimethylglyoxime and bis-(n-butanesulfonyl)-α-dimethylglyoxime, bissulfone derivatives such as bisnaphthylsulfonylmethane; and sulfonic acid ester derivatives of an N-hydroxyimide compound, such as N-hydroxysuccinimide methanesulfonic acid ester, N-hydroxysuccinimide trifluoromethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide p-toluenesulfonic acid ester, N-hydroxynaphthalimide methanesulfonic acid ester, and N-hydroxynaphthalimide benzenesulfonic acid ester, and the like are preferably used.

In the material for forming an underlayer film for lithography according to the present embodiment, the content of the acid generator is not particularly limited, but the content is preferably 0.1 to 50 parts by mass and more preferably 0.5 to 40 parts by mass based on 100 parts by mass of the material for forming an underlayer film. The content is set within the above range to result in a tendency to increase the acid generation amount to promote a crosslinking reaction, and also to result in a tendency to suppress the occurrence of the mixing phenomenon with a resist layer.

[Basic Compound]

The composition for forming an underlayer film for lithography of the present embodiment may further contain a basic compound from the viewpoint of improving preservation stability.

The basic compound serves as a quencher to an acid for preventing a trace amount of the acid generated from the acid generator from promoting a crosslinking reaction. Examples of such a basic compound include primary, secondary, and tertiary aliphatic amines, mixed amines, aromatic amines, heterocyclic amines, a nitrogen-containing compound having a carboxy group, a nitrogen-containing compound having a sulfonyl group, a nitrogen-containing compound having a hydroxyl group, a nitrogen-containing compound having a hydroxyphenyl group, an alcoholic nitrogen-containing compound, an amide derivative, and an imide derivative, but are not particularly limited thereto.

Specific examples of the primary aliphatic amines include, but are not limited to the following, ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Specific examples of the secondary aliphatic amines include, but are not limited to the following, dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Specific examples of the tertiary aliphatic amines include, but are not limited to the following, trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Specific examples of the mixed amines include, but are not limited to the following, dimethylethylamine, methylethylpropylamine, benzylamine, phenethylamine, and benzyldimethylamine. Specific examples of the aromatic amines and heterocyclic amines include, but are not limited to the following, aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (for example, pyrrole, 2H-pyrrole, 1-methylpyrrole, 2,4-dimethylpyrrole, 2,5-dimethylpyrrole, and N-methylpyrrole), oxazole derivatives (for example, oxazole and isoxazole), thiazole derivatives (for example, thiazole and isothiazole), imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline, 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Furthermore, specific examples of the nitrogen-containing compound having a carboxy group include, but are not limited to the following, aminobenzoic acid, indolecarboxylic acid, and amino acid derivatives (for example, nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Specific examples of the nitrogen-containing compound having a sulfonyl group include, but are not limited to the following, 3-pyridinesulfonic acid and pyridinium p-toluenesulfonate. Specific examples of the nitrogen-containing compound having a hydroxyl group, the nitrogen-containing compound having a hydroxyphenyl group, and the alcoholic nitrogen-containing compound include, but are not limited to the following, 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Specific examples of the amide derivative include, but are not limited to the following, formamide, N-methylformamide, N,N-dimethylformamide, acetamide, N-methylacetamide, N,N-dimethylacetamide, propionamide, and benzamide. Specific examples of the imide derivative include, but are not limited to the following, phthalimide, succinimide, and maleimide.

In the composition for forming an underlayer film for lithography according to the present embodiment, the content of the basic compound is not particularly limited, but the content is preferably 0.001 to 2 parts by mass and more preferably 0.01 to 1 part by mass based on 100 parts by mass of the material for forming an underlayer film. The content is set within the above preferable range to result in a tendency to improve preservation stability without excessively interrupting a crosslinking reaction.

[Other Additives]

In addition, the composition for forming an underlayer film for lithography of the present embodiment may further contain other resins and/or compounds for the purposes of imparting heat curability and controlling absorbance. Such other resins and/or compounds include naphthol resins, xylene resins, naphthol-modified resins, phenol-modified resins of naphthalene resins, polyhydroxystyrene, dicyclopentadiene resins, (meth)acrylate, dimethacrylate, trimethacrylate, tetramethacrylate, resins having a naphthalene ring such as vinylnaphthalene and polyacenaphthylene, resins having a biphenyl ring such as phenanthrenequinone and fluorene, resins having a heterocyclic ring having a hetero atom such as thiophene and indene, and resins not containing an aromatic ring; rosin-based resins, and resins or compounds including an alicyclic structure, such as cyclodextrin, adamantane(poly)ol, tricyclodecane(poly)ol and derivatives thereof, but are not particularly limited thereto. Furthermore, the material for forming an underlayer film for lithography of the present embodiment can also contain a known additive. Examples of the known additive includes, but not limited to the following, an ultraviolet absorber, a surfactant, a colorant and a non-ionic surfactant.

[Underlayer Film for Lithography and Production Method Thereof]

An underlayer film for lithography of the present embodiment is formed from the composition for forming an underlayer film for lithography of the present embodiment. In addition, a method for producing an underlayer film for lithography of the present embodiment includes a step of forming an underlayer film on a substrate by using the composition for forming an underlayer film for lithography of the present embodiment.

[Multilayer Resist Pattern Forming Method]

In addition, a resist pattern forming method of the present embodiment includes step (A-1) of forming an underlayer film on a substrate by using the composition for forming an underlayer film for lithography of the present embodiment, step (A-2) of forming at least one photoresist layer on the underlayer film, and step (A-3) of irradiating a predetermined region of the photoresist layer with radiation, and developing it.

Furthermore, another pattern forming method (circuit pattern forming method) of the present embodiment includes step (B-1) of forming an underlayer film on a substrate by using the composition for forming an underlayer film for lithography of the present embodiment, step (B-2) of forming an intermediate layer film on the underlayer film by using a silicon atom-containing resist intermediate layer film material, step (B-3) of forming at least one photoresist layer on the intermediate layer film, step (B-4) of irradiating a predetermined region of the photoresist layer with radiation and developing it to form a resist pattern, step (B-5) of etching the intermediate layer film with the resist pattern as a mask to form an intermediate layer film pattern, step (B-6) of etching the underlayer film with the intermediate layer film pattern as an etching mask to form an underlayer film pattern, and step (B-7) of etching the substrate with the underlayer film pattern as an etching mask to form a pattern on the substrate.

The underlayer film for lithography of the present embodiment is not particularly limited in terms of the forming method thereof as long as it is formed from the composition for forming an underlayer film for lithography of the present embodiment, and a known method can be applied. For example, the underlayer film can be formed by applying the composition for forming an underlayer film for lithography of the present embodiment on the substrate by a known coating method such as spin coating or screen printing, a printing method, or the like, and then removing an organic solvent by volatilization or the like.

The underlayer film is preferably baked upon forming in order to suppress the occurrence of the mixing phenomenon with an upperlayer resist and also promote a crosslinking reaction. In this case, the baking temperature is not particularly limited, but it is preferably within the range of 80 to 450° C., and more preferably 200 to 400° C. In addition, the baking time is not also particularly limited, but is preferably within the range of 10 to 300 seconds. Herein, the thickness of the underlayer film can be appropriately selected depending on the required properties, and is not particularly limited, but is preferably about 30 to 20000 nm, more preferably 50 to 15000 nm.

After the underlayer film is prepared, in the case of a two-layer process, a silicon-containing resist layer or a usual single-layer resist including a hydrocarbon is preferably prepared on the underlayer film, and in the case of a three-layer process, a silicon-containing intermediate layer is preferably prepared on the underlayer film, and a single-layer resist layer not containing silicon is preferably prepared on the silicon-containing intermediate layer. In these cases, a photoresist material for forming the resist layer, which can be used, is a known one.

After the underlayer film is prepared on the substrate, in the case of a two-layer process, a silicon-containing resist layer or a usual single-layer resist including a hydrocarbon can be prepared on the underlayer film. In the case of a three-layer process, a silicon-containing intermediate layer can be prepared on the underlayer film, and a single-layer resist layer not containing silicon can be prepared on the silicon-containing intermediate layer. In these cases, a photoresist material for forming the resist layer, which can be used, is appropriately selected from known ones, and is not particularly limited.

As the silicon-containing resist material for a two-layer process, a positive-type photoresist material is preferably used, which contains a silicon atom-containing polymer such as a polysilsesquioxane derivative or a vinylsilane derivative used as a base polymer in the viewpoint of oxygen gas-etching resistance, and an organic solvent, an acid generator and if necessary a basic compound. Herein, as the silicon atom-containing polymer, a known polymer used in such a resist material can be used.

As the silicon-containing intermediate layer for a three-layer process, a polysilsesquioxane-based intermediate layer is preferably used. The intermediate layer is allowed to have an effect as an antireflective film, and thus tends to make it possible to effectively suppress reflection. For example, if a material including many aromatic groups and having a high substrate-etching resistance is used for the underlayer film in a 193 nm exposure process, a k-value tends to be increased to increase substrate reflection, but the reflection can be suppressed by the intermediate layer to thereby make the substrate reflection 0.5% or less. For the intermediate layer having such an antireflection effect, but not limited to the following, polysilsesquioxane into which a phenyl group or a light-absorbing group having a silicon-silicon bond for 193 nm exposure is introduced and which is to be crosslinked with an acid or heat is preferably used.

An intermediate layer formed by the Chemical Vapour Deposition (CVD) method can also be used. As the intermediate layer having a high effect as an antireflective film, prepared by the CVD method, but not limited to the following, for example, a SiON film is known. In general, the intermediate layer is formed by a wet process such as a spin coating method or screen printing rather than the CVD method in terms of simplicity and cost effectiveness. Herein, the upperlayer resist in a three-layer process may be of positive-type or negative-type, and the same one as a commonly used single-layer resist can be used therefor.

Furthermore, the underlayer film of the present embodiment can also be used as a usual antireflective film for use in a single-layer resist or a usual underlying material for suppressing pattern collapse. The underlayer film of the present embodiment can also be expected to serve as a hard mask for underlying processing because of being excellent in etching resistance for underlying processing.

In the case where a resist layer is formed by the photoresist material, a wet process such as a spin coating method or screen printing is preferably used as in the case of forming the underlayer film. The resist material is coated by a spin coating method or the like and then usually pre-baked, and such pre-baking is preferably performed in the range of 80 to 180° C. for 10 to 300 seconds. Thereafter, in accordance with an ordinary method, the resultant can be subjected to exposure, post-exposure bake (PEB), and development to obtain a resist pattern. Herein, the thickness of the resist film is not particularly limited, but generally, it is preferably 30 to 500 nm and more preferably 50 to 400 nm.

Light for use in exposure may be appropriately selected depending on the photoresist material to be used. Examples of the light for use in exposure include high energy radiation having a wavelength of 300 nm or less, specifically, excimer lasers of 248 nm, 193 nm, and 157 nm, a soft X-ray of 3 to 20 nm, electron beam, and an X-ray.

The resist pattern formed by the above method is a pattern whose collapse is suppressed by the underlayer film of the present embodiment. Therefore, the underlayer film of the present embodiment can be used to thereby obtain a finer pattern, and an exposure amount necessary for obtaining such a resist pattern can be reduced.

Then, the obtained resist pattern is used as a mask to perform etching. As the etching of the underlayer film in a two-layer process, gas etching is preferably used. As the gas etching, etching using oxygen gas is suitable. In addition to oxygen gas, an inert gas such as He and Ar, and CO, $CO_2$, $NH_3$, $SO_2$, $N_2$, $NO_2$, and $H_2$ gases can also be added. The gas etching can also be performed not using oxygen gas but using only CO, $CO_2$, $NH_3$, $N_2$, $NO_2$, and $H_2$ gases. In particular, the latter gases are preferably used for protecting a side wall for preventing a pattern side wall from being undercut.

On the other hand, also in the etching of the intermediate layer in a three-layer process, gas etching is preferably used. As the gas etching, the same one as the one described in a two-layer process can be applied. In particular, the intermediate layer is preferably processed in a three-layer process using a fluorocarbon gas with the resist pattern as a mask. Thereafter, as described above, the intermediate layer pattern is used as a mask to perform, for example, oxygen gas etching, thereby processing the underlayer film.

Herein, in the case where an inorganic hard mask intermediate layer film is formed as the intermediate layer, a silicon oxide film, a silicon nitride film, and a silicon oxynitride film (SiON film) are formed by the CVD method, the ALD method, and the like. The nitride film forming method that can be used is, but not limited to the following, any method described in, for example, Japanese Patent Laid-Open No. 2002-334869 (Patent Literature 6) and WO2004/066377 (Patent Literature 7). While the photoresist film can be directly formed on such an intermediate layer film, an organic antireflective film (BARC) may also be formed on the intermediate layer film by spin coating, and the photoresist film may also be formed thereon.

As the intermediate layer, a polysilsesquioxane-based intermediate layer is also preferably used. The resist intermediate layer film is allowed to have an effect as an antireflective film, and thus tends to make it possible to effectively suppress reflection. A specific material for the polysilsesquioxane-based intermediate layer that can be used is, but not limited to the following, any material described in, for example, Japanese Patent Laid-Open No. 2007-226170 (Patent Literature 8) and Japanese Patent Laid-Open No. 2007-226204 (Patent Literature 9).

The next etching of the substrate can also be performed by an ordinary method, and, for example, when the substrate is made of $SiO_2$ or SiN, etching with mainly a fluorocarbon gas can be performed, and when the substrate is made of p-Si, Al, or W, etching mainly using a chlorine-based gas or bromine-based gas can be performed. In the case where the substrate is processed by the etching with a fluorocarbon gas, the silicon-containing resist in a two-layer resist process and the silicon-containing intermediate layer in a three-layer process are peeled off at the same time as the processing of the substrate. On the other hand, in the case where the substrate is processed by the etching with a chlorine-based gas or bromine-based gas, the silicon-containing resist layer or the silicon-containing intermediate layer is peeled off separately, and is generally peeled off by dry etching with a fluorocarbon gas after the substrate is processed.

The underlayer film of the present embodiment is characterized by being excellent in etching resistance of such a substrate. Herein, the substrate that can be used is appropriately selected from known ones, and is not particularly limited, but includes Si, α-Si, p-Si, $SiO_2$, SiN, SiON, W, TiN, and Al substrates. In addition, the substrate may also be a laminate having a processed film (processed substrate) on a base material (support). Such a processed film includes various Low-k films made of Si, $SiO_2$, SiON, SiN, p-Si, α-Si, W, W—Si, Al, Cu, and Al—Si, and stopper films thereof, and a material different from the base material (support) is preferably used therefor. Herein, the thickness of the substrate to be processed or the processed film is not particularly limited, but is usually preferably about 50 to 10000 nm, more preferably 75 to 5000 nm.

EXAMPLES

Hereinafter, the present embodiment will be described by Synthesis Examples, Synthesis Comparative Examples, Examples and Comparative Examples in more detail, but the present embodiment is not limited thereto at all.

(Structure of Compound)

The structure of each compound was confirmed by performing 1H-NMR measurement with an "Advance 600II spectrometer" manufactured by Bruker Corporation under the following conditions.
Frequency: 400 MHz
Solvent: d6-DMSO
Internal standard: TMS
Measurement temperature: 23° C.

(Carbon Concentration and Oxygen Concentration)

The carbon concentration and the oxygen concentration (% by mass) were measured by organic element analysis with the following apparatus.
Apparatus: CHN CORDER MT-6 (manufactured by Yanaco Bunseki Kogyo Co.)

(Molecular Weight)

The molecular weight of each compound was measured by FD-MS analysis with "JMS-T100GCV" manufactured by JEOL Ltd.

(Molecular Weight in Terms of Polystyrene)

With respect to the molecular weight of each resin, gel permeation chromatography (GPC) analysis was used to determine the weight average molecular weight (Mw) and the number average molecular weight (Mn) in terms of polystyrene and to determine the degree of dispersion (Mw/Mn).
Apparatus: Shodex GPC-101 type (manufactured by Showa Denko K. K.)
Column: KF-80M×3
Eluent: THF 1 mL/min
Temperature: 40° C.

(Thermal Weight Loss Temperature)

An "EXSTAR 6000 DSC apparatus" manufactured by SII NanoTechnology Inc. was used, and about 5 mg of a sample was placed in an unsealed aluminum container and heated to 500° C. at a rate of temperature rise of 10° C./min in a nitrogen gas (30 mL/min) stream. The 10% thermal weight loss temperature was here measured.

(Solubility)

The amount of each compound dissolved in 1-methoxy-2-propanol (PGME) and propylene glycol monomethyl ether acetate (PGMEA) was measured at 23° C., and the results were evaluated with respect to the solubility according to the following criteria.
Evaluation A: 20% by mass or more
Evaluation B: 10% by mass or more and less than 20% by mass
Evaluation C: less than 10% by mass (Synthesis Example 1) Synthesis of A-2 (Xanthene Compound)

In a container having an inner volume of 100 mL, equipped with a stirrer, a condenser and a burette, 3.5 g (20 mmol) of 2,6-naphthalenediol (reagent produced by Sigma-Aldrich Co. LLC.) and 2.3 g (20 mmol) of 4-iodobenzaldehyde (reagent produced by Tokyo Chemical Industry Co., Ltd.) were charged to 50 mL of γ-butyrolactone, and 0.3 g of p-toluenesulfonic acid was added thereto and stirred at 90° C. for 28 hours to perform a reaction, thereby providing a reaction liquid. Next, the reaction liquid was added to 500 g of pure water, and thereafter extracted by ethyl acetate and concentrated to provide a solution.

The resulting solution was subjected to separation by column chromatography and thereafter washing with chloroform, thereby providing 1.2 g of an objective compound (A-2) represented by the following formula (A-2).

The molecular weight of the resulting compound (A-2) was measured by the above method, and as a result, it was 516.

The resulting compound (A-2) was subjected to the NMR measurement under the above measurement conditions. Thus, the following peaks were observed and it was confirmed that the compound had a chemical structure of the following formula (A-2).

δ (ppm) 9.7 (2H, O—H), 7.2-8.5 (14H, Ph-H), 6.5 (1H, C—H)

Herein, the resulting compound (A-2) having a substituent of 2,6-naphthalenediol at the 1-position was confirmed from signals of protons at the 3-position and the 4-position being doublets.

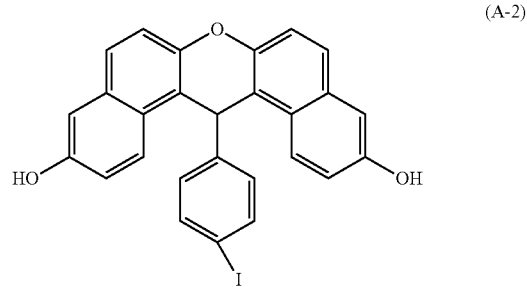 [SMILES: Oc1ccc2c3c(ccc2c1)Oc1ccc2cc(O)ccc2c1C3c1ccc(I)cc1]

(A-2)

As a result of organic element analysis, the carbon concentration and the oxygen concentration of the resulting compound (A-2) were 82.9% and 11.8%, respectively.

As a result of thermogravimetric measurement (TG), the 10% thermal weight loss temperature of the resulting compound (A-2) was 400° C. or higher. Therefore, the compound was evaluated to have a high heat resistance and be applicable to high-temperature baking.

As a result of evaluation of the solubility in PGME, the solubility was 20% by mass or more (Evaluation A), and as a result of evaluation of the solubility in PGMEA, the solubility was 10% by mass or more and less than 20% by mass (Evaluation B). Thus, compound (A-2) was evaluated to have an excellent solubility. Therefore, compound (A-2) was evaluated to have a high storage stability in a solution state and also be sufficiently applicable to an edge bead rinse liquid (mixed liquid of PGME/PGMEA) widely used in a semiconductor microfabrication process.

(Synthesis Example 2) Synthesis of A-3 (Xanthene Compound)

In a container having an inner volume of 300 mL, equipped with a stirrer, a condenser and a burette, 7.0 g (40 mmol) of 2,6-naphthalenediol (reagent produced by Sigma-Aldrich Co. LLC.) and 5.6 g (20 mmol) of 5-iodovanillin (reagent produced by Tokyo Chemical Industry Co., Ltd.) were charged to 100 mL of γ-butyrolactone, and 0.5 g of p-toluenesulfonic acid was added thereto and stirred at 90° C. for 87 hours to perform a reaction, thereby providing a reaction liquid. Next, the reaction liquid was added to 1000 g of pure water, and thereafter extracted by ethyl acetate and concentrated to provide a solution.

The resulting solution was subjected to separation by column chromatography and thereafter washing with chloroform, thereby providing 2.0 g of an objective compound (A-3) represented by the following formula (A-3).

The molecular weight of the resulting compound (A-3) was measured by the above method, and as a result, it was 562.

The resulting compound (A-3) was subjected to the NMR measurement under the above measurement conditions. Thus, the following peaks were observed and it was confirmed that the compound had a chemical structure of the following formula (A-3).

δ (ppm) 9.7, 9.3 (3H, O—H), 7.2-8.5 (12H, Ph-H), 6.4 (1H, C—H), 3.7 (3H, O—C—H)

Herein, the resulting compound (A-3) having a substituent of 2,6-naphthalenediol at the 1-position was confirmed from signals of protons at the 3-position and the 4-position being doublets.

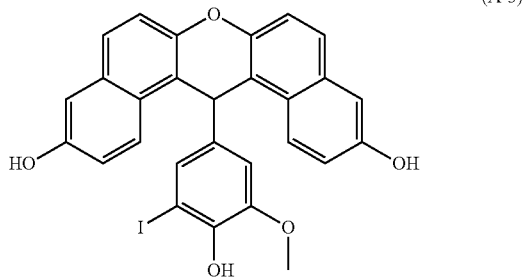

(A-3)

As a result of organic element analysis, the carbon concentration and the oxygen concentration of the resulting compound (A-3) were 82.9% and 11.8%, respectively.

As a result of thermogravimetric measurement (TG), the 10% thermal weight loss temperature of the resulting compound (A-3) was 400° C. or higher. Therefore, the compound was evaluated to have a high heat resistance and be applicable to high-temperature baking.

As a result of evaluation of the solubility in PGME and PGMEA, each solubility was 20% by mass or more (Evaluation A), and compound (A-3) was evaluated to have an excellent solubility. Therefore, compound (A-3) was evaluated to have a high storage stability in a solution state and also be sufficiently applicable to an edge bead rinse liquid (mixed liquid of PGME/PGMEA) widely used in a semiconductor microfabrication process.

(Synthesis Example 3) Synthesis of A-4 (Xanthene Compound)

In a container having an inner volume of 300 mL, equipped with a stirrer, a condenser and a burette, 7.0 g (40 mmol) of 2,6-naphthalenediol (reagent produced by Sigma-Aldrich Co. LLC.) and 4.5 g (20 mmol) of 5-iodo-2-furancarbaldehyde (reagent produced by Tokyo Chemical Industry Co., Ltd.) were charged to 100 mL of γ-butyrolactone, and 0.5 g of p-toluenesulfonic acid was added thereto and stirred at 90° C. for 24 hours to perform a reaction, thereby providing a reaction liquid. Next, the reaction liquid was added to 300 g of pure water, and thereafter extracted by ethyl acetate and concentrated to provide a solution.

The resulting solution was subjected to separation by column chromatography and thereafter washing with chloroform, thereby providing 2.5 g of an objective compound represented by the following formula (A-4).

The molecular weight of the resulting compound (A-4) was measured by the above method, and as a result, it was 506.

The resulting compound (A-4) was subjected to the NMR measurement under the above measurement conditions. Thus, the following peaks were observed and it was confirmed that the compound had a chemical structure of the following formula (A-4).

δ (ppm) 9.5 (2H, O—H), 7.1-8.3 (12H, Ph-H), 6.2 (1H, C—H)

Herein, the resulting compound (A-4) having a substituent of 2,6-naphthalenediol at the 1-position was confirmed from signals of protons at the 3-position and the 4-position being doublets.

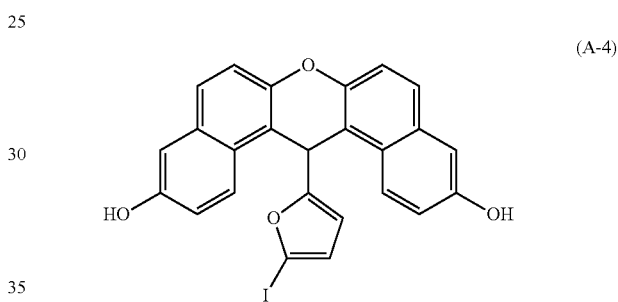

(A-4)

As a result of organic element analysis, the carbon concentration and the oxygen concentration of the resulting compound (A-4) were 78.9% and 16.8%, respectively.

As a result of thermogravimetric measurement (TG), the 10% thermal weight loss temperature of the resulting compound (A-4) was 400° C. or higher. Therefore, the resin was evaluated to have a high heat resistance and be applicable to high-temperature baking.

As a result of evaluation of the solubility in PGME and PGMEA, each solubility was 20% by mass or more (Evaluation A), and compound (A-4) was evaluated to have an excellent solubility. Therefore, compound (A-4) was evaluated to have a high storage stability in a solution state and also be sufficiently applicable to an edge bead rinse liquid (mixed liquid of PGME/PGMEA) widely used in a semiconductor microfabrication process.

(Synthesis Example 4) Synthesis of B-2 (Xanthene Compound)

Except that 3.5 g (20 mmol) of 2,6-naphthalenediol was changed to 3.5 g (20 mmol) of 2,7-naphthalenediol (reagent produced by Sigma-Aldrich Co. LLC.) and the reaction time was changed from 28 hours to 8 hours, the same manner as in Synthesis Example 1 was performed to provide 1.8 g of an objective compound (B-2) represented by the following formula (B-2).

The molecular weight of the resulting compound (B-2) was measured by the above method, and as a result, it was 516.

The resulting compound (B-2) was subjected to the NMR measurement under the above measurement conditions. Thus, the following peaks were observed and it was confirmed that the compound had a chemical structure of the following formula (B-2).

δ (ppm) 9.9 (2H, O—H), 7.0-8.3 (14H, Ph-H), 6.1 (1H, C—H)

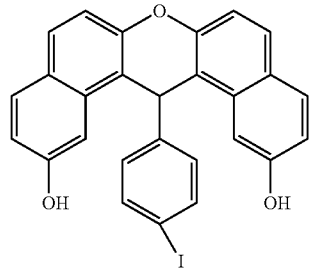

(B-2)

As a result of organic element analysis, the carbon concentration and the oxygen concentration of the resulting compound (B-2) were 82.9% and 11.8%, respectively.

As a result of thermogravimetric measurement (TG), the 10% thermal weight loss temperature of the resulting compound (B-2) was 400° C. or higher. Therefore, the compound was evaluated to have a high heat resistance and be applicable to high-temperature baking.

As a result of evaluation of the solubility in PGME and PGMEA, each solubility was 20% by mass or more (Evaluation A), and compound (B-2) was evaluated to have an excellent solubility. Therefore, compound (B-2) was evaluated to have a high storage stability in a solution state and also be sufficiently applicable to an edge bead rinse liquid (mixed liquid of PGME/PGMEA) widely used in a semiconductor microfabrication process.

(Synthesis Example 5) Synthesis of B-3 (Xanthene Compound)

Except that 7.0 g (40 mmol) of 2,6-naphthalenediol was changed to 7.0 g (40 mmol) of 2,7-naphthalenediol (reagent produced by Sigma-Aldrich Co. LLC.) and the reaction time was changed from 87 hours to 10 hours, the same manner as in Synthesis Example 2 was performed to provide 2.0 g of an objective compound (B-3) represented by the following formula (B-3). The molecular weight of the resulting compound (B-3) was measured by the above method, and as a result, it was 562.

The resulting compound (B-3) was subjected to the NMR measurement under the above measurement conditions. Thus, the following peaks were observed and it was confirmed that the compound had a chemical structure of the following formula (B-3).

δ (ppm) 9.9, 9.4 (3H, O—H), 7.0-8.3 (12H, Ph-H), 6.0 (1H, C—H), 3.8 (3H, O—C—H)

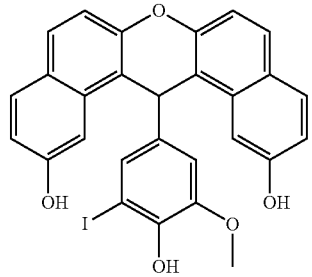

(B-3)

As a result of organic element analysis, the carbon concentration and the oxygen concentration of the resulting compound (B-3) were 82.9% and 11.8%, respectively.

As a result of thermogravimetric measurement (TG), the 10% thermal weight loss temperature of the resulting compound (B-3) was 400° C. or higher. Therefore, the compound was evaluated to have a high heat resistance and be applicable to high-temperature baking.

As a result of evaluation of the solubility in PGME and PGMEA, each solubility was 20% by mass or more (Evaluation A) and compound (B-3) was evaluated to have an excellent solubility. Therefore, compound (B-3) was evaluated to have a high storage stability in a solution state and also be sufficiently applicable to an edge bead rinse liquid (mixed liquid of PGME/PGMEA) widely used in a semiconductor microfabrication process.

(Synthesis Example 6) Synthesis of B-4 (Xanthene Compound)

In a container having an inner volume of 300 mL, equipped with a stirrer, a condenser and a burette, 7.0 g (40 mmol) of 2,7-naphthalenediol (reagent produced by Sigma-Aldrich Co. LLC.) and 4.5 g (20 mmol) of 5-iodo-2-furancarbaldehyde (reagent produced by Tokyo Chemical Industry Co., Ltd.) were charged to 100 mL of γ-butyrolactone, and 0.5 g of p-toluenesulfonic acid was added thereto and stirred at 90° C. for 12 hours to perform a reaction, thereby providing a reaction liquid. Next, the reaction liquid was added to 300 g of pure water, and thereafter extracted by ethyl acetate and concentrated to provide a solution.

The resulting solution was subjected to separation by column chromatography and thereafter washing with chloroform, thereby providing 3.7 g of an objective compound represented by the following formula (B-4).

The molecular weight of the resulting compound (B-4) was measured by the above method, and as a result, it was 506.

The resulting compound (B-4) was subjected to the NMR measurement under the above measurement conditions. Thus, the following peaks were observed and it was confirmed that the compound had a chemical structure of the following formula (B-4).

δ (ppm) 9.4 (2H, O—H), 7.1-8.2 (12H, Ph-H), 6.2 (1H, C—H)

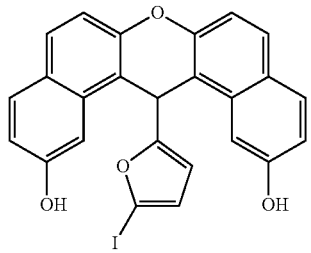

(B-4)

As a result of organic element analysis, the carbon concentration and the oxygen concentration of the resulting compound (B-4) were 78.9% and 16.8%, respectively.

As a result of thermogravimetric measurement (TG), the 10% thermal weight loss temperature of the resulting compound (B-4) was 400° C. or higher. Therefore, the compound was evaluated to have a high heat resistance and be applicable to high-temperature baking.

As a result of evaluation of the solubility in PGME and PGMEA, each solubility was 20% by mass or more (Evaluation A) and compound (B-4) was evaluated to have an excellent solubility. Therefore, compound (B-4) was evaluated to have a high storage stability in a solution state and also be sufficiently applicable to an edge bead rinse liquid (mixed liquid of PGME/PGMEA) widely used in a semiconductor microfabrication process.

(Synthesis Example 7) Synthesis of Resin (IR-1)

A four-neck flask having a bottom outlet and an inner volume of 1 L, equipped with a Dimroth condenser, a thermometer and a stirring blade was prepared. To this four-neck flask were charged 36.6 g of compound (A-2) obtained in Synthesis Example 1 (70 mmol, produced by Mitsubishi Gas Chemical Company, Inc.), 21.0 g (280 mmol as formaldehyde, produced by Mitsubishi Gas Chemical Company, Inc.) of a 40% by mass aqueous formalin solution and 0.97 mL of 98% by mass sulfuric acid (produced by Kanto Chemical Co., Inc.) under a nitrogen stream, and the reaction was allowed to run under ordinary pressure for 7 hours with refluxing at 100° C. Thereafter, 180.0 g of o-xylene (special grade chemical, produced by Wako Pure Chemical Industries, Ltd.) as a dilution solvent was added to the reaction liquid and left to stand, and then an aqueous phase being a bottom phase was removed. Furthermore, the resultant was neutralized and washed with water, and o-xylene was distilled off under reduced pressure, thereby providing 34.1 g of a resin (IR-1) as a brown solid.

In the resulting resin (IR-1), Mn was 1875, Mw was 3550, and Mw/Mn was 1.89. In addition, the carbon concentration was 77.6% by mass, and the oxygen concentration was 9.5% by mass.

As a result of thermogravimetric measurement (TG), the 10% thermal weight loss temperature of the resulting resin (IR-1) was 350° C. or higher and lower than 400° C. Therefore, the compound was evaluated to be applicable to high-temperature baking.

As a result of evaluation of the solubility in PGME and PGMEA, the solubility was 20% by mass or more (Evaluation A), and resin (IR-1) was evaluated to have an excellent solubility.

(Synthesis Example 8) Synthesis of Resin (IR-2)

A four-neck flask having a bottom outlet and an inner volume of 1 L, equipped with a Dimroth condenser, a thermometer and a stirring blade was prepared. To this four-neck flask were charged 36.6 g of compound (A-2) obtained in Synthesis Example 1 (70 mmol, produced by Mitsubishi Gas Chemical Company, Inc.), 50.9 g of 4-biphenylaldehyde (280 mmol, produced by Mitsubishi Gas Chemical Company, Inc.), 100 mL of anisole (produced by Kanto Chemical Co., Inc.) and 10 mL of oxalic acid dihydrate (produced by Kanto Chemical Co., Inc.) under a nitrogen stream, and the reaction was allowed to run under ordinary pressure for 7 hours with refluxing at 100° C. Thereafter, 180.0 g of o-xylene (special grade chemical, produced by Wako Pure Chemical Industries, Ltd.) as a dilution solvent was added to the reaction liquid and left to stand, and then an aqueous phase being a bottom phase was removed. Furthermore, the resultant was neutralized and washed with water, and the solvent and the unreacted 4-biphenylaldehyde in the organic phase were distilled off under reduced pressure, thereby providing 34.7 g of a resin (IR-2) as a brown solid.

In the resulting resin (IR-2), Mn was 1682, Mw was 2910, and Mw/Mn was 1.73. In addition, the carbon concentration was 81.2% by mass, and the oxygen concentration was 8.5% by mass.

As a result of thermogravimetric measurement (TG), the 10% thermal weight loss temperature of the resulting resin (IR-2) was 350° C. or higher and lower than 400° C. Therefore, the compound was evaluated to be applicable to high-temperature baking.

As a result of evaluation of the solubility in PGME and PGMEA, the solubility was 20% by mass or more (Evaluation A), and resin (IR-2) was evaluated to have an excellent solubility.

(Synthesis Comparative Example 1) Synthesis of Resin (CR-1) for Comparative Examples A four-neck flask having a bottom outlet and an inner volume of 10 L, equipped with a Dimroth condenser, a thermometer and a stirring blade was prepared. To this four-neck flask were charged 1.09 kg (7 mol, produced by Mitsubishi Gas Chemical Company, Inc.) of 1,5-dimethylnaphthalene, 2.1 kg (28 mol as formaldehyde, produced by Mitsubishi Gas Chemical Company, Inc.) of a 40% by mass aqueous formalin solution and 0.97 mL of 98% by mass sulfuric acid (produced by Kanto Chemical Co., Inc.) under a nitrogen stream, and allowed the reaction to run under ordinary pressure for 7 hours with refluxing at 100° C. Thereafter, ethylbenzene (special grade chemical, produced by Wako Pure Chemical Industries, Ltd.) (1.8 kg) as a dilution solvent was added to the reaction solution and left to stand, and then an aqueous phase being a bottom phase was removed. Furthermore, the resultant was neutralized and washed with water, and ethylbenzene and the unreacted 1,5-dimethylnaphthalene were distilled off under reduced pressure, thereby providing 1.25 kg of a dimethylnaphthalene formaldehyde resin as a light-brown solid.

With respect to the molecular weight of the resulting dimethylnaphthalene formaldehyde, Mn was 562, Mw was 1168 and Mw/Mn was 2.08. In addition, the carbon concentration was 84.2% by mass, and the oxygen concentration was 8.3% by mass.

Subsequently, a four-neck flask having an inner volume of 0.5 L, equipped with a Dimroth condenser, a thermometer and a stirring blade, was prepared. To this four-neck flask were charged 100 g (0.51 mol) of the dimethylnaphthalene formaldehyde resin obtained as described above and 0.05 g of paratoluenesulfonic acid under a nitrogen stream, heated for 2 hours with the temperature being raised to 190° C., and then stirred. Thereafter, 52.0 g (0.36 mol) of 1-naphthol was further added thereto, and further heated to 220° C. to allow the reaction to run for 2 hours. After being diluted with a solvent, the resultant was neutralized and washed with water, and the solvent was removed under reduced pressure to thereby provide 126.1 g of a modified resin (CR-1) as a blackish brown solid.

With respect to the resulting resin (CR-1), Mn was 885, Mw was 2220 and Mw/Mn was 4.17. In addition, the carbon concentration was 89.1% by mass and the oxygen concentration was 4.5% by mass.

Examples 1 to 8 and Comparative Example 1

Each composition for forming an underlayer film for lithography was prepared so that each composition shown in the Table was achieved. The following materials were used as materials shown in Table 1.
- Acid generator: di-tert-butyldiphenyliodonium nonafluoromethanesulfonate (DTDPI) produced by Midori Kagaku Co., Ltd.
- Crosslinking agent: Nikalac MX270 (Nikalac) produced by Sanwa Chemical Co., Ltd.
- Organic solvent: propylene glycol monomethyl ether acetate (PGMEA)
- Novolac: PSM4357 produced by Gun Ei Chemical Industry Co., Ltd.

The composition for forming an underlayer film of each of Examples 1 to 8 and Comparative Example 1 was evaluated with respect to preservation stability and thin film formation according to the following methods. The results are shown in Table 1.

[Preservation Stability]

The preservation stability of each composition for forming an underlayer film, including each compound, was evaluated as follows: each composition for forming an underlayer film was prepared in each compounding proportion described in Table 1 and thereafter left to stand at 23° C. for 3 days, and the presence of precipitation was visually confirmed, thereby rating a case where no precipitation was observed as "○", and a case where any precipitation was observed as "X".

[Thin Film Formation]

Each composition for forming an underlayer film was spin-coated on a clean silicon substrate, and thereafter baked at 240° C. for 60 seconds to prepare each underlayer film having a thickness of 200 nm. With respect to the underlayer film prepared, a case where the solution was uniform to allow thin film formation to be favorable was rated as "○" and a case where any defect was caused in thin film formation was rated as "X".

[Etching Resistance]

Next, an etching test was performed under conditions shown below to evaluate etching resistance. The evaluation results are shown in Table 1.

[Etching Test]

Etching apparatus: RIE-10NR manufactured by Samco Inc.
Output: 50 W
Pressure: 20 Pa
Time: 2 min
Etching Gas
Ar gas flow rate:$CF_4$ gas flow rate:$O_2$ gas flow rate=50:5:5 (sccm)

The evaluation of etching resistance was performed according to the following procedure.

First, an underlayer film of novolac was prepared under the same conditions as those in Example 1 except that novolac (PSM4357 produced by Gunei Chemical Industry Co., Ltd.) was used instead of the compound (A-2) used in Example 1. Then, the etching test was performed with respect to the underlayer film of novolac as a subject, and the etching rate in that time was measured.

Then, the etching test was performed with respect to each underlayer film of Examples 1 to 8 and Comparative Example 1 as a subject, and the etching rate in that time was measured.

Then, the etching resistances were evaluated according to the following criteria based on the etching rate of the underlayer film using novolac.

[Evaluation Criteria]

A; etching rate of less than −10% compared with the etching rate of the underlayer film of novolac
B; etching rate of −10% to +5% compared with the etching rate of underlayer film of novolac
C; etching rate of more than +5% compared with the etching rate of the underlayer film of novolac

TABLE 1

|  | Material for forming underlayer film (parts by mass) | Organic solvent (parts by mass) | Acid generator (parts by mass) | Crosslinking agent (parts by mass) | Preservation stability | Thin film formation | Etching resistance evaluation |
|---|---|---|---|---|---|---|---|
| Example 1 | A-2 (10) | PGMEA (90) | DTDPI (0.5) | Nikalac (0.5) | ○ | ○ | A |
| Example 2 | A-3 (10) | PGMEA (90) | DTDPI (0.5) | Nikalac (0.5) | ○ | ○ | A |
| Example 3 | A-4 (10) | PGMEA (90) | DTDPI (0.5) | Nikalac (0.5) | ○ | ○ | A |
| Example 4 | B-2 (10) | PGMEA (90) | DTDPI (0.5) | Nikalac (0.5) | ○ | ○ | A |
| Example 5 | B-3 (10) | PGMEA (90) | DTDPI (0.5) | Nikalac (0.5) | ○ | ○ | A |
| Example 6 | B-4 (10) | PGMEA (90) | DTDPI (0.5) | Nikalac (0.5) | ○ | ○ | A |
| Example 7 | IR-1 (10) | PGMEA (90) | DTDPI (0.5) | Nikalac (0.5) | ○ | ○ | B |

TABLE 1-continued

| | Material for forming underlayer film (parts by mass) | Organic solvent (parts by mass) | Acid generator (parts by mass) | Crosslinking agent (parts by mass) | Preservation stability | Thin film formation | Etching resistance evaluation |
|---|---|---|---|---|---|---|---|
| Example 8 | IR-2 (10) | PGMEA (90) | DTDPI (0.5) | Nikalac (0.5) | ○ | ○ | A |
| Comparative Example 1 | CR-1 (10) | PGMEA (90) | DTDPI (0.5) | Nikalac (0.5) | ○ | ○ | C |

Example 9

Then, the composition for forming an underlayer film for lithography in Example 1 was coated on a $SiO_2$ substrate having a film thickness of 300 nm, and baked at 240° C. for 60 seconds and further at 400° C. for 120 seconds to thereby form an underlayer film having a film thickness of 85 nm. A resist solution for ArF was coated on the underlayer film, and baked at 130° C. for 60 seconds to thereby form a photoresist layer having a film thickness of 140 nm. Herein, as the resist solution for ArF, one prepared by blending 5 parts by mass of the compound represented by the following formula (5), 1 part by mass of triphenylsulfonium nonafluoromethanesulfonate, 2 parts by mass of tributylamine, and 92 parts by mass of PGMEA was used.

A compound represented by formula (5) was prepared as follows. That is, 4.15 g of 2-methyl-2-methacryloyloxyadamantane, 3.00 g of methacryloyloxy-γ-butyrolactone, 2.08 g of 3-hydroxy-1-adamantyl methacrylate and 0.38 g of azobisisobutyronitrile were dissolved in 80 mL of tetrahydrofuran to provide a reaction solution. This reaction solution was subjected to polymerization under a nitrogen atmosphere for 22 hours with the reaction temperature being kept at 63° C., and thereafter the reaction solution was dropped in 400 mL of n-hexane. A product resin thus obtained was solidified and purified, and a white powder produced was taken by filtration and dried under reduced pressure at 40° C. overnight to provide a compound represented by the following formula.

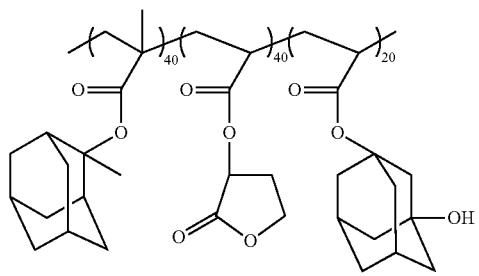

(5)

In the formula (5), the numerals "40", "40", and "20" indicate the proportions of the respective constituent units, and do not mean a block copolymer.

Then, the photoresist layer was exposed by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern.

Comparative Example 2

Except that no underlayer film was formed, the same manner as in Example 9 was performed to form a photoresist layer directly on a $SiO_2$ substrate to provide a positive-type resist pattern.

[Evaluation]

The shapes of the resist patterns of 40 nm L/S (1:1) and 80 nm L/S (1:1) provided in each of Example 9 and Comparative Example 2 were observed by using an electron microscope (S-4800) manufactured by Hitachi Ltd. A case where the shape of the resist pattern after development had no pattern collapse and had good rectangularity was evaluated to be good and a case the shape had pattern collapse and did not have good rectangularity was evaluated to be poor. In the observation results, the minimum line width where there was no pattern collapse and rectangularity was good was defined as the resolution and used as an evaluation index. Furthermore, the minimum amount of electron beam energy, where a good pattern shape could be drawn, was defined as the sensitivity and used as an evaluation index. The results are shown in Table 2.

TABLE 2

| | Material for forming underlayer film | Resolution (nmL/S) | Sensitivity (μC/cm$^2$) | Resist pattern formation after development |
|---|---|---|---|---|
| Example 9 | Material described in Example 1 | 40 | 10 | Good |
| Comparative Example 2 | Not used | 80 | 26 | Not good |

As can be seen from Table 2, it was at least confirmed that Example 9 was significantly superior in both of resolution and sensitivity as compared with Comparative Example 2. It was also confirmed that the resist pattern shape after development had no pattern collapse and had good rectangularity. Furthermore, it was also confirmed from the difference in the resist pattern shape after development that the material for forming an underlayer film for lithography in Example 1 had good adhesiveness with a resist material.

Example 10

The composition for forming an underlayer film for lithography used in Example 1 was coated on a $SiO_2$ substrate having a thickness of 300 nm, and baked at 240° C. for 60 seconds and further at 400° C. for 120 seconds to thereby form an underlayer film having a thickness of 90 nm. A silicon-containing intermediate layer material was coated on the underlayer film, and baked at 200° C. for 60 seconds to thereby form an intermediate layer film having a thickness of 35 nm. Furthermore, the resist solution for ArF was coated on the intermediate layer film, and baked at 130°

C. for 60 seconds to thereby form a photoresist layer having a thickness of 150 nm. Herein, as the silicon-containing intermediate layer material, a silicon atom-containing polymer obtained below was used.

In 200 g of tetrahydrofuran (THF) and 100 g of pure water were dissolved 16.6 g of 3-carboxypropyltrimethoxysilane, 7.9 g of phenyltrimethoxysilane and 14.4 g of 3-hydroxypropyltrimethoxysilane, the liquid temperature was set at 35° C., 5 g of oxalic acid was dropped, and thereafter the resultant was heated to 80° C. to perform a condensation reaction of silanol. Next, 200 g of diethyl ether was added to separate an aqueous layer, an organic liquid layer was washed with ultrapure water twice, 200 g of propylene glycol monomethyl ether acetate (PGMEA) was added, and THF, diethyl ether, and water were removed under reduced pressure with the liquid temperature being raised to 60° C., to provide a silicon atom-containing polymer.

Then, the photoresist layer was mask-exposed by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern of 45 nmL/S (1:1). Thereafter, a silicon-containing intermediate layer film (SOG) was subjected to dry etching processing with the resulting resist pattern as a mask by use of RIE-10NR manufactured by Samco Inc., and subsequently, dry etching processing of the underlayer film with the resulting silicon-containing intermediate layer film pattern as a mask and dry etching processing of the $SiO_2$ film with the resulting underlayer film pattern as a mask were sequentially performed.

The respective etching conditions are as shown below.
Etching Conditions of Resist Intermediate Layer Film with Resist Pattern
Output: 50 W
Pressure: 20 Pa
Time: 1 min
Etching Gas
Ar gas flow rate:$CF_4$ gas flow rate:$O_2$ gas flow rate=50:8:2 (sccm)
Etching Conditions of Resist Underlayer Film with Resist Intermediate Film Pattern
Output: 50 W
Pressure: 20 Pa
Time: 2 min
Etching Gas
Ar gas flow rate:$CF_4$ gas flow rate:$O_2$ gas flow rate=50:5:5 (sccm)
Etching Conditions of $SiO_2$ Film with Resist Underlayer Film Pattern
Output: 50 W
Pressure: 20 Pa
Time: 2 min
Etching Gas
Ar gas flow rate:$C_5F_{12}$ gas flow rate:$C_2F_6$ gas flow rate:$O_2$ gas flow rate=50:4:3:1 (sccm)
[Evaluation]
The pattern cross section (shape of $SiO_2$ film after etching) in Example 10, obtained as above, was observed by using an electron microscope (S-4800) manufactured by Hitachi Ltd., and it was thus at least confirmed that the underlayer film in each Example was favorable because the shape of the $SiO_2$ film after etching in multilayer resist processing was rectangular and no defect was observed.

As described above, the present embodiment is not intended to be limited to the above Examples, and can be appropriately modified without departing the gist thereof.

The present application is based on Japanese Patent Application (Japanese Patent Application No. 2015-170190) filed with JPO on Aug. 31, 2015, the content of which is herein incorporated as reference.

The compound and the resin according to the present invention have a relatively high heat resistance and also a relatively high solvent solubility, and can be applied to a wet process. Therefore, a material for forming an underlayer film for lithography, containing the compound or the resin according to the present invention, and a composition including the material can be widely and effectively utilized in various applications in which these properties are required. Therefore, the present invention can be widely and effectively utilized for, for example, an electric insulating material; a resist resin; a sealing resin for a semiconductor; an adhesive for a printed wiring board; an electric laminated board mounted on electrical equipment, electronic equipment, industrial equipment and the like; a matrix resin for a prepreg mounted on electrical equipment, electronic equipment, industrial equipment and the like; a material for a build-up laminated board; a resin for fiber-reinforced plastics; a sealing resin for a liquid crystal display panel; a paint; various coating agents; an adhesive; a coating agent for a semiconductor; a resist resin for a semiconductor; and a resin for forming an underlayer film. In particular, the present invention can be particularly effectively utilized in the field of an underlayer film for lithography and an underlayer film for a multilayer resist.

The invention claimed is:
1. A method for forming an underlayer film for lithography, comprising
forming an underlayer film on a substrate using a composition for forming an underlayer film, the composition including a solvent and a material for forming an underlayer film; and
forming at least one photoresist layer on the underlayer film,
the material for forming an underlayer film including at least any of a compound represented by following formula (1-1) or a resin comprising a structural unit derived from a compound represented by the following formula (1-1),

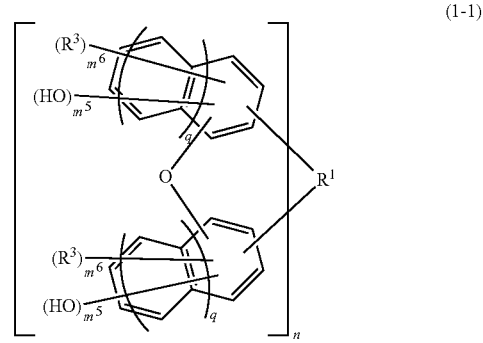

(1-1)

wherein $R^1$ represents a 2n-valent group having a 1 to 60 carbon atoms, or a single bond, each $R^3$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, or a thiol group, and may be the same or different in the same naphthalene ring or benzene ring, n is an integer of 1 to 4, structural formulae of n's structural units in square brackets [ ] may be the same or different when n is an integer of 2 or more, each $m^5$ is independently an integer of 1 to 6, each $m^6$ is independently an integer of 0 to 5, and $m^5+m^6$ is an integer of 1 to 6, and each q is independently 0 or 1, provided that at least one selected from the group consisting of $R^1$ and $R^3$ is a group having an iodine atom.

2. The method according to claim 1, wherein the compound represented by the formula (1-1) is a compound represented by following formula (1-2),

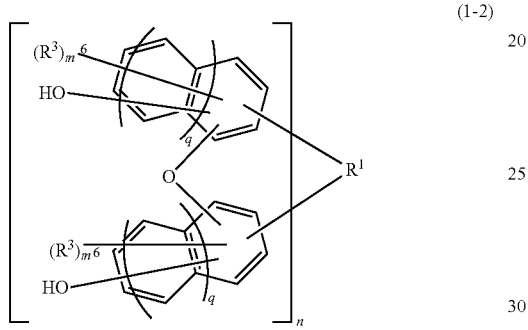
(1-2)

wherein (1-2), $R^1$, $R^3$, m, n and q are the same as defined above, and at least one selected from the group consisting of $R^1$ and $R^3$ is a group having an iodine atom.

3. The method according to claim 2, wherein the compound represented by the formula (1-2) is a compound represented by following formula (1-3),

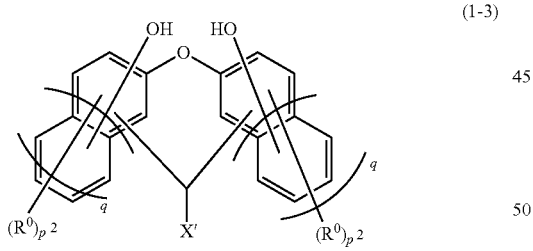
(1-3)

wherein q is the same as defined above, X' represents a hydrogen atom, a halogen atom, or a monovalent group having 1 to 59 carbon atoms, each $R^0$ independently represents an alkyl group having 1 to 4 carbon atoms, or a halogen atom, and may be the same or different in the same naphthalene ring or benzene ring, and each $p^2$ is independently an integer of 0 to 5, provided that at least one selected from the group consisting of X' and $R^0$ is a group having an iodine atom.

4. The method according to claim 3, wherein the compound represented by the formula (1-3) is a compound represented by following formula (1-4),

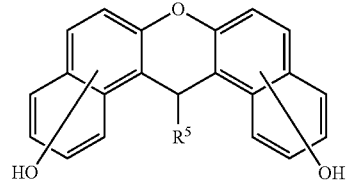
(1-4)

wherein $R^5$ represents an iodine atom, or a monovalent group selected from a straight, branched or cyclic alkyl group having an iodine atom and having 1 to 10 carbon atoms, an aryl group having an iodine atom and having 6 to 10 carbon atoms, a heterocyclic group having an iodine atom and having 6 to 10 carbon atoms, an alkenyl group having an iodine atom and having 2 to 10 carbon atoms, and an alkoxy group having an iodine atom and having 1 to 30 carbon atoms.

5. The method according to claim 4, wherein the compound represented by the formula (1-4) is a compound represented by following formula (1-5) or following formula (1-6),

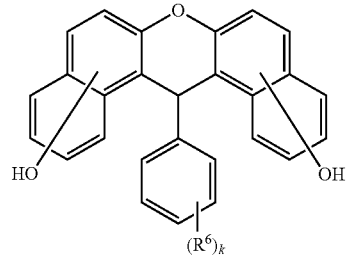
(1-5)

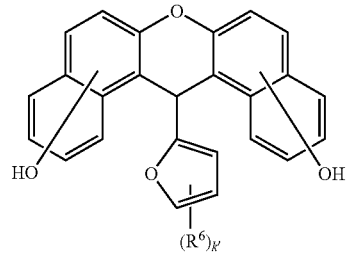
(1-6)

wherein $R^6$ represents at least one selected from the group consisting of a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group and a hydroxy group; and k is an integer of 1 to 5 and k' is an integer of 1 to 3, provided that at least one $R^6$ represents a monovalent group having an iodine atom.

6. The method according to claim 5, wherein the compound represented by the formula (1-5) or the formula (1-6) is at least one selected from the group consisting of following compounds.

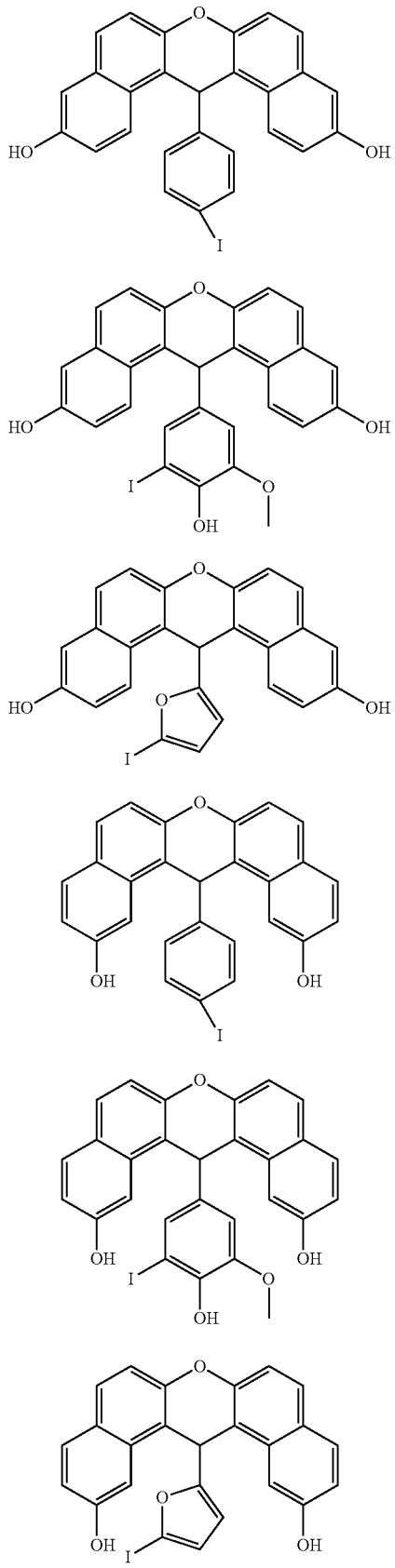

7. The method according to claim 1, wherein the composition further includes an acid generator.

8. The method according to claim 1, wherein the composition further includes a crosslinking agent.

9. An underlayer film for lithography, formed according to the method of claim 1.

wherein $R^1$ represents a 2n-valent group having a 1 to 60 carbon atoms, or a single bond, each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, or a hydroxyl group, and may be the same or different in the same naphthalene ring or benzene ring, n is an integer of 1 to 4, structural formulae of n's structural units in square brackets [ ] may be the same or different when n is an integer of 2 or more, X represents an oxygen atom, a sulfur atom, or a non-bridging group, each $m^2$ is independently an integer of 0 to 7, in which at least one $m^2$ is an integer of 1 to 7, and each q is independently 0 or 1, provided that at least one selected from the group consisting of $R^1$ and $R^2$ is a group having an iodine atom; and a step of irradiating a predetermined region of the photoresist layer with radiation, and developing it.

10. A resist pattern forming method comprising:

a step of forming an underlayer film on a substrate using a composition for forming an underlayer film, the composition including a solvent and a material for forming an underlayer film; and forming at least one photoresist layer on the underlayer film, the material for forming an underlayer film including at least any of a compound represented by following formula (1-1) or a resin comprising a structural unit derived from a compound represented by the following formula (1-1), (1-1)

wherein $R^1$ represents a 2n-valent group having a 1 to 60 carbon atoms, or a single bond, each $R^3$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, or a thiol group, and may be the same or different in the same naphthalene ring or benzene ring, n is an integer of 1 to 4, structural formulae of n's structural units in square brackets may be the same or different when n is an integer of 2 or more, each $m^5$ is independently an integer of 1 to 6, each $m^6$ is independently an integer of 0 to 5, and $m^5+m^6$ is an integer of 1 to 6, and each q is independently 0 or 1, provided that at least one selected from the group consisting of $R^1$ and $R^3$ is a group having an iodine atom; and a step of irradiating a predetermined region of the photoresist layer with radiation, and developing it.

* * * * *

UNITED STATES PATENT AND TRADEMARK OFFICE
CERTIFICATE OF CORRECTION

PATENT NO. : 11,137,686 B2
APPLICATION NO. : 15/756463
DATED : October 5, 2021
INVENTOR(S) : Toida et al.

Page 1 of 1

It is certified that error appears in the above-identified patent and that said Letters Patent is hereby corrected as shown below:

In the Claims

Column 78, Line (67):
In Claim 6, please delete "compounds." and insert -- compounds --, therefor.

Column 79, Line (60):
In Claim 6, after " 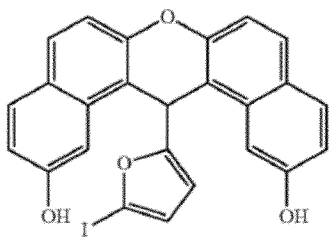 " please insert -- . --.

Column 80, Lines (7-25):
In Claim 9, below "claim 1." please delete "wherein $R^1$ represents a 2n-valent group having a 1 to 60 carbon atoms, or a single bond, each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, or a hydroxyl group, and may be the same or different in the same naphthalene ring or benzene ring, n is an integer of 1 to 4, structural formulae of n's structural units in square brackets [ ] may be the same or different when n is an integer of 2 or more, X represents an oxygen atom, a sulfur atom, or a non-bridging group, each $m^2$ is independently an integer of 0 to 7, in which at least one $m^2$ is an integer of 1 to 7, and each q is independently 0 or 1, provided that at least one selected from the group consisting of $R^1$ and $R^2$ is a group having an iodine atom; and a step of irradiating a predetermined region of the photoresist layer with radiation, and developing it.".

Column 80, Line (64):
In Claim 10, please delete "brackets" and insert -- brackets [ ] --, therefor.

Signed and Sealed this
Seventh Day of June, 2022

Katherine Kelly Vidal
*Director of the United States Patent and Trademark Office*